US012582789B2

(12) United States Patent
Yew et al.

(10) Patent No.: US 12,582,789 B2
(45) Date of Patent: Mar. 24, 2026

(54) MODULAR ORO-NASAL PATIENT INTERFACE

(71) Applicant: ResMed Asia Pte. Ltd., Singapore (SG)

(72) Inventors: Robin Yew, Singapore (SG); Weiyi Chia, Singapore (SG); Han Cheng Lin, Singapore (SG); Sipu Chen, Singapore (SG)

(73) Assignee: ResMed Asia Pte. Ltd., Singapore (SG)

( * ) Notice: Subject to any disclaimer, the term of this patent is extended or adjusted under 35 U.S.C. 154(b) by 537 days.

(21) Appl. No.: 18/300,319

(22) Filed: Apr. 13, 2023

(65) Prior Publication Data

US 2023/0347089 A1     Nov. 2, 2023

Related U.S. Application Data

(60) Provisional application No. 63/335,752, filed on Apr. 28, 2022.

(51) Int. Cl.
A61M 16/06     (2006.01)
A61M 16/20     (2006.01)

(52) U.S. Cl.
CPC .... A61M 16/0666 (2013.01); A61M 16/0683 (2013.01); A61M 16/208 (2013.01)

(58) Field of Classification Search
CPC .......... A61M 16/0666; A61M 16/0683; A61M 16/0616; A61M 16/0875; A61M 16/0816;
(Continued)

(56) References Cited

U.S. PATENT DOCUMENTS

| | | | |
|---|---|---|---|
| 4,782,832 A | 11/1988 | Trimble et al. | |
| 4,944,310 A | 7/1990 | Sullivan | |

(Continued)

FOREIGN PATENT DOCUMENTS

| | | |
|---|---|---|
| WO | WO 98/004310 A1 | 2/1998 |
| WO | WO 98/034665 A1 | 8/1998 |

(Continued)

OTHER PUBLICATIONS

"*Respiratory Physiology*", by John B. West, Lippincott Williams & Wilkins, 9th edition published 2012 (8 pages).

*Primary Examiner* — Rachel T Sippel
*Assistant Examiner* — Gwynneth L Howell
(74) *Attorney, Agent, or Firm* — Nixon & Vanderhye P.C.

(57)     ABSTRACT

A patient interface including a vent structure that allows a continuous flow of gases exhaled by the patient from an interior of a nasal plenum chamber to the ambient. The vent structure is sized and shaped to maintain the therapeutic pressure in the nasal plenum chamber in use. The vent structure includes a housing secured to the nasal plenum chamber, and a vent wall coupled to the rigid housing and selectively movable between a closed position and an open position. The vent wall is biased toward the closed position. The vent wall is maintained in the closed position and is configured to be positioned in the open position as a result of contact with an oral cushion in order to accommodate the oral cushion with an oral plenum chamber and form an oro-nasal cushion.

20 Claims, 33 Drawing Sheets

(58) Field of Classification Search

CPC .. A61M 16/00; A61M 16/06; A61M 16/0672; A61M 2207/00; A61M 2210/00; A61M 2210/06; A61M 2210/0618; A61M 2210/0625

See application file for complete search history.

(56) References Cited

U.S. PATENT DOCUMENTS

| | | | |
|---|---|---|---|
| 5,687,715 A | 11/1997 | Landis | |
| 6,532,959 B1 | 3/2003 | Berthon-Jones | |
| 6,581,594 B1 | 6/2003 | Drew et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 9,427,544 B2 * | 8/2016 | Frater | A61M 16/0622 |
| 2006/0124131 A1 * | 6/2006 | Chandran | A61M 16/0666 128/206.28 |
| 2009/0044808 A1 | 2/2009 | Guney et al. | |

| | | | |
|---|---|---|---|
| 2009/0050156 A1 | 2/2009 | Ng et al. | |
| 2009/0133696 A1 * | 5/2009 | Remmers | A61M 16/0493 128/204.26 |
| 2010/0000534 A1 | 1/2010 | Kooij et al. | |
| 2010/0132717 A1 * | 6/2010 | Davidson | A61M 16/0666 128/207.18 |
| 2013/0199537 A1 * | 8/2013 | Formica | A61M 16/06 128/205.25 |

FOREIGN PATENT DOCUMENTS

| | | |
|---|---|---|
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |

* cited by examiner

Nasal cavity

Oral cavity

Larynx

Vocal folds

Oesophagus

Trachea

Bronchus

Lung

Heart

Diaphragm

Alveolar sacs

Nasal cavity

Nasal bone

Lateral nasal cartilage

Greater alar cartilage

Nostril

Lip superior

Lip inferior

Hard palate

Soft palate

Oropharynx

Tongue

Epiglottis

Vocal folds

Larynx

Esophagus

Trachea

Frontal sinus

Nasal bone

Septum cartilage

Medial crus of greater alar cartilage

Anterior nasal spine

Epidermis

Adipose tissue

Nasal bone

Lateral cartilage

Septum cartilage

Greater alar cartilage

Frontal process of maxilla

Lesser alar cartilage

Fibrofatty tissue

Frontal bone

Supraorbital foramen

Nasal bones

Septal cartilage

Lateral cartilage

Sesamoid cartilage

Greater alar cartilage

Medial crus of greater alar cartilage

Anterior nasal spine

Infraorbital foramen

Lesser nasal cartilage

Alar fibrofatty tissue

Septal cartilage

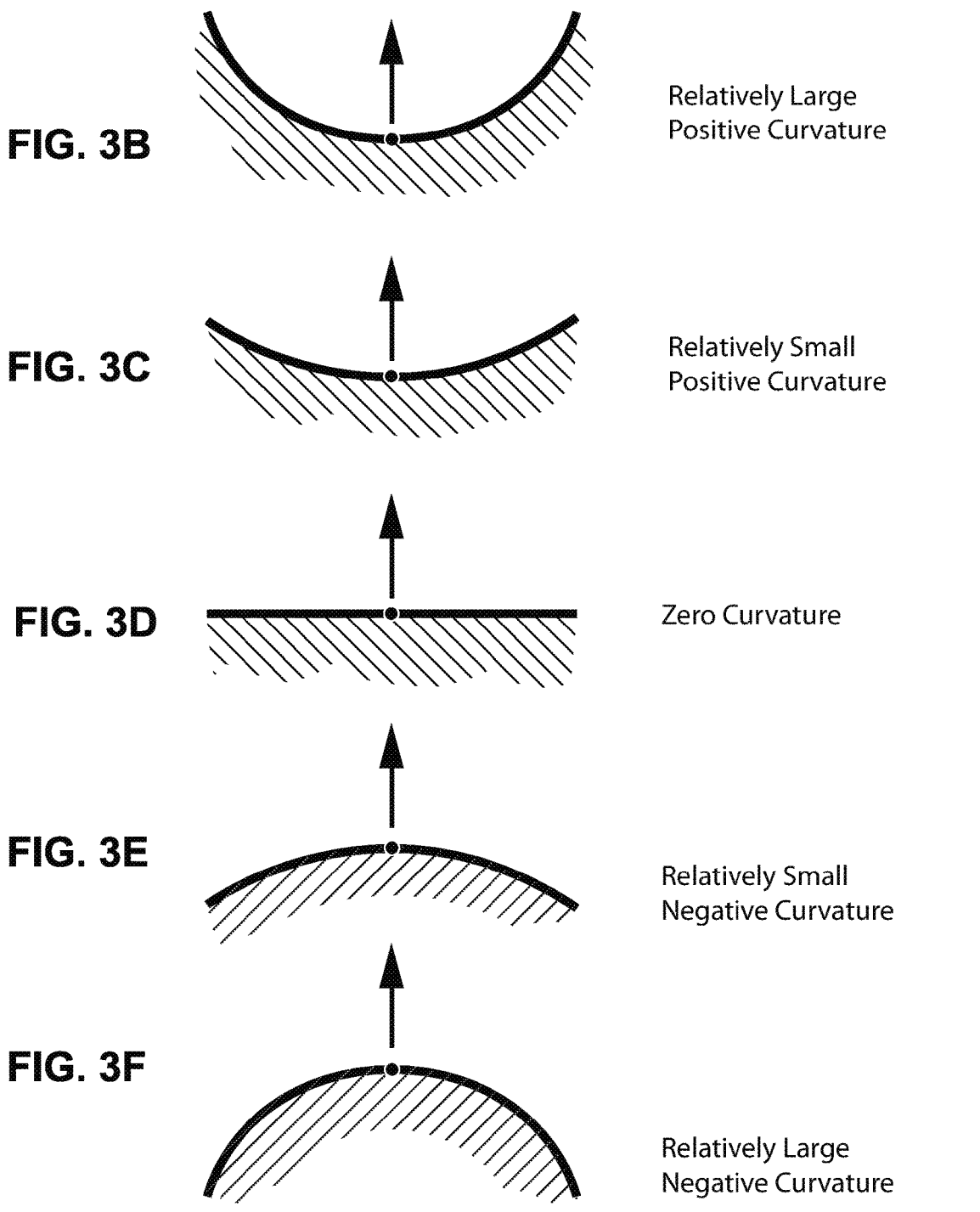
FIG. 3B          Relatively Large
                 Positive Curvature
FIG. 3C          Relatively Small
                 Positive Curvature
FIG. 3D          Zero Curvature
FIG. 3E          Relatively Small
                 Negative Curvature
FIG. 3F          Relatively Large
                 Negative Curvature Curve Surface Surface Interior surface Interior surface

FIG. 3M          FIG. 3N

Left-hand rule
Right-hand rule
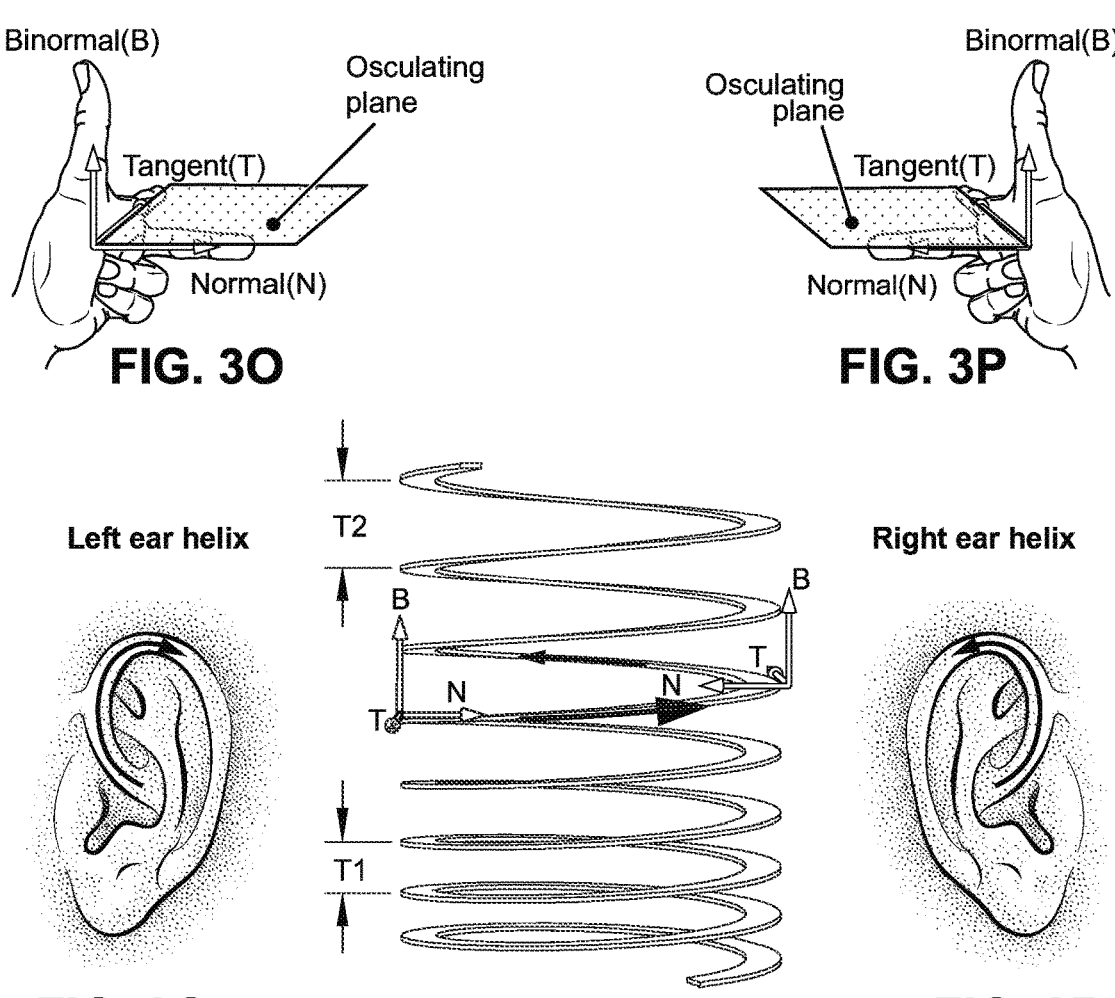
FIG. 3O
FIG. 3P
Left ear helix
Right ear helix
FIG. 3Q
Right-hand helix
Right-hand positive
FIG. 3S
FIG. 3R
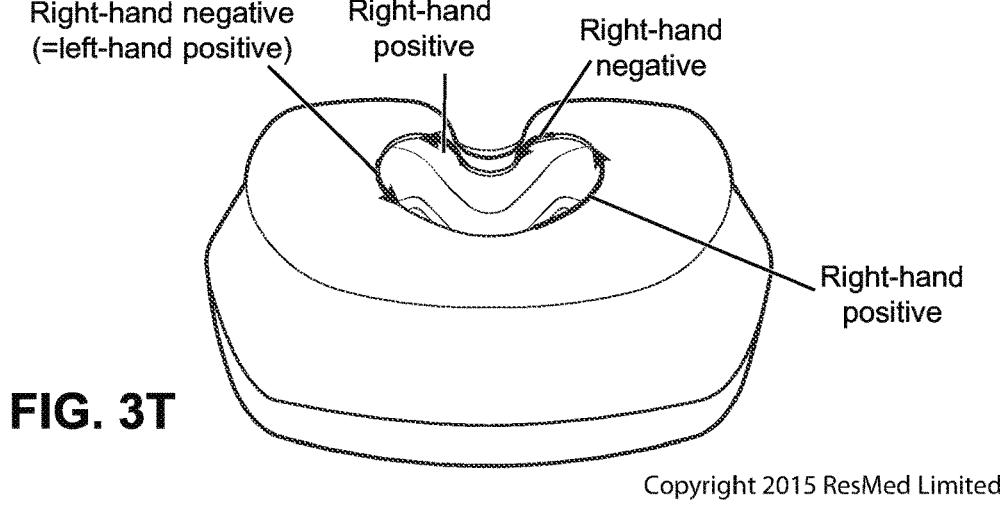
FIG. 3T

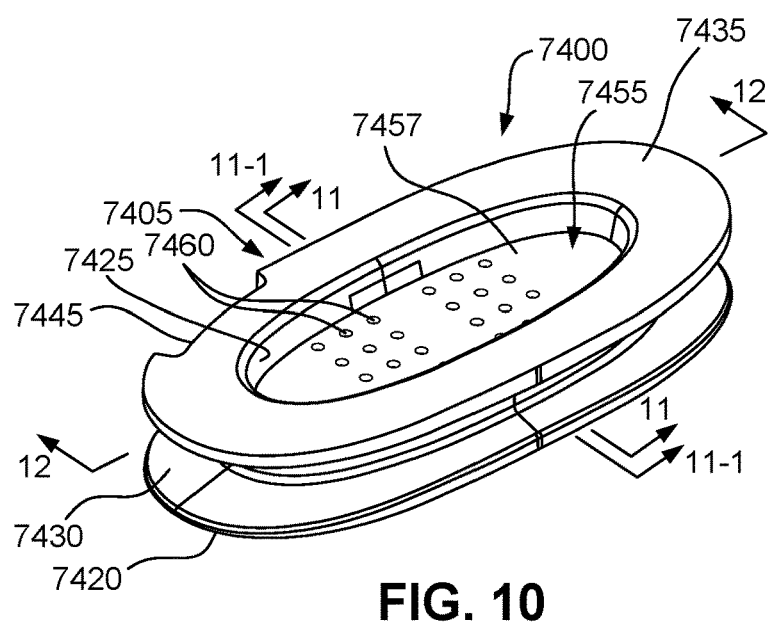
FIG. 10
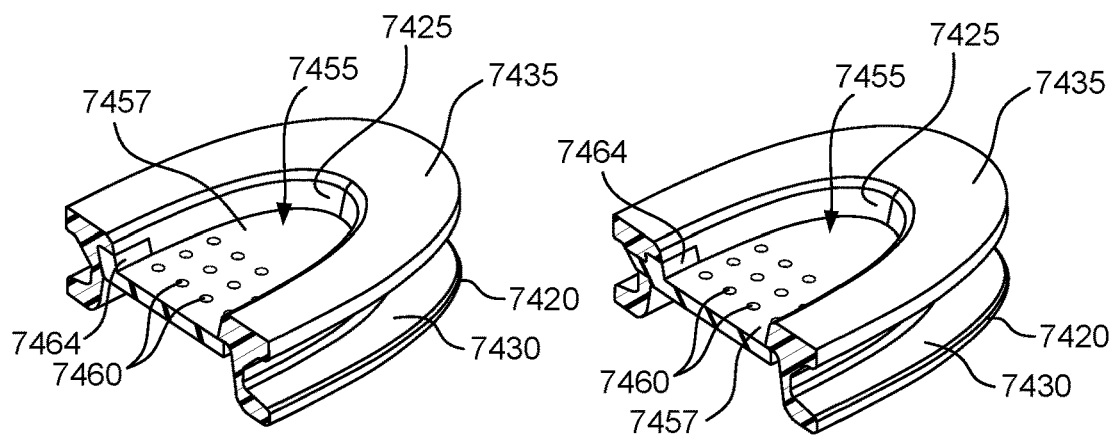
FIG. 11          FIG. 11-1
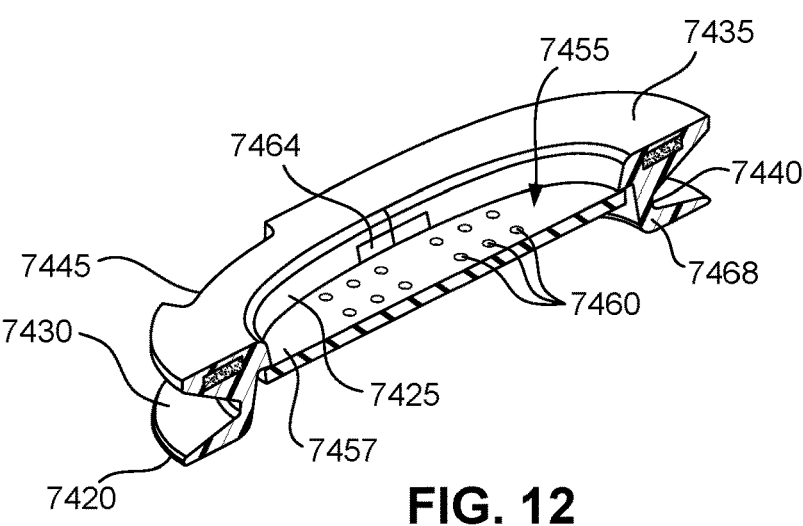
FIG. 12

7311

7312

7310

8340

8316

8312

8310

8314

7310        7312

8320

8324

N
S

N
S

8316

8310

7310

22-1

8340

8316

22-1

8312

8310

MODULAR ORO-NASAL PATIENT INTERFACE

1 CROSS-REFERENCE TO RELATED APPLICATIONS

This application claims the benefit of U.S. Provisional Application No. 63/335,752, the entire contents of which is hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hypoventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hypoventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube or endotracheal tube. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that may be held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004310; WO 2006/074513; WO 2010/135785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063328 and WO 2006/130903 (describing amongst other things aspects of the ResMed Limited MIRAGE LIBERTY™ full-face mask); International Patent Application WO 2009/052560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm, applied generally to the face area in and about the patient interface is more comfortable than cold 2.2.3.5 Data Management There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034665; International Patent Application Publication No. WO 2000/078381; U.S. Pat. No. 6,581,594; US Patent Application Publication No. US 2009/0050156; US Patent Application Publication No. 2009/0044808.

Table of noise of prior masks (ISO 17510-2:2007, 10 cmH2O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed MirageTM (*) | nasal | 29.5 | 21.5 | 1998 |
| ResMed UltraMirageTM | nasal | 36 (3) | 28 (3) | 2000 |
| ResMed Mirage ActivaTM | nasal | 32 (3) | 24 (3) | 2002 |
| ResMed Mirage MicroTM | nasal | 30 (3) | 22 (3) | 2008 |
| ResMed MirageTM SoftGel | nasal | 29 (3) | 22 (3) | 2008 |
| ResMed MirageTM FX | nasal | 26 (3) | 18 (3) | 2010 |
| ResMed Mirage SwiftTM (*) | nasal pillows | 37 | 29 | 2004 |
| ResMed Mirage SwiftTM II | nasal pillows | 28 (3) | 20 (3) | 2005 |
| ResMed Mirage SwiftTM LT | nasal pillows | 25 (3) | 17 (3) | 2008 |
| ResMed AirFit P10 | nasal pillows | 21 (3) | 13 (3) | 2014 |

((*) one specimen only, measured using test method specified in ISO 3744 in CPAP mode at 10 cmH2O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular, it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

One form of the present technology comprises a positioning and stabilising structure configured to provide a force to hold the seal-forming structure in a therapeutically effective position on the patient's head. The positioning and stabilising structure includes at least one strap.

One form of the present technology comprises a patient interface comprising a plenum chamber, a seal-forming structure, and a positioning and stabilising structure.

An aspect of one form of the present technology comprises a plenum chamber pressurisable to a therapeutic pressure of at least 4 cmH$_2$O above ambient air pressure, and a seal-forming structure constructed and arranged to form a seal with a region of the patient's face surrounding an entrance to the patient's airways.

An aspect of one form of the present technology comprises a plenum chamber pressurisable to a therapeutic pressure of at least 4 cmH$_2$O above ambient air pressure, a seal-forming structure constructed and arranged to form a seal with a region of the patient's face surrounding an entrance to the patient's airways, and a positioning and stabilising structure configured to provide a force to hold the seal forming structure in a therapeutically effective position.

An aspect of certain forms of the present technology is to provide methods and/or apparatus that improve the compliance of patients with respiratory therapy.

One form of the present technology comprises a modular patient interface including a nasal portion removably connected to an oral portion.

Another aspect of one form of the present technology is a vent structure configured to be used with a nasal plenum chamber. The vent structure includes a vent body and a vent wall movably (e.g., bendably, translatably, pivotably) connected to the vent body.

Another aspect of one form of the present technology is a nasal patient interface usable alone or removably connectable to an oral cushion to form an oro-nasal cushion.

Another aspect of one form of the present technology is a nasal patient interface including a vent structure. The vent structure includes a vent body permanently connected to a nasal plenum chamber of the nasal patient interface, and a vent wall movable relative to the vent body. The vent wall configured to remain in a closed position while the nasal patient interface is used to provide pressurized air to the patient's nares only. The vent wall configured to move to the open position when the nasal plenum chamber connects to an oral plenum chamber thereby forming an oro-nasal patient interface.

Another aspect of one form of the present technology is a vent structure to allow a continuous flow of gases exhaled by the patient from an interior of the plenum chamber to ambient, said vent structure being sized and shaped to maintain the therapeutic pressure in the nasal plenum chamber in use, and vent structure comprising: a housing secured to the plenum chamber, and a vent wall coupled to the housing and selectively movable between a closed position and an open position, wherein the vent wall is biased toward the closed position, and wherein the vent wall is configured to be positioned in the open position in order to accommodate an oral cushion with an oral plenum chamber and form an oro-nasal cushion.

Another aspect of one form of the present technology is a patient interface comprising: a body comprising: a nasal plenum chamber pressurisable to a therapeutic pressure of at least 4 cmH$_2$O above ambient air pressure, said plenum chamber including at least one plenum chamber inlet port sized and structured to receive a flow of air at the therapeutic pressure for breathing by a patient; a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the nasal plenum chamber throughout the patient's respiratory cycle in use; and a vent structure to allow a continuous flow of gases exhaled by the patient from an interior of the plenum chamber to ambient, said vent structure being sized and shaped to maintain the therapeutic pressure in the nasal plenum chamber in use, and vent structure comprising: a housing (e.g., rigid, semi-rigid, flexible) secured to the plenum chamber, and a vent wall coupled to the housing and selectively movable between a closed position and an open position, wherein the vent wall is biased toward the closed position, and wherein the vent wall is configured to be positioned in the open position in order to accommodate an oral cushion with an oral plenum chamber and form an oro-nasal cushion; and a positioning and stabilising structure to provide a force to hold the seal-forming structure in a therapeutically effective position on the patient's head.

In some forms, a) the vent wall is flexible relative to the housing; b) the housing includes at least one magnet configured to removably connect to the oral cushion; c) the positioning and stabilising structure includes one of more conduits configured to convey the therapeutic pressure to the nasal plenum chamber; d) the positioning and stabilising structure includes a textile strap configured to contact an occipital portion of the patient's head; e) the textile strap including a magnet configured to connect to a lower strap usable with the oral plenum chamber; and/or f) the magnet is laminated to an outer surface of the textile strap.

In some forms, a) the housing is permanently connected to the plenum chamber; b) the vent wall is movable into the plenum chamber in the open position; c) the vent wall includes a plurality of openings configured to vent air in the closed position; and/or d) the housing includes a lip extending at least partially around an inner perimeter, the vent wall configured to seal against the lip in the closed position.

Another aspect of one form of the technology is a patient interface comprising: a mouth plenum pressurisable to a therapeutic pressure of at least 4 cmH2O above ambient air pressure, said mouth plenum including a plenum chamber inlet port sized and structured to receive a flow of air at the therapeutic pressure for breathing by a patient; a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, the seal-forming structure comprising: a mouth portion that forms at least part of the mouth plenum and is configured to seal around the patient's mouth; a nasal portion that is configured to seal with the patient's nares, the nasal portion comprising a nasal plenum positioned to fluidly communicate with the mouth plenum; and a connection body configured to connect the mouth plenum to the nasal plenum and act as a channel for the flow of air between the mouth plenum and the nasal plenum, the connection body comprising: a pair of prongs protruding from a base surface of the connection body, a base of each prong being positioned on opposing lateral sides of the connection body; a positioning and stabilising structure to provide a force to hold the seal-forming structure in a therapeutically effective position on the patient's head; a first vent structure connected to the mouth plenum, the first vent structure configured to allow a continuous flow of gases exhaled by the patient from an interior of the plenum chamber to ambient, said first vent structure being sized and shaped to maintain the therapeutic pressure in the plenum chamber in use; and a second vent structure including a vent body connected to the nasal plenum and a vent wall flexible between an open position and a closed position, wherein the vent wall is biased toward the closed position and wherein the vent wall is configured to move (e.g., flex or bend) toward the open position when contacted by the pair of nasal prongs.

In some forms, a) the nasal portion comprises a flexible base and a pair of nasal pillows attached to the flexible base, the nasal pillows being configured to seal with an interior of the patient's nostrils; b) the mouth plenum is partly formed by a shell, which has a shell inside surface and shell outside surface; c) the shell inside surface is arranged to be at said therapeutic pressure in use, and said shell outside surface is arranged to be at ambient pressure in use; d) the shell is structured to be when subject to an internal pressure of less than about 30 cmH2O above ambient pressure; e) the shell is constructed from a hard plastic material; f) the shell is constructed from a transparent material; and/or g) the shell inside surface is constructed to include a concave dome-shaped region.

In some forms, a) the mouth plenum includes a receptacle configured to receive the nasal plenum; b) the receptacle includes a curved shape configured to correspond to the shape of the nasal plenum; c) the connecting body is permanently connected to the mouth plenum; and/or d) the second vent structure is permanently connected to the nasal plenum.

In some forms, a) the pair of prongs are constructed from a rigid or semi-rigid material; b) the distance between the pair of prongs is less than the maximum dimension of the vent wall; c) the vent wall is configured to seal against the vent body in the closed position, and wherein the vent wall includes a plurality of vent openings; d) the vent body includes a first planar surface and the base surface of the connection body includes a second planar surface configured to interface with the first planar surface; e) the connection body includes a first connection member and the vent body includes a second connection member; f) the first connection member and the second connection member are configured to removably connect to one another; g) the first connection member and the second connection member are magnets; and/or h) the first connection member and the second connection member are mechanical connections configured to snap fit to one another.

In some forms, a) the nasal plenum includes a first inlet and a second inlet; b) the positioning and stabilising structure includes conduit headgear connected to the first inlet and the second inlet; and/or c) the conduit headgear includes an extendible portion configured to stretch when donned by the user.

In some forms, a) the positioning and stabilising structure includes a first headgear strap connected to the mouth plenum and a second headgear strap connected to the nasal plenum; b) the first headgear strap is removably connected to the mouth plenum, the second headgear connector is removably connected to the nasal plenum, and the first headgear strap and the second headgear strap are removably connected to each other; c) the first headgear strap and the second headgear strap are magnetically connectable to one another; d) magnets are laminated to each of the first headgear strap and the second headgear strap; e) the first headgear connector and the second headgear connector are connectable with hook and loop material; f) the first headgear strap includes a rear portion configured to overlay the occipital bone of the user's head; g) the rear portion includes an upper portion with a bend that is out of plane with the remainder of the rear portion; h) when connected the bend in the rear portion is configured to connect to the second headgear connector; i) the first headgear strap and the second headgear strap each include an inner foam layer and a pair of outer fabric layers at least partially covering the foam layer; and/or j) the second headgear strap includes a bifurcated portion configured to contact a posterior portion of the user's head.

In some forms, a) the flow of air is configured to first enter the nasal portion and travel to the mouth portion via the connection body while the vent body is in the open position; b) the nasal portion is separable from the mouth portion and usable to deliver the flow of air to the patient independently of the mouth portion; and/or c) the vent wall is in the closed position and is configured to allow a continuous flow of gases exhaled by the patient from an interior of the plenum chamber to ambient.

Another aspect of one form of the present technology is a patient interface comprising: a nasal plenum pressurisable to a therapeutic pressure of at least 4 cmH2O above ambient air pressure, said mouth plenum including a plenum chamber inlet port sized and structured to receive a flow of air at the therapeutic pressure for breathing by a patient; a mouth plenum pressurisable to a therapeutic pressure of at least 4 cmH2O above ambient air pressure, said mouth plenum structured to receive the flow of air at the therapeutic pressure for breathing by a patient; a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, the seal-forming structure comprising; a mouth portion that forms at least part of the mouth plenum and is configured to seal around the patient's mouth; a nasal portion that is configured to seal with the patient's nares, the nasal portion comprising the nasal plenum positioned to fluidly communicate with the mouth plenum; and a connection body connected to the mouth plenum and configured to form a sealed connection with the nasal plenum, the connection body comprising: at least one prong protruding from a base surface of the connection body; a positioning and stabilising structure to provide a force to hold the seal-forming structure in a therapeutically effective position on the patient's head; a first vent structure connected to the mouth plenum, the first vent structure configured to allow a continuous flow of gases exhaled by the patient from an interior of the plenum chamber to ambient, said first vent structure being sized and shaped to maintain the therapeutic pressure in the plenum chamber in use; and a second vent structure including a vent body connected to the nasal plenum and a vent wall flexible between an open position and a closed position, wherein the vent wall is configured to flex toward the open position when contacted by the pair of nasal prongs.

In some forms, a) the vent wall is biased toward the closed position; b) the positioning and stabilising structure includes conduit headgear connected to the inlet port of the nasal plenum; c) the conduit headgear configured to convey the flow of air to the nasal plenum; d) the positioning and stabilising structure includes a first strap and a second strap, the first strap is configured to provide a first force to hold the nasal portion in the therapeutically effective position, and the second strap is configured to provide a second force to hold the mouth portion in a therapeutically effective position; and/or e) the first strap and the second strap are removably connected to one another.

In some forms, a) the connection body includes a planar surface radially outside of the at least one prong; b) the planar surface is configured to contact a complementary surface of the second vent structure; c) the planar surface includes a first connector configured to removably engage with a second connector of the complementary surface.

In some forms, a) the at least one prong is a first prong and a second prong; b) the first prong and the second prong are spaced apart from one another around the perimeter of the connection body; c) the nasal portion is separable from the mouth portion and usable to deliver the flow of air to the patient independently of the mouth portion; and/or d) the vent wall is in the closed position and is configured to allow a continuous flow of gases exhaled by the patient from an interior of the plenum chamber to ambient.

Another aspect of one form of the present technology is a patient interface comprising a nasal cushion having a nasal plenum chamber and a first vent, the first vent including a vent wall having a plurality of holes, the vent wall being movable between an open position and a closed position; wherein in the closed position, airflow is configured to pass through the plurality of holes; and wherein in the closed position, the nasal plenum chamber is configured to be connected to an oral cushion that maintains the vent wall in the open position so that airflow may pass around the vent wall without passing through the vent holes.

Another aspect of one form of the present technology is a patient interface comprising: a nasal plenum pressurisable to a therapeutic pressure of at least 4 cmH2O above ambient air pressure, said nasal plenum including a plenum chamber inlet port sized and structured to receive a flow of air at the therapeutic pressure for breathing by a patient; a mouth plenum pressurisable to a therapeutic pressure of at least 4 cmH2O above ambient air pressure, said mouth plenum structured to receive the flow of air at the therapeutic pressure for breathing by a patient; a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, the seal-forming structure comprising; a mouth portion that forms at least part of the mouth plenum and is configured to seal around the patient's mouth; a nasal portion that is configured to seal with the patient's nares, the nasal portion comprising the nasal plenum positioned to fluidly communicate with the mouth plenum; and a positioning and stabilising structure to provide a force to hold the seal-forming structure in a therapeutically effective position on the patient's head; a first vent structure connected to the mouth plenum, the first vent structure configured to allow a continuous flow of gases exhaled by the patient from an interior of the mouth plenum to ambient, said first vent structure being sized and shaped to maintain the therapeutic pressure in the mouth plenum in use; and a second vent structure connected to the nasal plenum, the second vent structure configured to allow a continuous flow of gases exhaled by the patient from an interior of the plenum chamber to ambient, said first vent structure being sized and shaped to maintain the therapeutic pressure in the plenum chamber in use; wherein in use, the first vent structure is maintained in a functional position and allows the continuous flow of air to pass through a body of the first vent structure to the ambient; and wherein in use, the second vent structure is maintained in a non-functional position and allows the continuous flow of air to pass around a body of the second vent structure.

In some forms, a) the second vent structure is movable between a closed position and the non-functional position; b) the second vent structure is biased toward the closed position; c) the second vent structure includes a vent wall bendable between the closed position and the non-functional position; d) the second vent structure includes a plurality of holes configured to allow the continuous flow of air to pass through in the closed position; e) the mouth plenum is configured to maintain the second vent structure in the non-functional position; f) the mouth plenum includes a connection body configured to form a sealed connection with the nasal plenum; g) the connection body comprising at least one prong protruding from a base surface of the connection body; h) the at least one prong is configured to maintain the second vent structure in the non-functional position; i) the connection body includes a planar surface radially outside of the at least one prong; j) the planar surface is configured to contact a complementary surface of the second vent structure; k) the planar surface includes a first connector configured to removably engage with a second connector of the complementary surface; and/or 1) the at least one prong is a first prong and a second prong, and wherein the first prong and the second prong are spaced apart from one another around the perimeter of the connection body.

In some forms, a) the positioning and stabilising structure includes conduit headgear connected to the inlet port of the nasal plenum; b) the conduit headgear configured to convey the flow of air to the nasal plenum; c) the second vent structure in the non-functional position is configured to allow the flow of air conveyed by the conduit headgear to pass from the nasal plenum to the mouth plenum; d) the positioning and stabilising structure includes a first strap and a second strap, the first strap is configured to provide a first force to hold the nasal portion in the therapeutically effective position, and the second strap is configured to provide a second force to hold the mouth portion in a therapeutically effective position; e) the first strap and the second strap are removably connected to one another; and/or f) the nasal portion is separable from the mouth portion and usable to deliver the flow of air to the patient independently of the mouth portion.

Another aspect of one form of the present technology is a patient interface comprising: a body comprising a mouth plenum chamber pressurisable to a therapeutic pressure of at least 4 cmH$_2$O above ambient air pressure, said mouth plenum chamber including at least one plenum chamber inlet port sized and structured to receive a flow of air at the therapeutic pressure for breathing by a patient; a seal-forming structure constructed and arranged to form a seal with a region of the patient's face surrounding an entrance to the patient's mouth, said seal-forming structure having a hole therein such that the flow of air at said therapeutic pressure is delivered to at least an entrance to the patient's mouth, the seal-forming structure constructed and arranged to maintain said therapeutic pressure in the nasal plenum chamber throughout the patient's respiratory cycle in use; and a vent structure to allow a continuous flow of gases exhaled by the patient from an interior of the plenum chamber to ambient, said vent structure being sized and shaped to maintain the therapeutic pressure in the nasal plenum chamber in use; a connection body disposed in the plenum chamber inlet port and configured to connect the mouth plenum to a nasal plenum and act as a channel for the flow of air between the mouth plenum and the nasal plenum, the connection body comprising: a pair of prongs protruding from a base surface of the connection body, a base of each prong being positioned on opposing lateral sides of the connection body; a positioning and stabilising structure to provide a force to hold the seal-forming structure in a therapeutically effective position on the patient's head; wherein the pair of nasal prongs are configured to engage a nasal vent connected to the nasal plenum chamber and move the nasal vent to an open position to facilitate fluid communication through the plenum chamber inlet port.

In some forms, a) the positioning and stabilising structure includes a textile strap configured to contact an occipital portion of the patient's head; b) the textile strap including a magnet configured to connect to a lower strap usable with the oral plenum chamber; and/or c) the magnet is laminated to an outer surface of the textile strap.

In some forms, a) the connection body is permanently connected to the mouth plenum chamber; b) the connection body is rigid; c) connection body is positioned within a receptacle of the mouth plenum chamber; d) the receptacle is configured to removably receive the nasal plenum chamber; e) the receptacle includes a curved surface; f) each prong includes an inner flat surface and an outer curved surface; g) each prong is at least partially resilient and configured to form a snap fit connection with the nasal plenum; and/or h) the mouth portion is separable from the nasal portion and usable to deliver the flow of air to the patient independently of the mouth portion.

Another aspect of one form of the present technology is a patient interface that is moulded or otherwise constructed with a perimeter shape which is complementary to that of an intended wearer.

An aspect of one form of the present technology is a method of manufacturing apparatus.

Another aspect of one form of the present technology is a method of assembling a modular patient interface, the method comprising: providing a nasal patient interface comprising: a nasal plenum chamber pressurisable to a therapeutic pressure of at least 4 cmH$_2$O above ambient air pressure, a nasal seal forming structure configured to seal with the patient's nares, a vent structure including a vent body connected to the nasal plenum chamber and a vent wall connected to the vent body and movable between a closed position and an open position, and a first positioning and stabilising structure configured to provide a tensile force for holding the nasal seal forming structure in an operative position; providing an oral cushion comprising: an oral plenum chamber pressurisable to a therapeutic pressure of at least 4 cmH$_2$O above ambient air pressure, an oral seal forming structure configured to seal with the patient's mouth, a receptacle disposed outside of the oral plenum chamber and spaced apart from the oral seal forming structure, the receptacle comprising, a receptacle opening providing fluid communication with the oral plenum chamber, and at least one prong disposed around at least a portion of the perimeter of the receptacle opening; a second positioning and stabilising structure configured to provide a tensile force for holding the nasal seal forming structure in the operative position; and positioning the nasal patient interface in the receptacle and aligning the vent structure with the receptacle opening; inserting the at least one prong into the nasal plenum chamber by moving the vent wall to an open position; connecting the nasal patient interface to the oral cushion so that the nasal plenum chamber and the oral plenum chamber are connected to one another in an air tight configuration; and connecting the first positioning and stabilising structure to the second positioning and stabilising structure.

In some forms, a) connecting an air delivery tube to the nasal plenum chamber; b) the air delivery tube is configured to delivery pressurised air to the nasal plenum chamber; c) the air delivery tube is configured to deliver the pressurised air to the oral plenum chamber when the at least one prong is inserted into the oral plenum chamber; and/or d) the air delivery tube is conduit headgear and forms at least part of the first positioning and stabilising structure.

In some forms, a) a surface in the receptacle includes a first magnet and the vent body includes a second magnet; and/or b) connecting the nasal patient interface to the oral cushion is accomplished using a magnet connection.

In some forms, a) a surface in the receptacle includes a first mechanical connector and the vent body includes a second mechanical connector; and/or b) connecting the nasal patient interface to the oral cushion is accomplished using a removable snap fit connection.

In some forms, a) the first positioning and stabilising structure includes a strap with a third magnet; b) the second positioning and stabilising structure includes a strap with a fourth magnet; and/or c) connecting the first positioning and stabilising structure to the second positioning and stabilising structure is accomplished using a magnetic connection.

In some forms, a) disconnecting the nasal patient interface from the oral cushion and using the nasal patient cushion independently to deliver pressurised air to the patient; and/or b) the vent wall returns to the closed position and seals against the vent body.

In some forms, a) flexing the vent wall toward the nasal seal forming structure after inserting the at least one prong into the nasal plenum chamber; and/or b) the vent body is permanently connected to the nasal plenum chamber.

Another aspect of one form of the present technology is a method of assembling a modular patient interface, the method comprising: providing a nasal patient interface comprising a first vent structure; providing an oral cushion comprising a second vent structure; using the nasal patient interface independently of the oral cushion and maintaining the first vent in a functional position to exhaust air from a nasal plenum chamber to ambient; and connecting the nasal patient interface to the oral cushion so that the nasal plenum chamber is fluidly connected to an oral plenum chamber; wherein the first vent is maintained in a non-functional position and the second vent is maintained in a functional position when the nasal patient interface is connected to the oral cushion.

In some forms, the first vent is movable (e.g., flexible, pivotable, translatable, etc.) between the functional position and the non-functional position. In some forms, the first vent is configured to allow airflow pass through in either the functional or the non-functional position. For example, airflow may pass through vent holes in the functional position and airflow may pass around the outside of the vent in the non-functional position.

Another aspect of one form of the present technology is a method of assembling a modular patient interface, the method comprising: providing a nasal patient interface comprising: a nasal seal; and a nasal vent structured to move between a closed position and an open position; and providing an oral plenum chamber comprising: an oral seal, a receptacle disposed outside of the oral plenum chamber and spaced apart from the oral seal forming structure, the receptacle comprising, a receptacle opening providing fluid communication with the oral plenum chamber, and at least one prong disposed around at least a portion of the perimeter of the receptacle opening; positioning the nasal patient interface in the receptacle and aligning the nasal vent with the receptacle opening; and inserting the at least one prong into the nasal plenum chamber to move the vent wall to an open position.

In some forms, a) further comprising connecting an air delivery tube to the nasal plenum chamber, the air delivery tube is configured to delivery pressurised air to the nasal plenum chamber, and wherein the air delivery tube is configured to deliver the pressurised air to the oral plenum chamber when the at least one prong is inserted into the oral plenum chamber; and/or b) the air delivery tube is conduit headgear and forms at least part of a first positioning and stabilising structure configured to maintain the nasal plenum chamber in an operational position.

In some forms, a) a surface in the receptacle includes a first magnet and the nasal vent includes a second magnet, and wherein connecting the nasal plenum chamber to the oral plenum chamber is accomplished using a magnet connection; b) a surface in the receptacle includes a first mechanical connector and the nasal vent includes a second mechanical connector, and wherein connecting the nasal plenum chamber to the oral plenum chamber is accomplished using a removable snap fit connection; and/or c) a first positioning and stabilising structure includes a strap with a third magnet and a second positioning and stabilising structure includes a strap with a fourth magnet, and wherein connecting the first positioning and stabilising structure to the second positioning and stabilising structure is accomplished using a magnetic connection, the first positioning and stabilising structure and the second positioning and stabilising structure each configured to provide a tensile force to maintain the nasal plenum chamber and the oral plenum chamber in an operational position.

In some forms, a) disconnecting the nasal plenum chamber from the oral plenum chamber and using the nasal plenum chamber independently to deliver pressurised air to the patient; b) the nasal vent returns to a closed position configured to limit air from flowing around the vent; c) the nasal vent is permanently connected to the nasal plenum chamber; and/or d) the oral plenum chamber includes an oral vent configured to remain in a functional position while the nasal vent moves to the open position.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
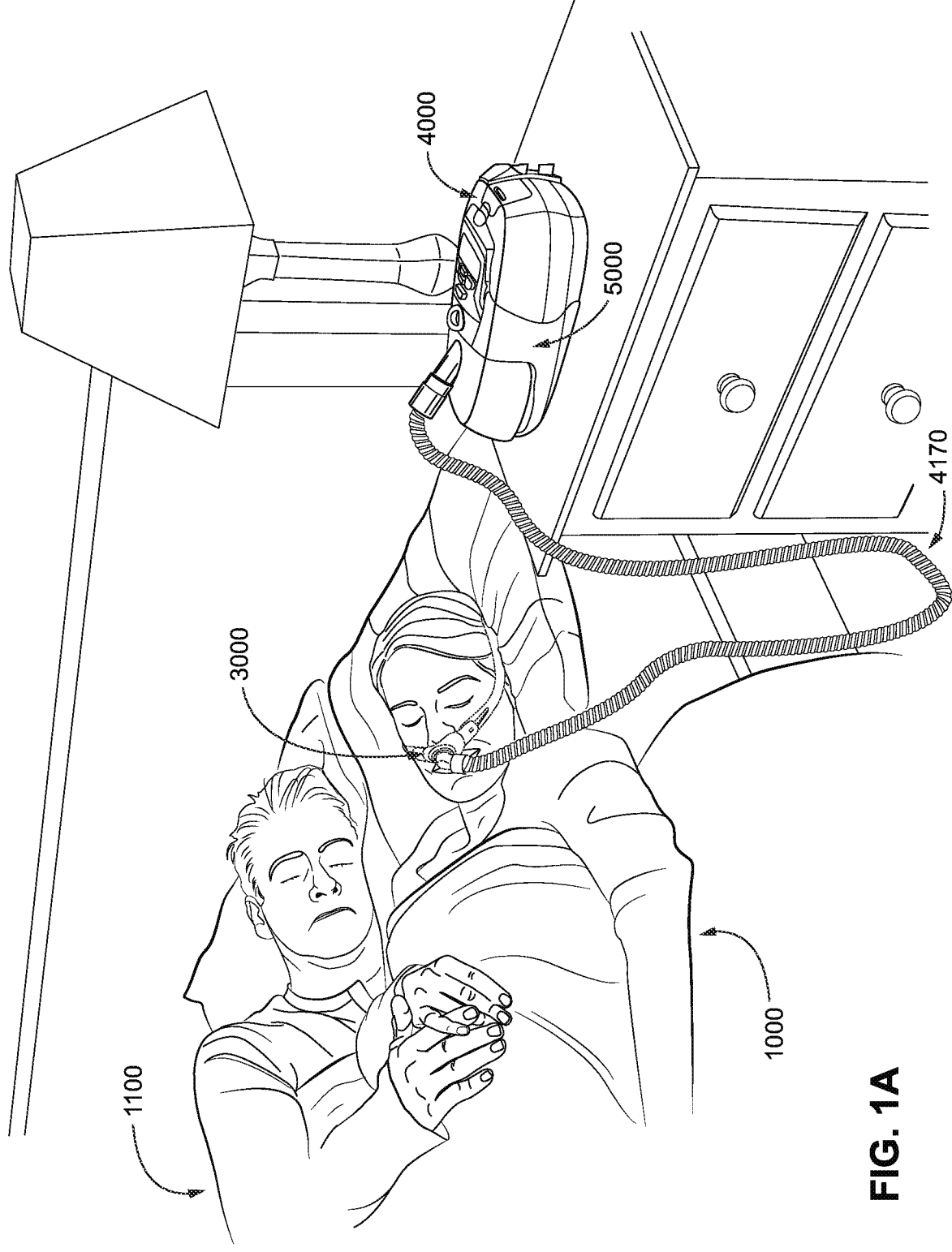
Figure 1B:
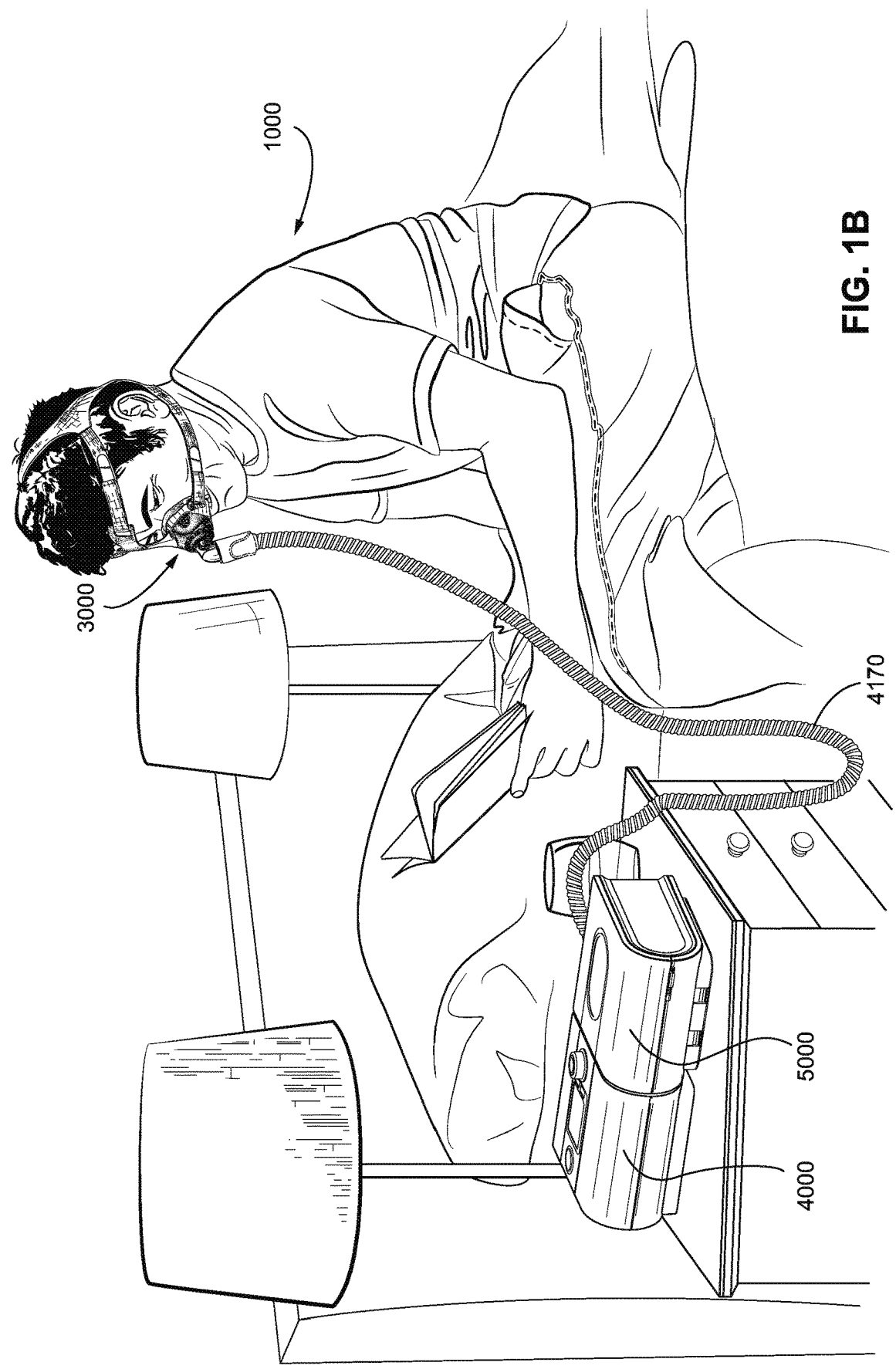
Figure 1C:
Figure 2A:
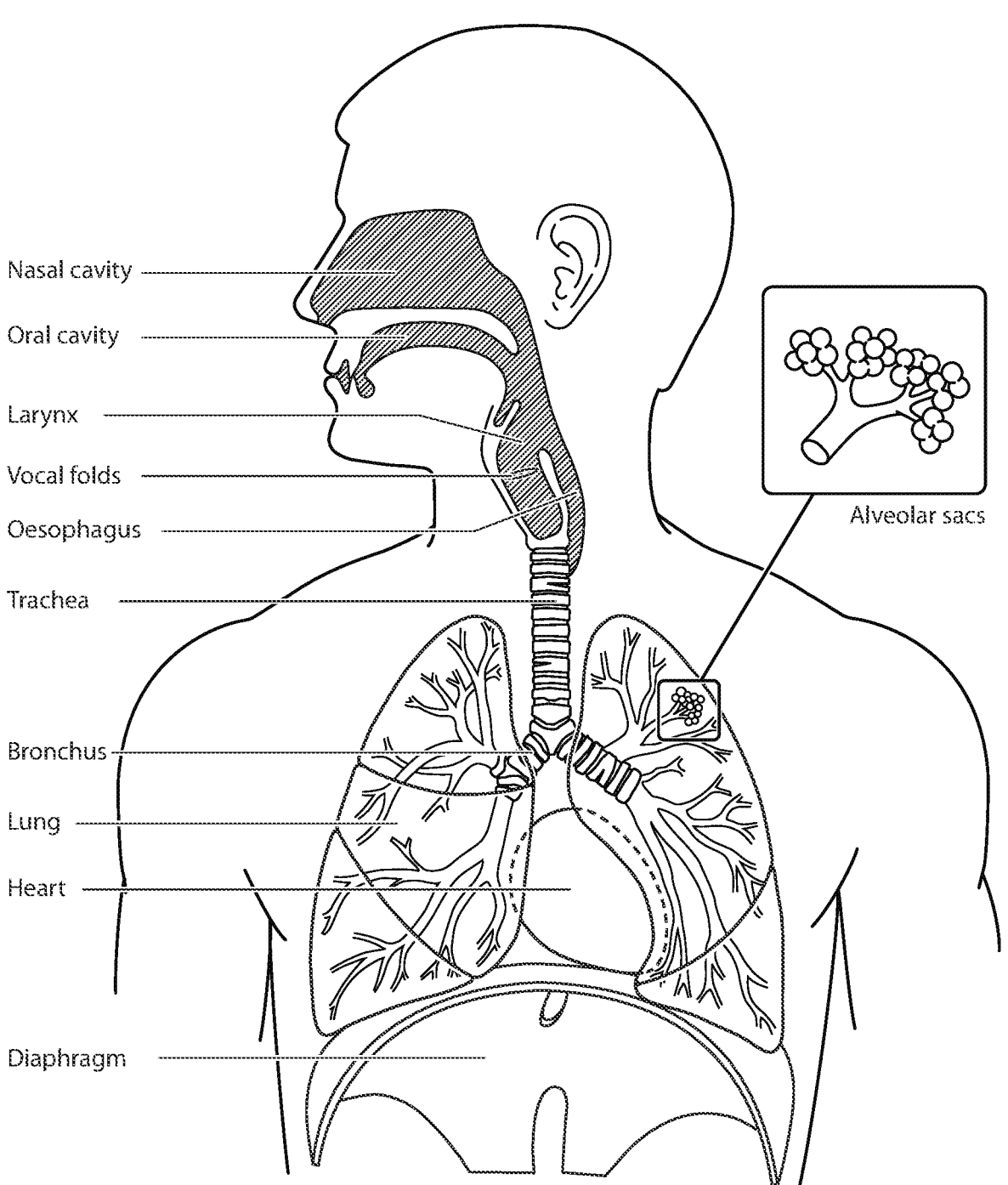
FIG. 2A shows an overview of a human respiratory system including the nasal and oral cavities, the larynx, vocal folds, oesophagus, trachea, bronchus, lung, alveolar sacs, heart and diaphragm.
Figure 2B:
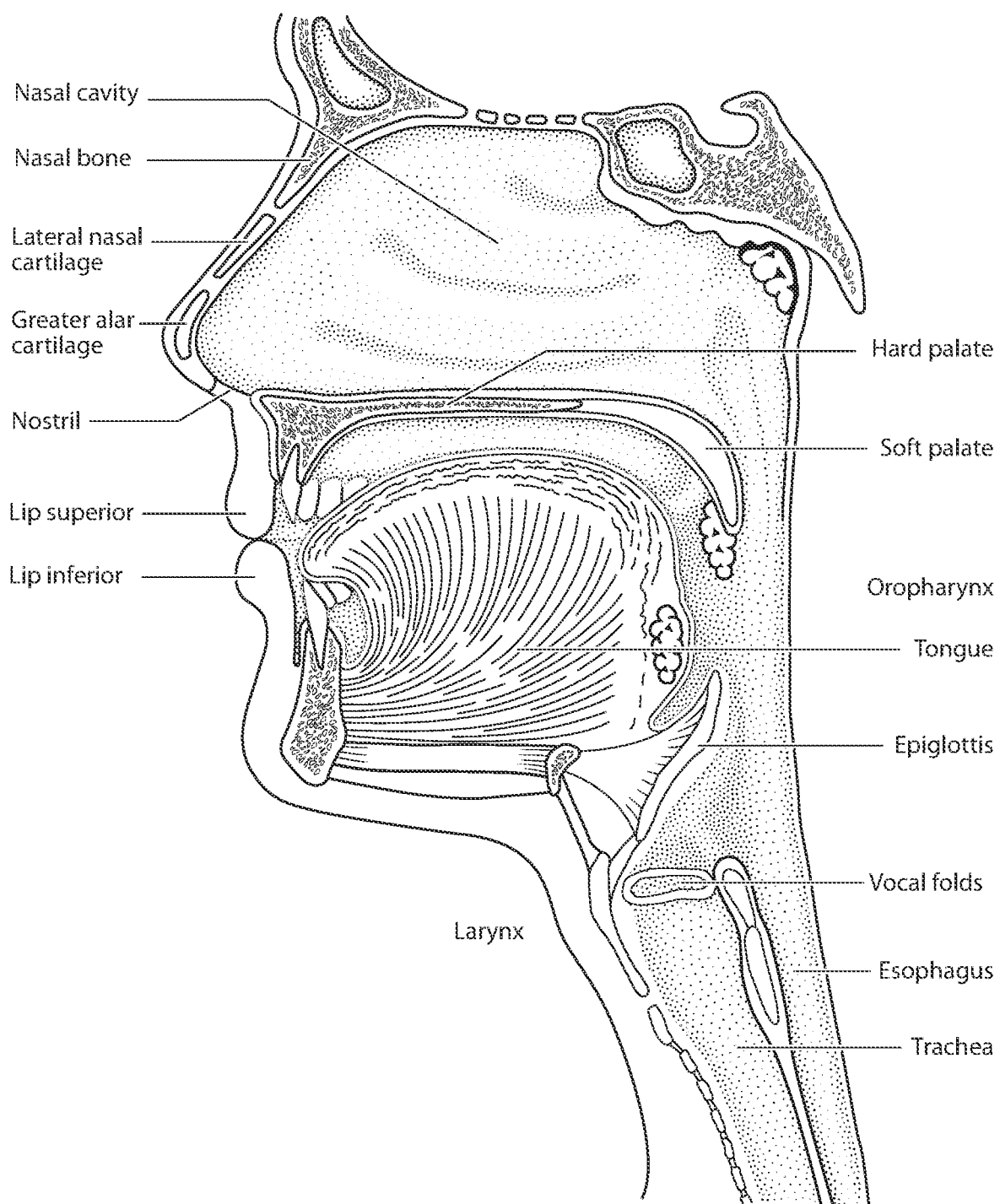
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
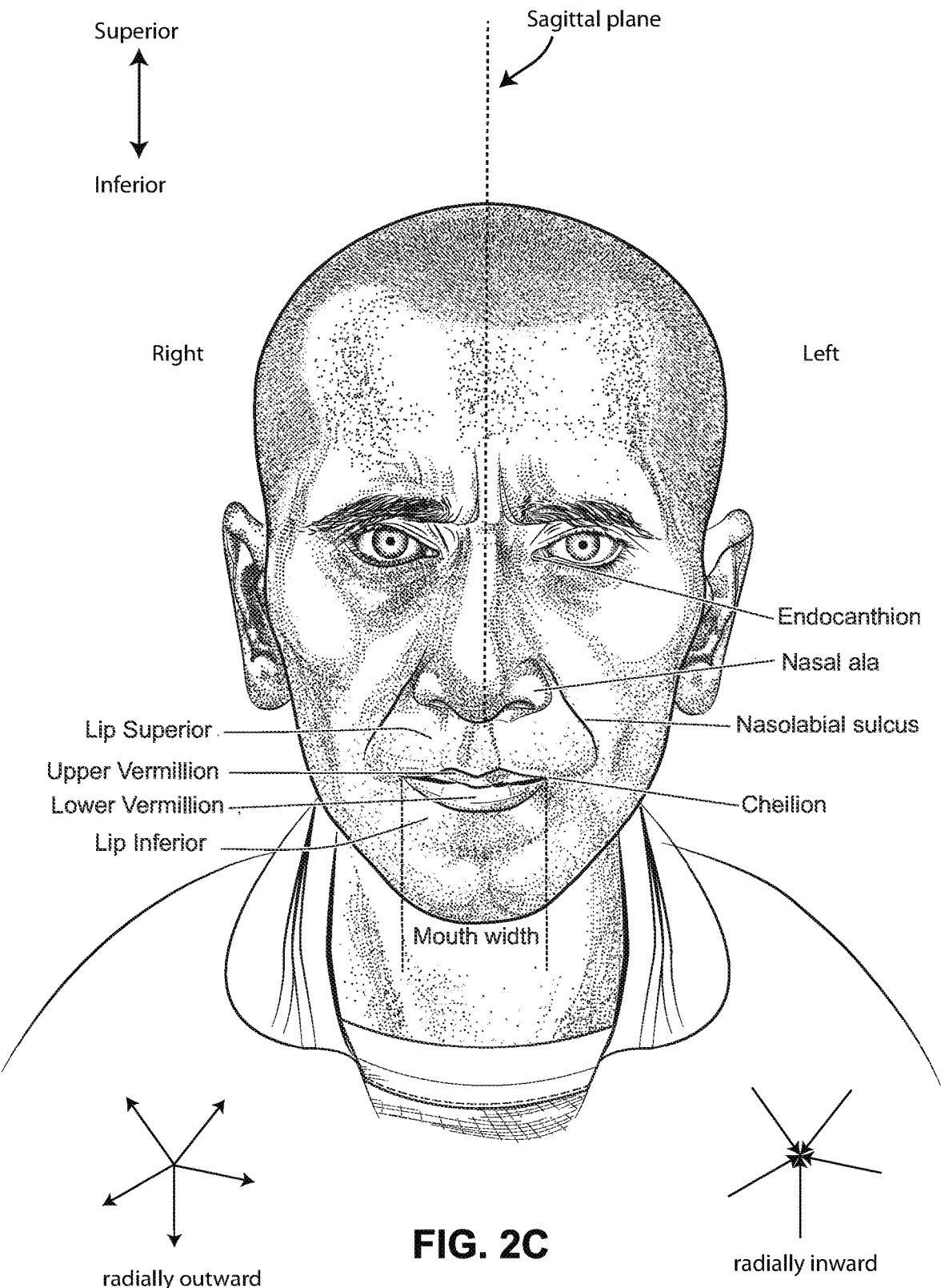
FIG. 2C is a front view of a face with several features of surface anatomy identified including the lip superior, upper vermilion, lower vermilion, lip inferior, mouth width, endo-canthion, a nasal ala, nasolabial sulcus and cheilion. Also indicated are the directions superior, inferior, radially inward and radially outward.
Figure 2D:
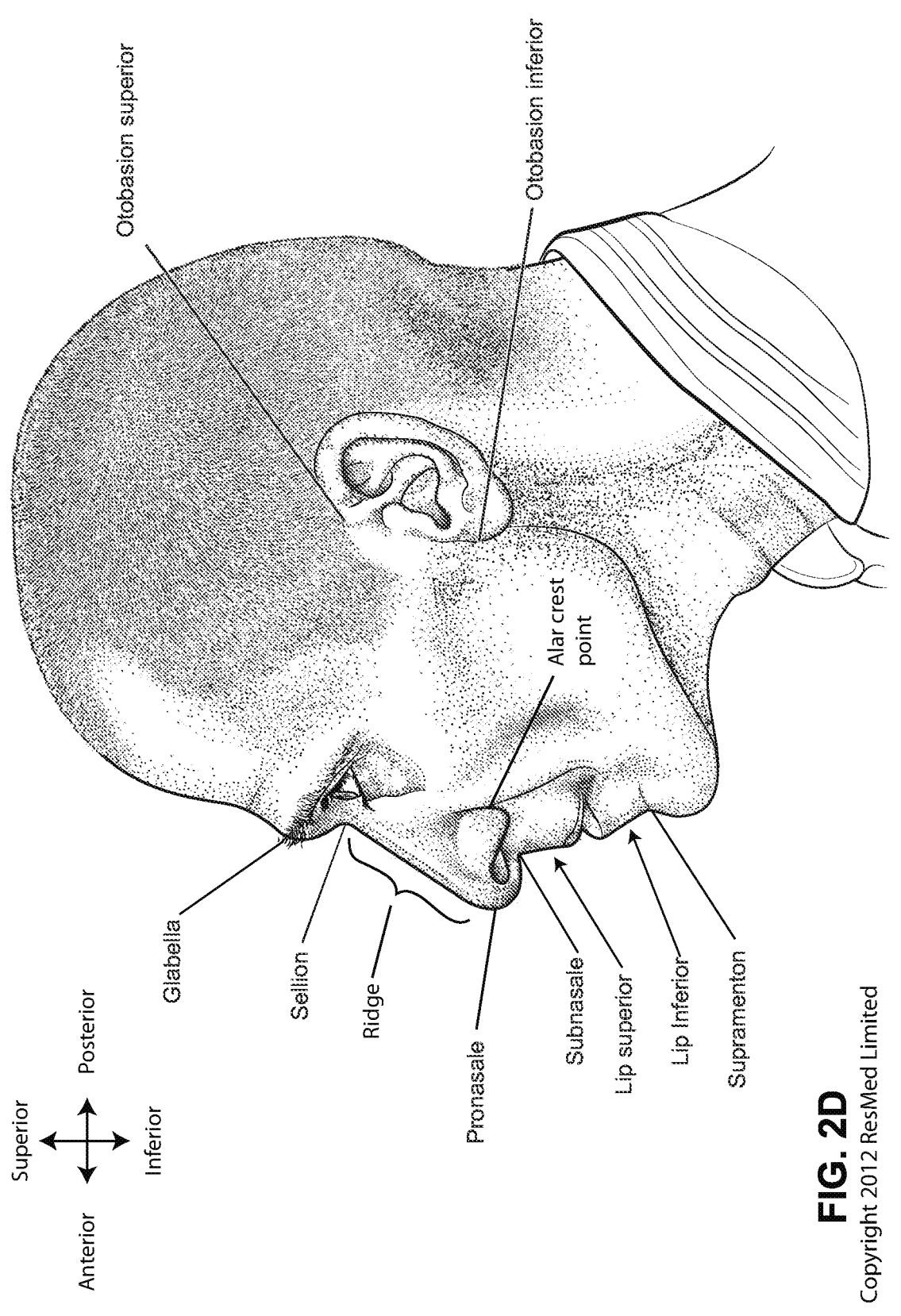
FIG. 2D is a side view of a head with several features of surface anatomy identified including glabella, sellion, pro-nasale, subnasale, lip superior, lip inferior, supramenton, nasal ridge, alar crest point, otobasion superior and otoba-sion inferior. Also indicated are the directions superior & inferior, and anterior & posterior.
Figure 2E:
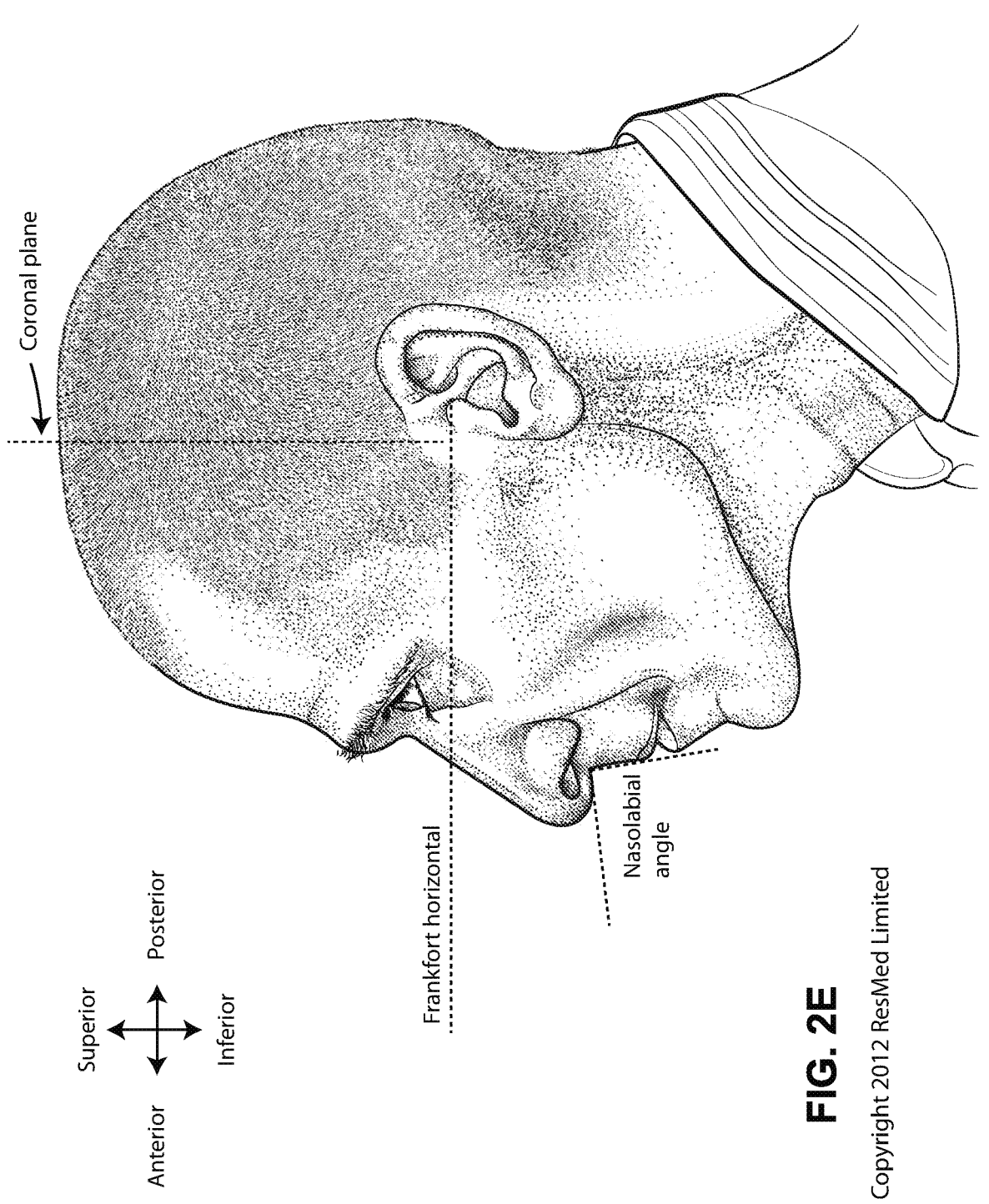

FIG. 2E is a further side view of a head. The approximate locations of the Frankfort horizontal and nasolabial angle are indicated. The coronal plane is also indicated.

Figure 2F:
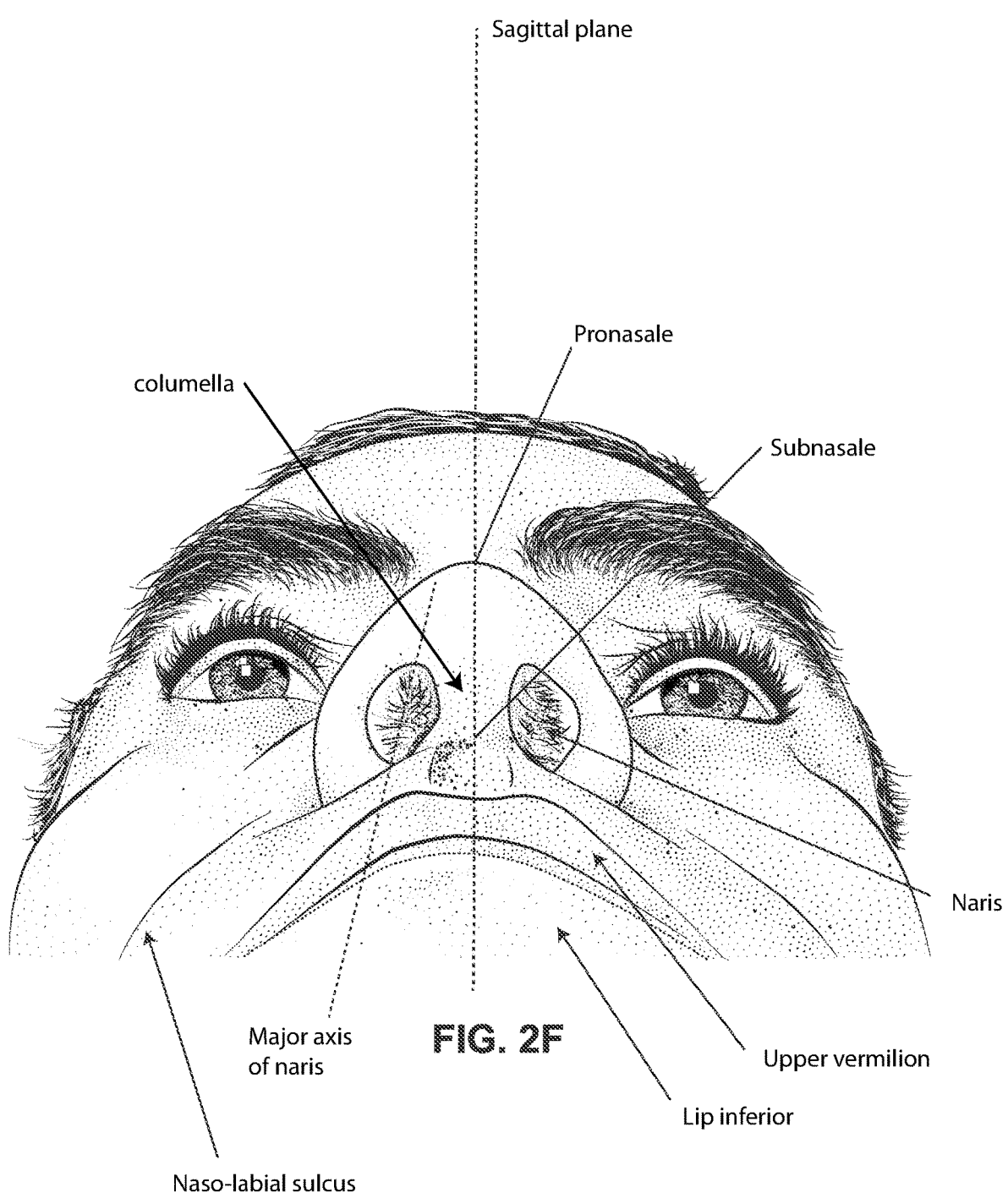

FIG. 2F shows a base view of a nose with several features identified including naso-labial sulcus, lip inferior, upper Vermilion, naris, subnasale, columella, pronasale, the major axis of a naris and the midsagittal plane.

Figures 2G, 2H, 2I:
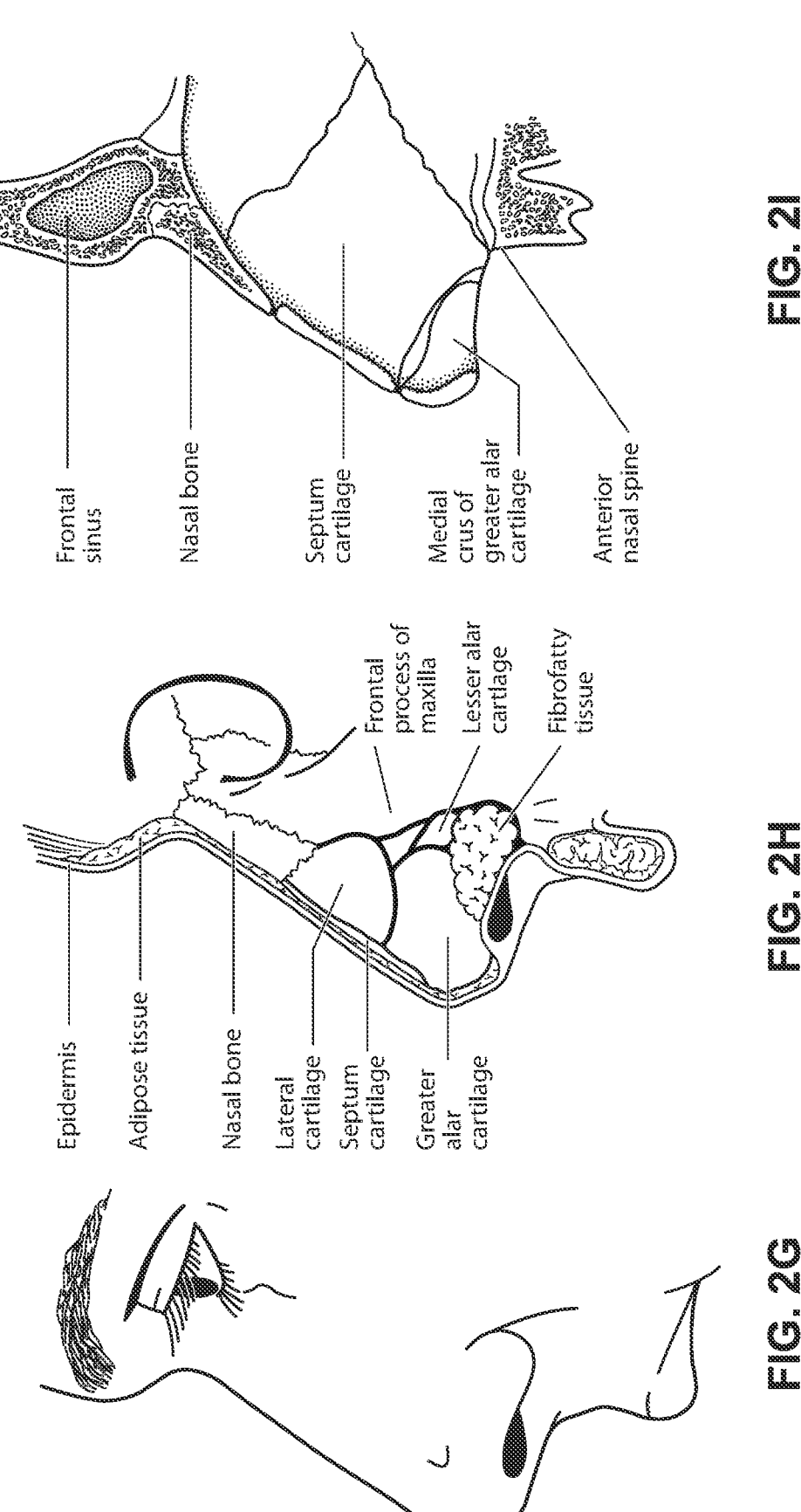

FIG. 2G shows a side view of the superficial features of a nose.

FIG. 2H shows subcutaneal structures of the nose, includ-ing lateral cartilage, septum cartilage, greater alar cartilage, lesser alar cartilage, sesamoid cartilage, nasal bone, epider-mis, adipose tissue, frontal process of the maxilla and fibrofatty tissue.

FIG. 2I shows a medial dissection of a nose, approxi-mately several millimeters from the midsagittal plane, amongst other things showing the septum cartilage and medial crus of greater alar cartilage.

Figures 2J, 2K:
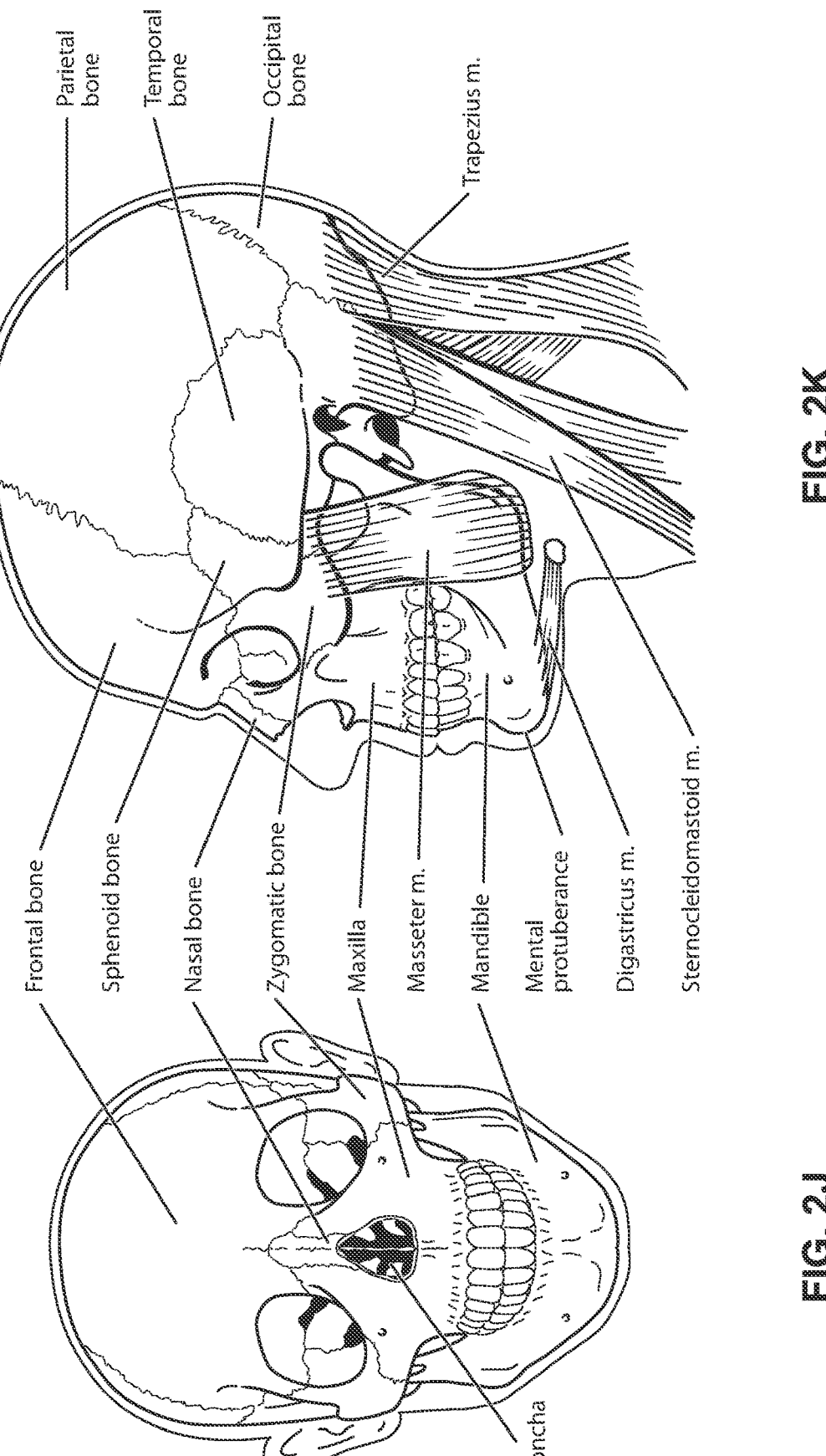

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipi-tal. The mental protuberance is indicated. The following muscles are shown: digastricus, masseter, sternocleidomas-toid and trapezius.

Figure 2L:
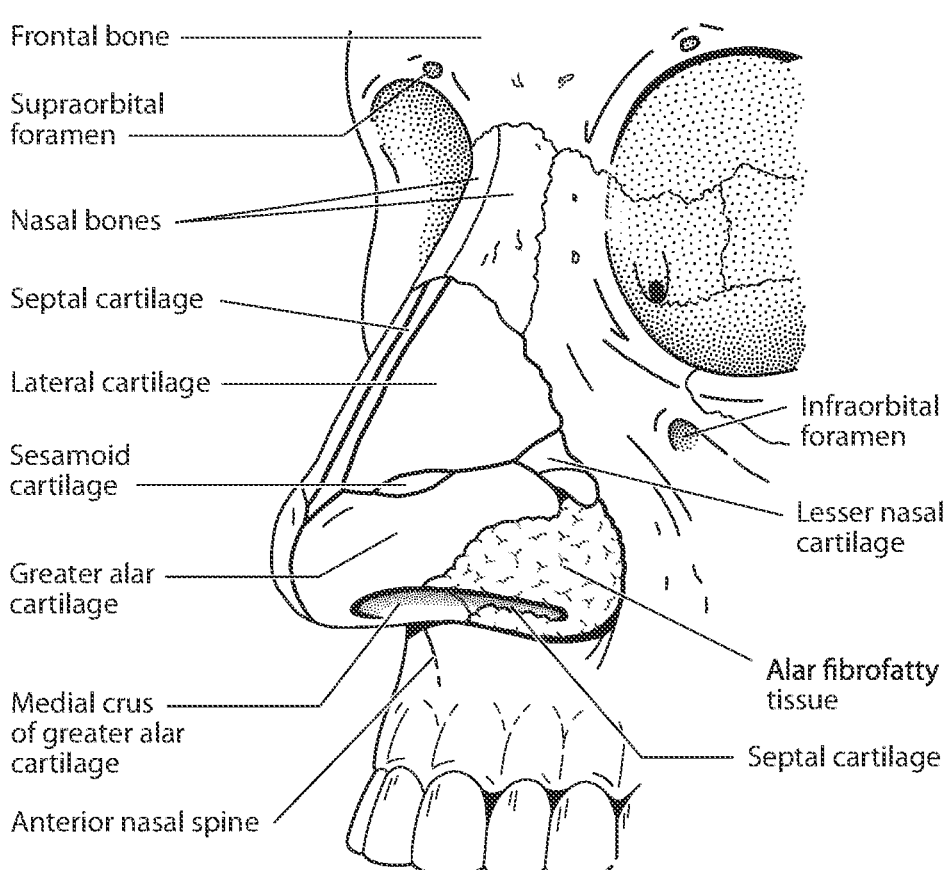

FIG. 2L shows an anterolateral view of a nose.

4.3 Patient Interface

Figure 3A:
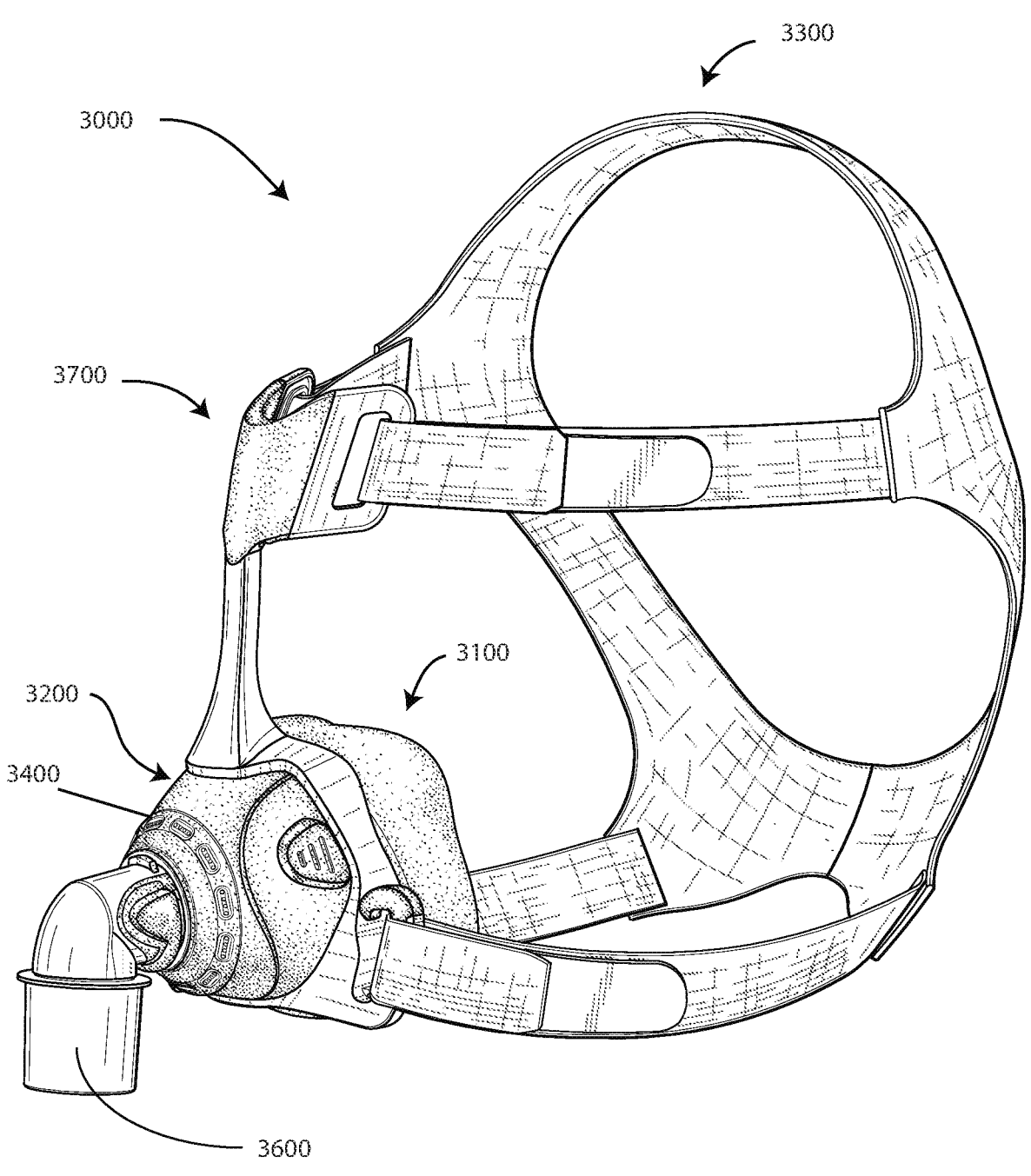

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magni-tude of the curvature shown in FIG. 3C.

FIG. 3C shows a schematic of a cross-section through a structure at a point. An outward normal at the point is indicated. The curvature at the point has a positive sign, and a relatively small magnitude when compared to the magni-tude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magni-tude of the curvature shown in FIG. 3F.

FIG. 3F shows a schematic of a cross-section through a structure at a point. An outward normal at the point is indicated. The curvature at the point has a negative sign, and a relatively large magnitude when compared to the magni-tude of the curvature shown in FIG. 3E.

Figures 3G, 3H:
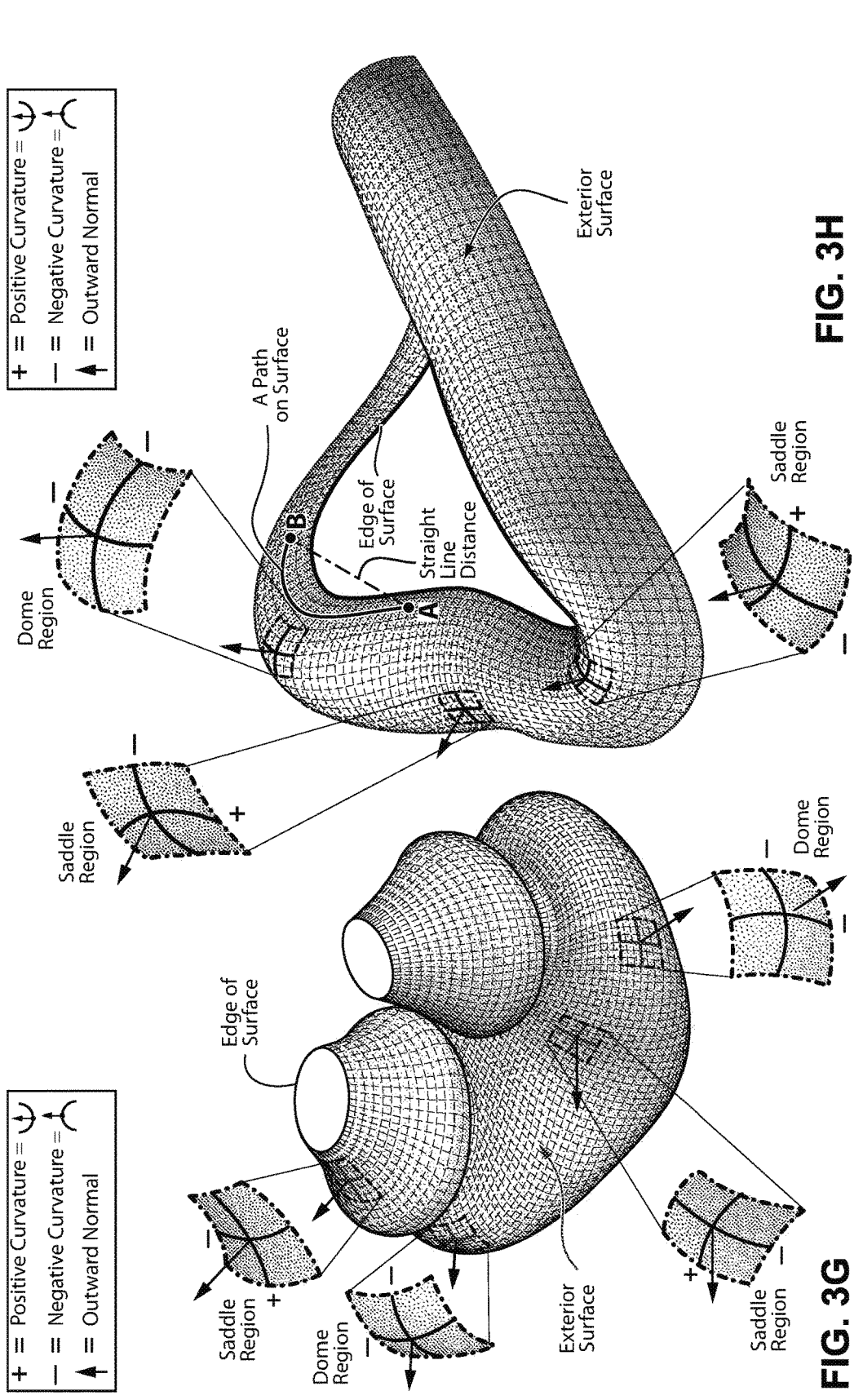

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indi-cated.

Figures 3I, 3J, 3K, 3L, 3M, 3N:
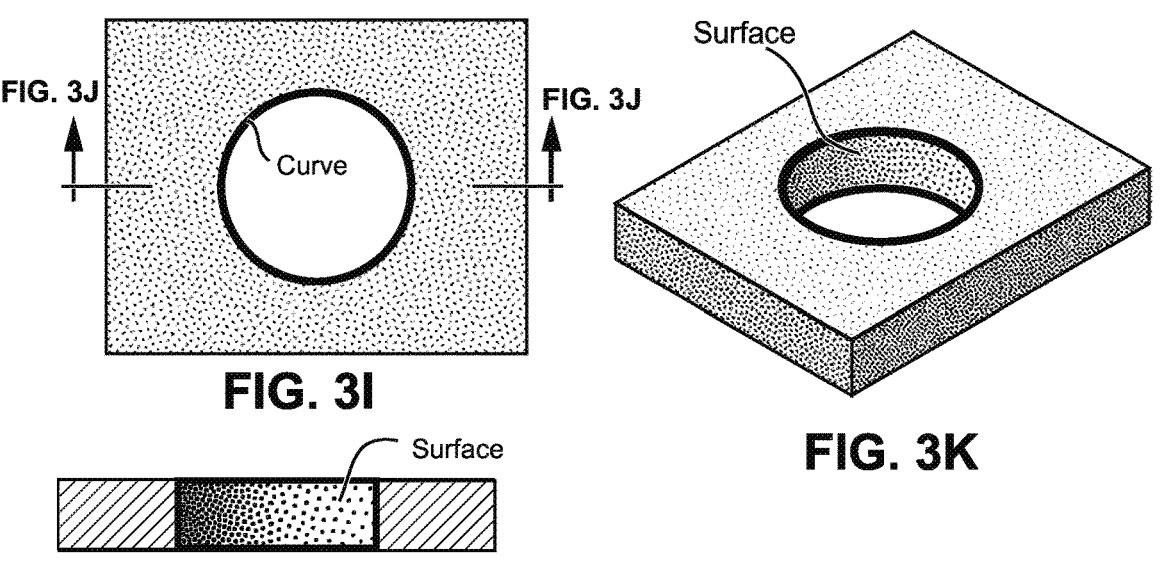

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimen-sional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figures 3U, 3V, 3W, 3X:
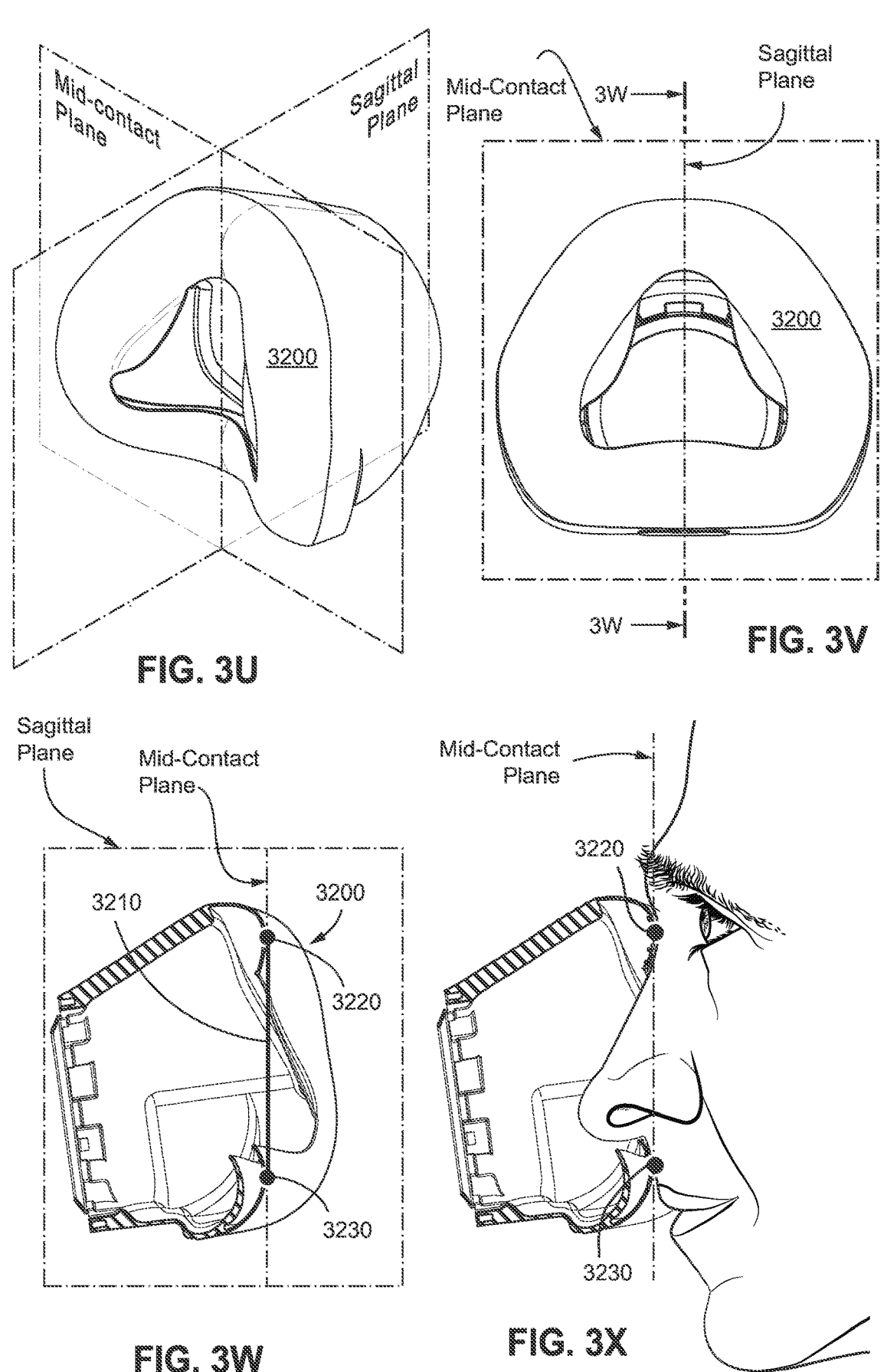

FIG. 3U shows a view of a plenum chamber 3200 showing a sagittal plane and a mid-contact plane.

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

FIG. 3W shows a cross-section through the plenum cham-ber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 RPT Device

Figure 4A:
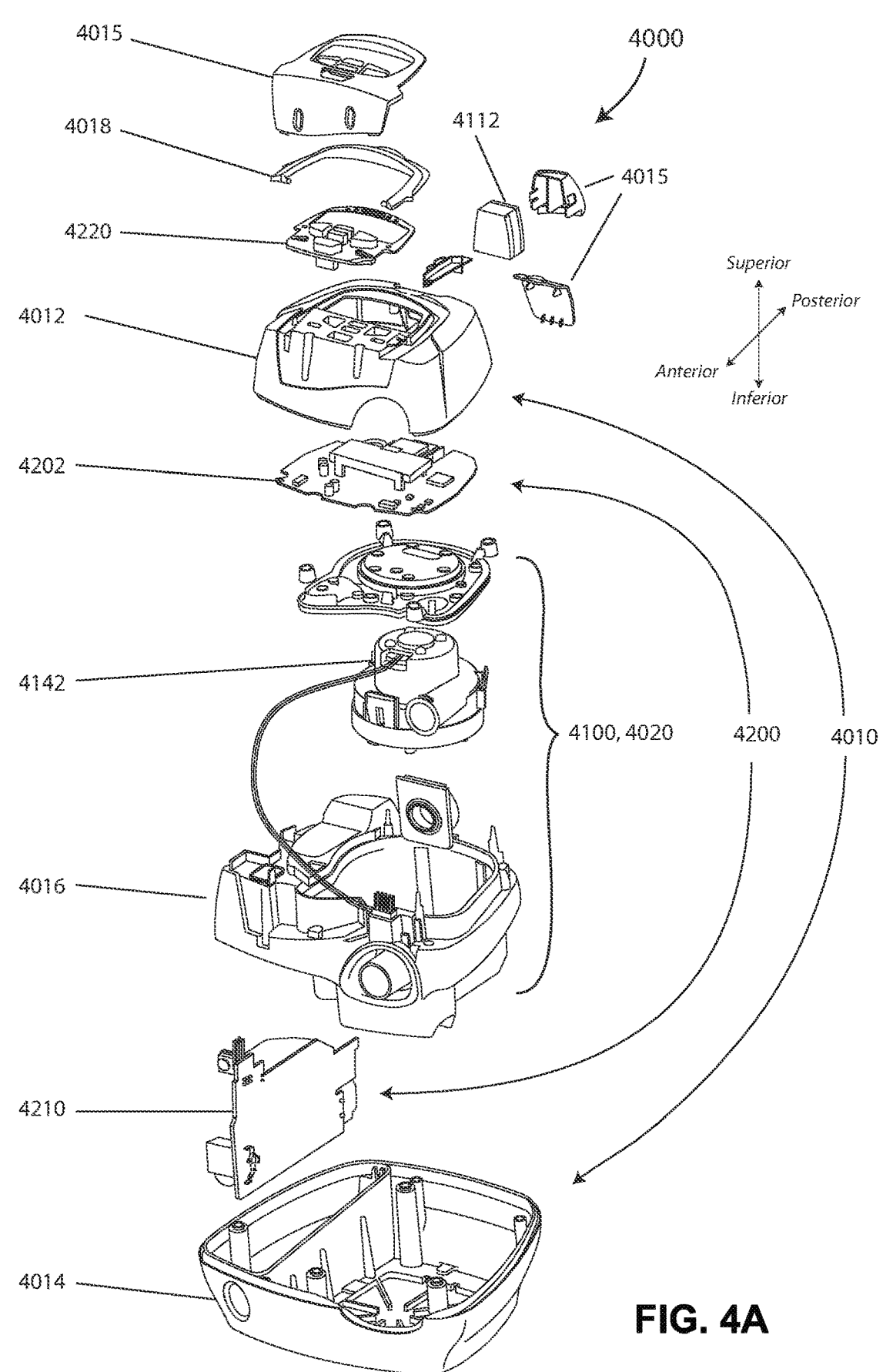

FIG. 4A shows an RPT device in accordance with one form of the present technology.

Figure 4B:
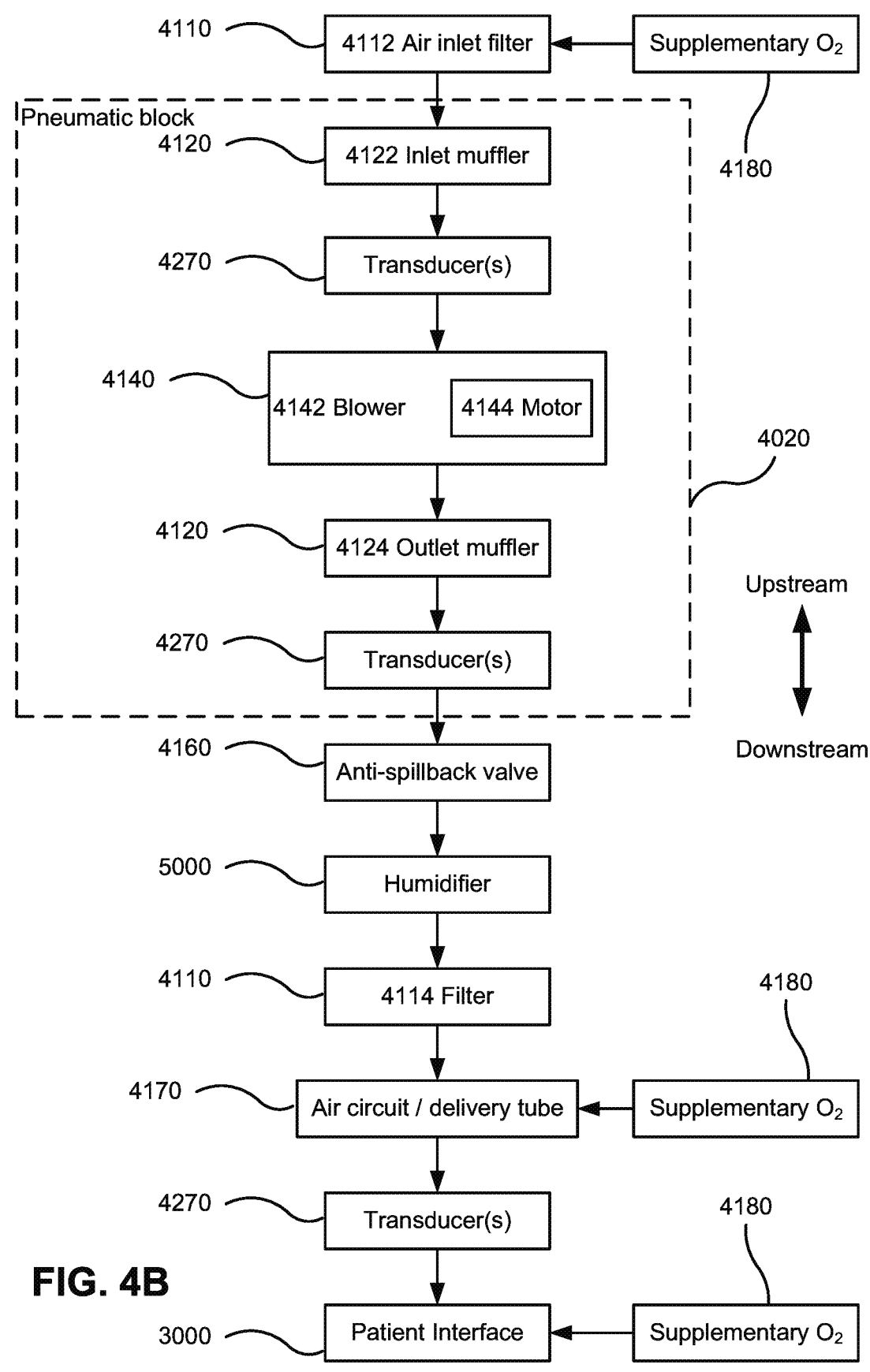

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
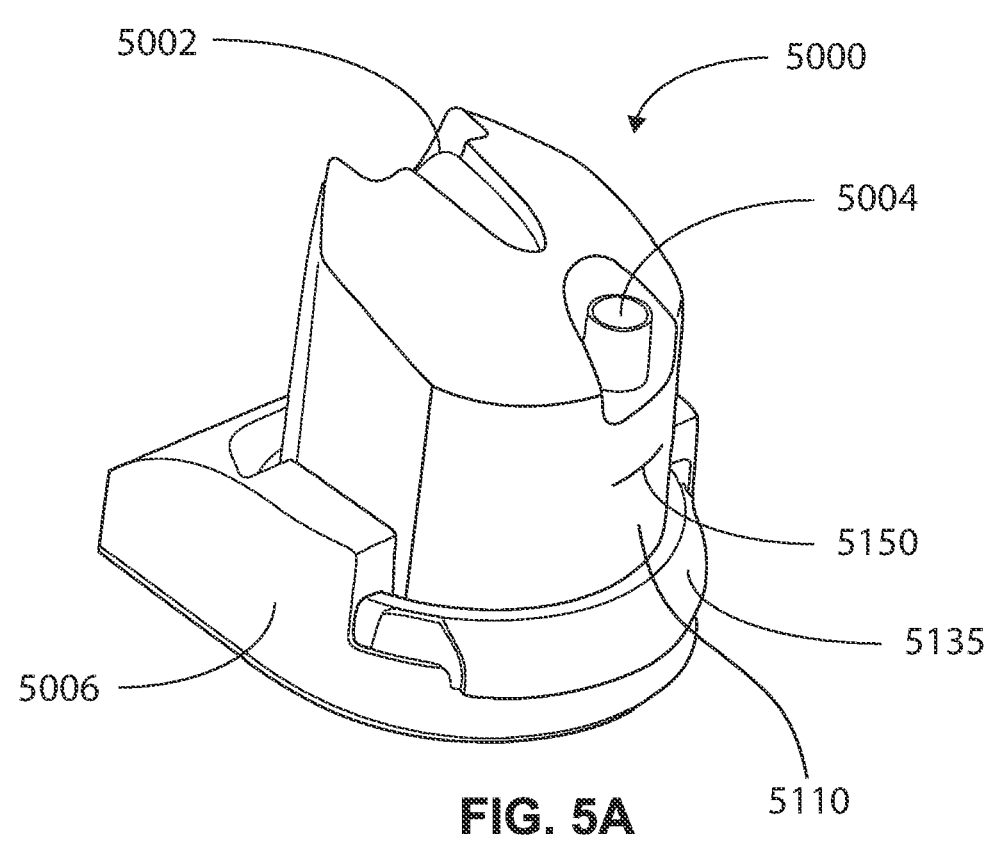

FIG. 5A shows an isometric view of a humidifier in accordance with one form of the present technology.

Figure 5B:
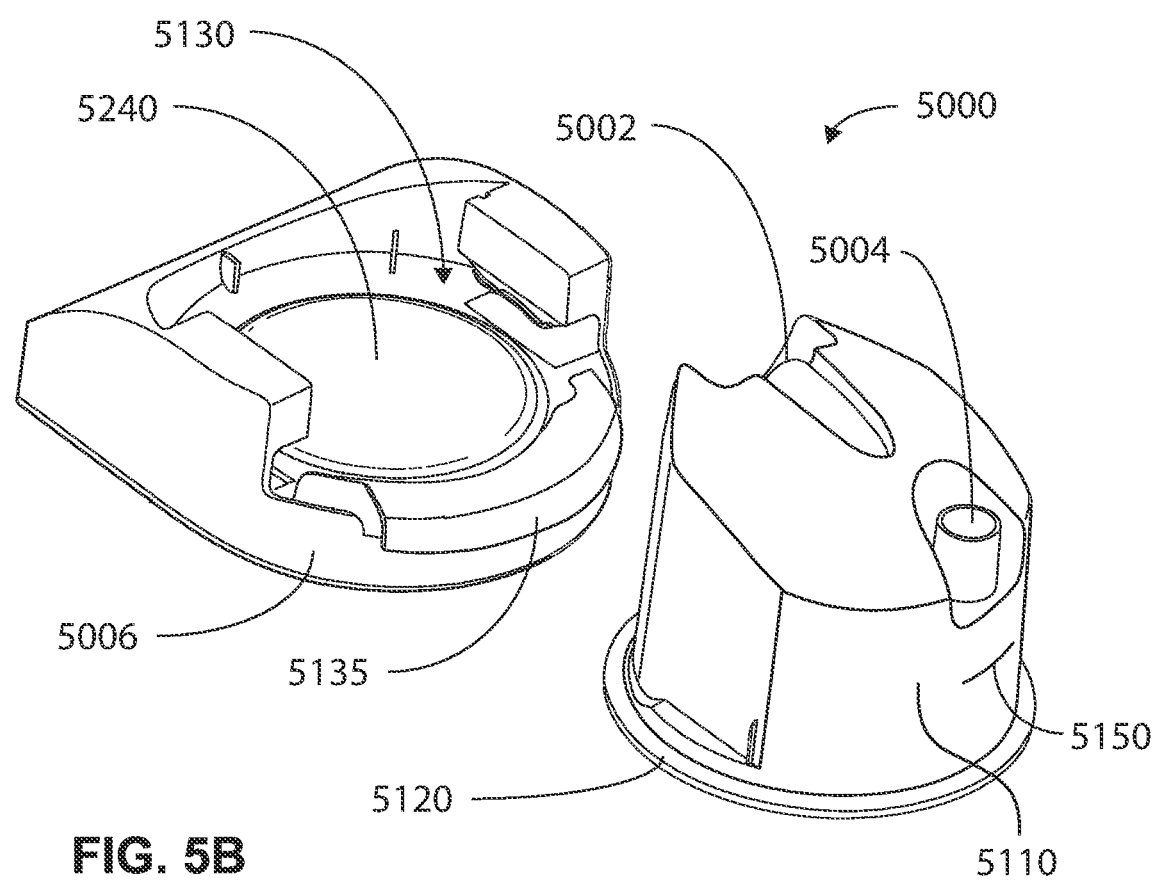

FIG. 5B shows an isometric view of a humidifier in accordance with one form of the present technology, showing a humidifier reservoir 5110 removed from the humidifier reservoir dock 5130.

4.6 Breathing Waveforms

Figure 6:
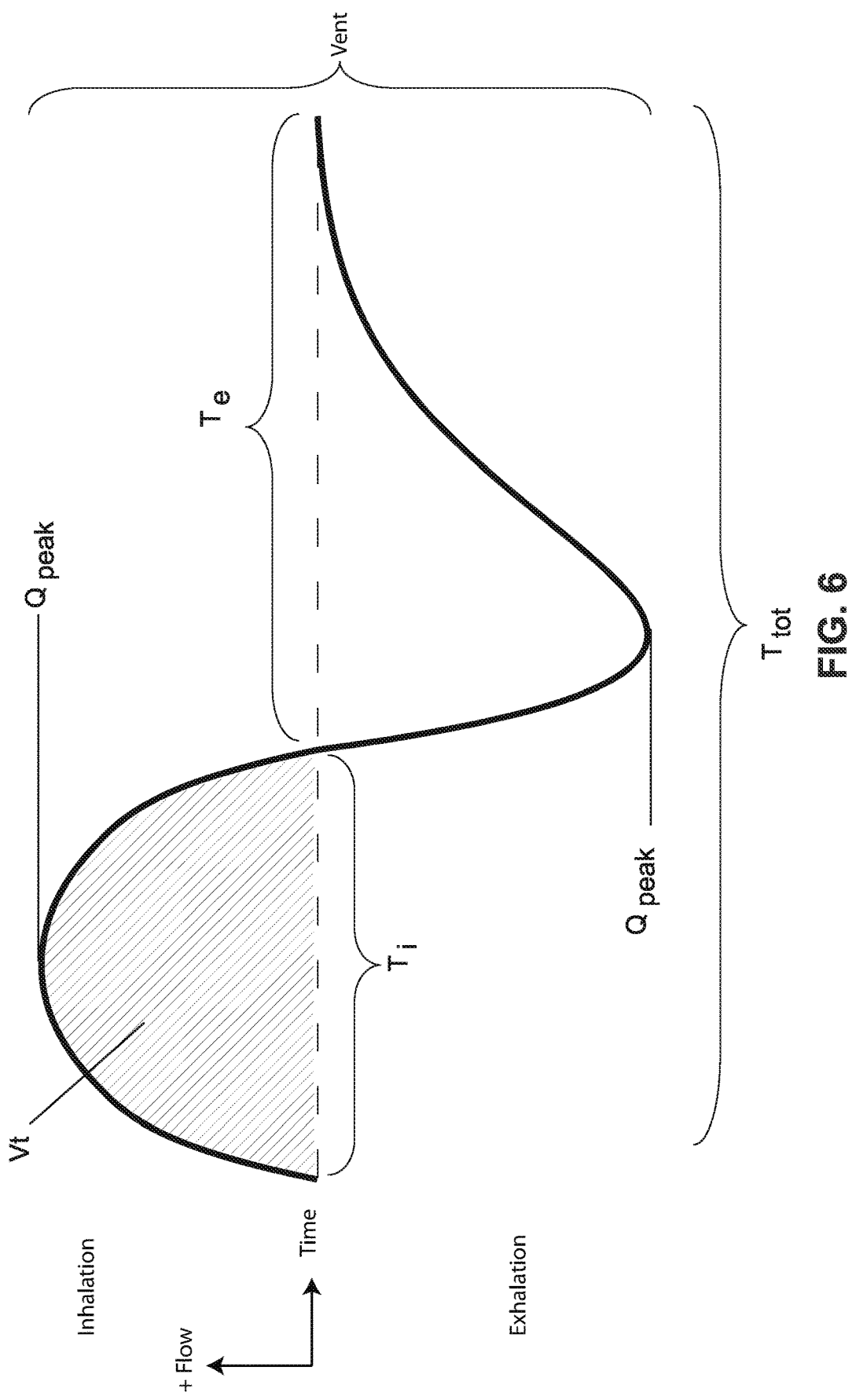

FIG. 6 shows a model typical breath waveform of a person while sleeping.

4.7 Modular Patient Interface

Figure 7:
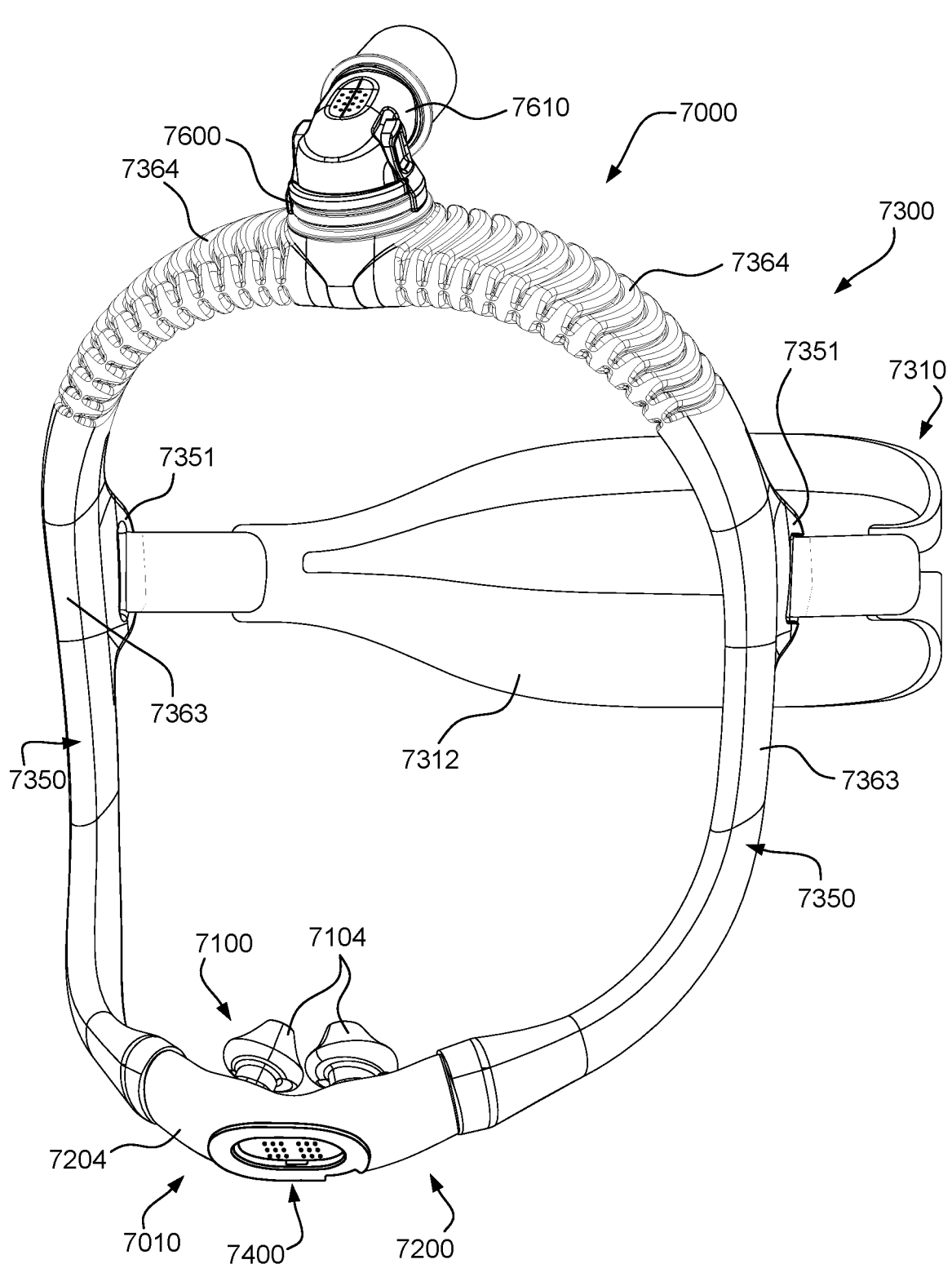

FIG. 7 is a perspective view of a patient interface for providing pressurised air to a patient's nares.

Figure 8:
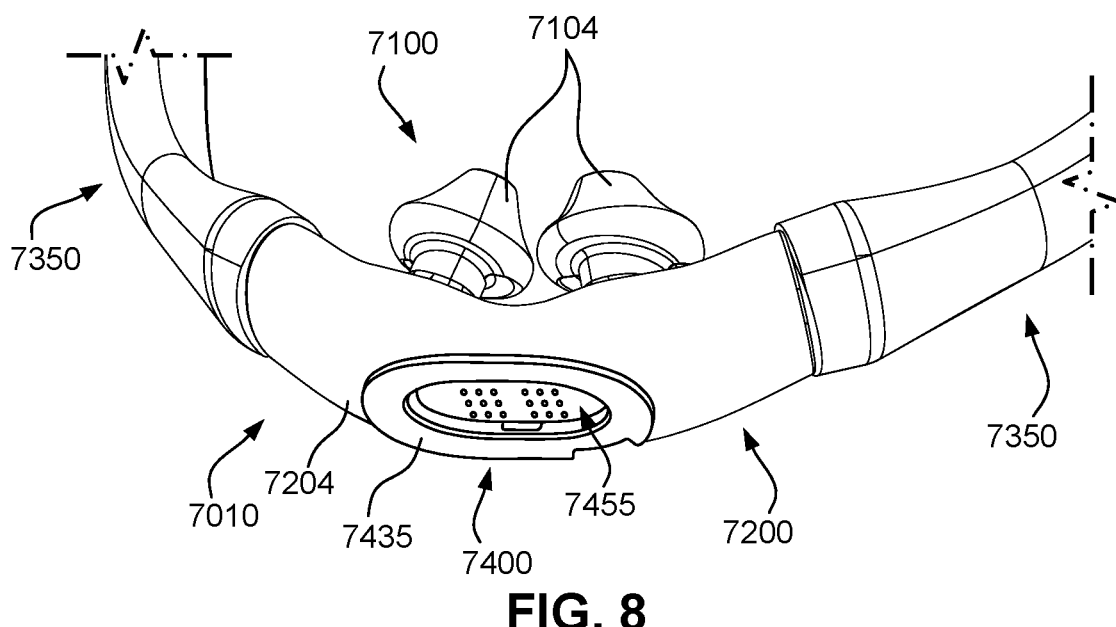

FIG. 8 is a detail view of the patient interface of FIG. 7 illustrating a vent connected to the body of the patient interface.

Figure 9:
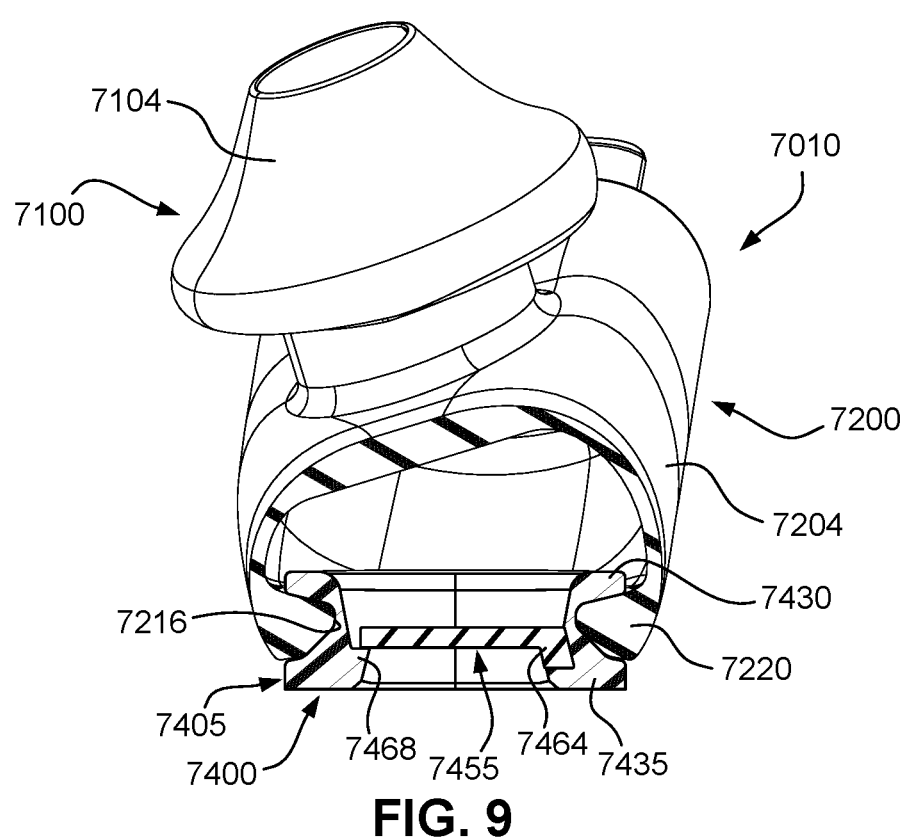

FIG. 9 is a cross-sectional view of the patient interface of FIG. 7, illustrating the interior of the plenum chamber of the patient interface.

FIG. 10 is a perspective view of the vent of the patient interface of FIG. 7.

FIG. 11 is a first cross-sectional view of the vent of FIG. 10 viewed along line 11-11.

Figures 1, 21, 22:
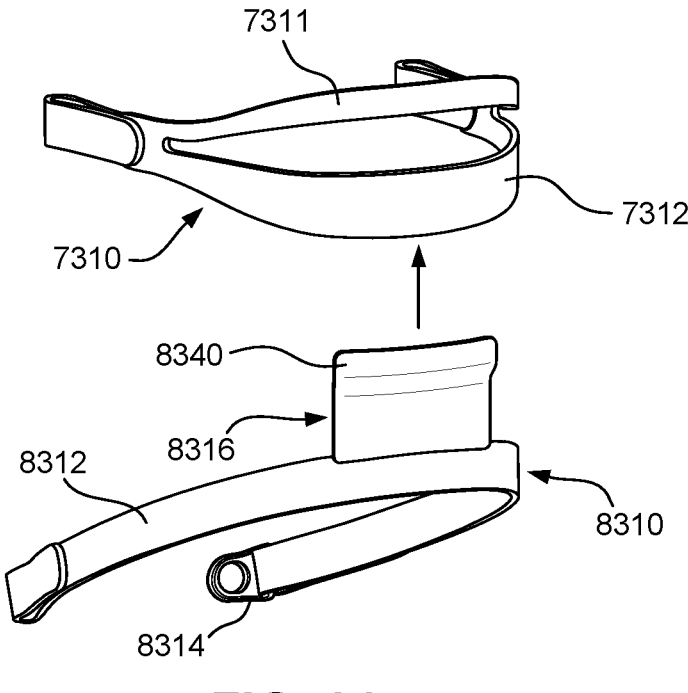

FIG. 11-1 is a second cross-sectional view of the vent of FIG. 10 viewed along line 11-1-11-1.

FIG. 12 is a third cross-sectional view of the vent of FIG. 10 viewed along line 12-12.

Figure 13:
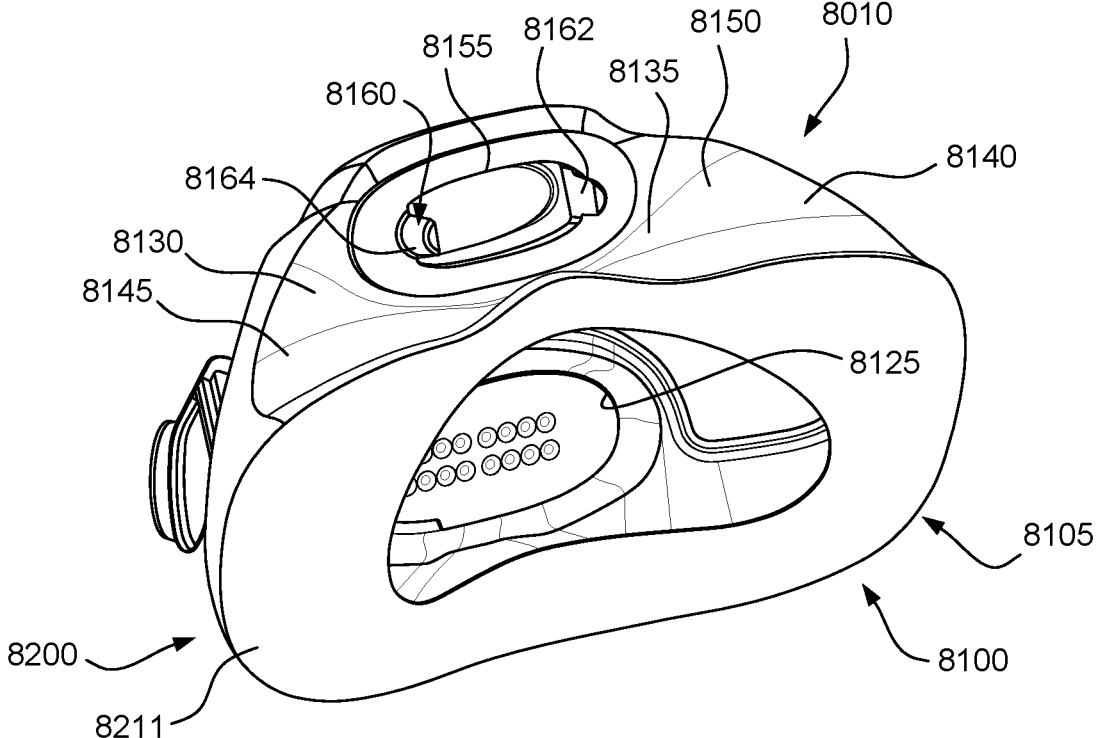

FIG. 13 is a rear perspective view of an oral cushion that is usable in a modular assembly with the patient interface of FIG. 7.

Figure 14:
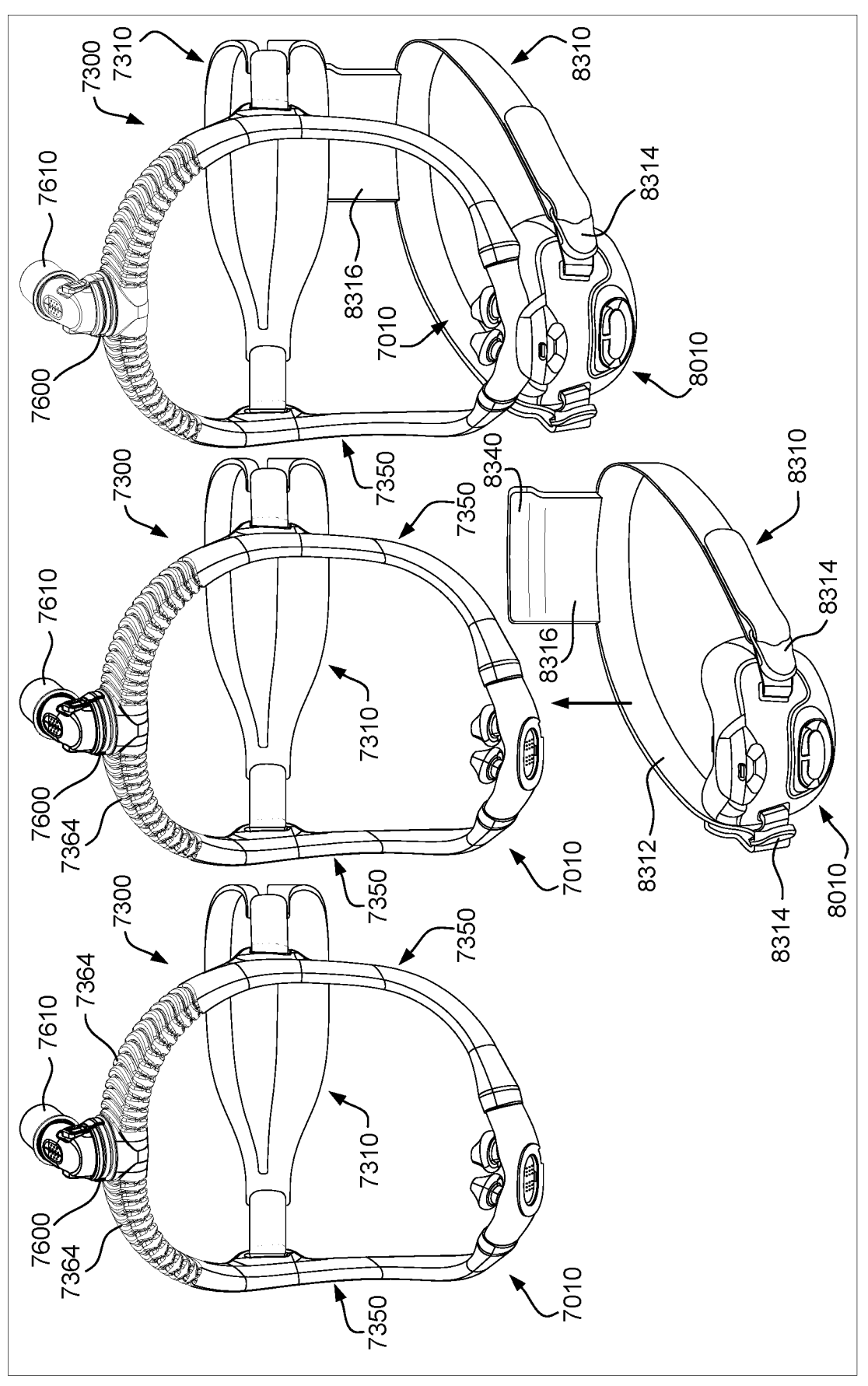

FIG. 14 is a perspective view illustrating the steps of assembling the modular elements of a patient interface including the elements of FIGS. 7 and 13.

Figure 15:
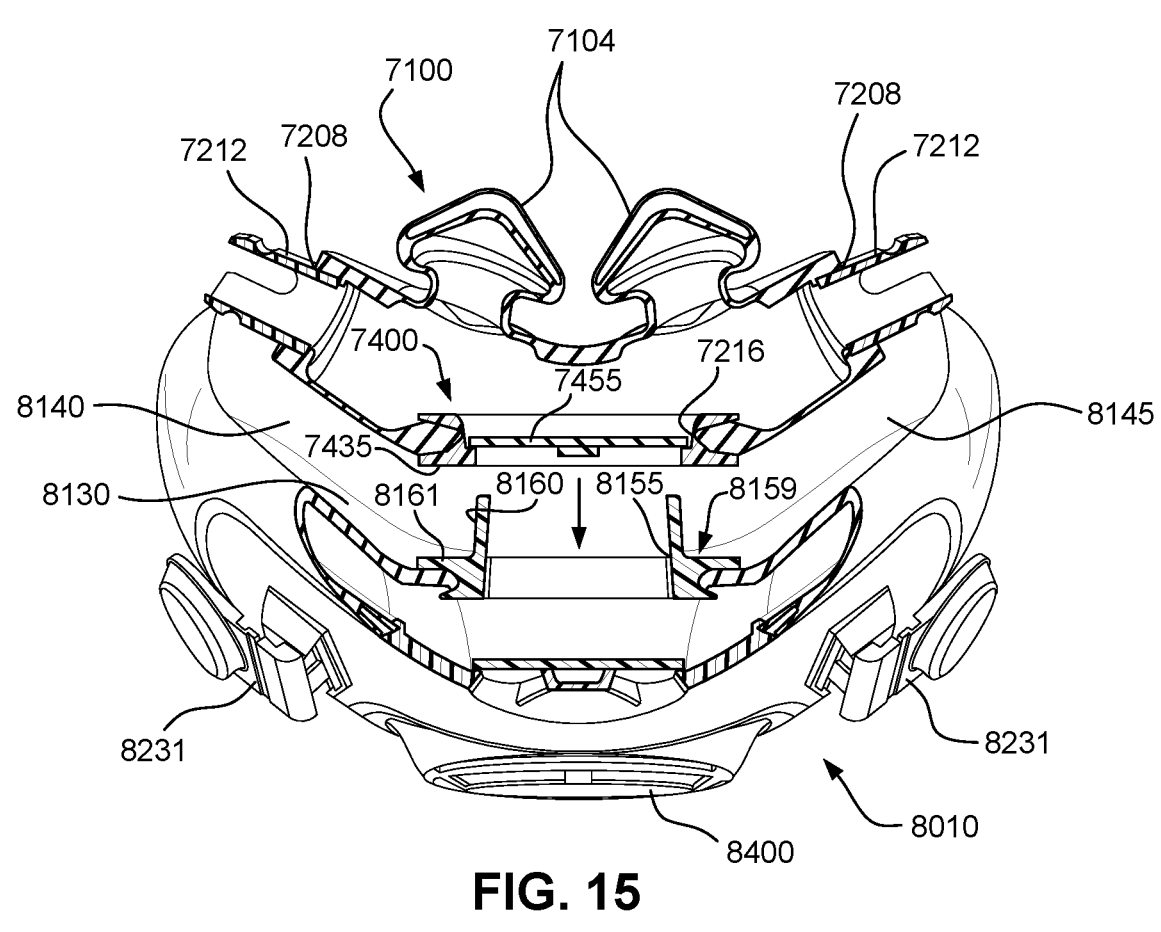

FIG. 15 is a top cross-sectional view illustrating the body of the patient interface of FIG. 7 being assembled with the oral cushion of FIG. 13 in order to form a modular assembly.

Figure 16:
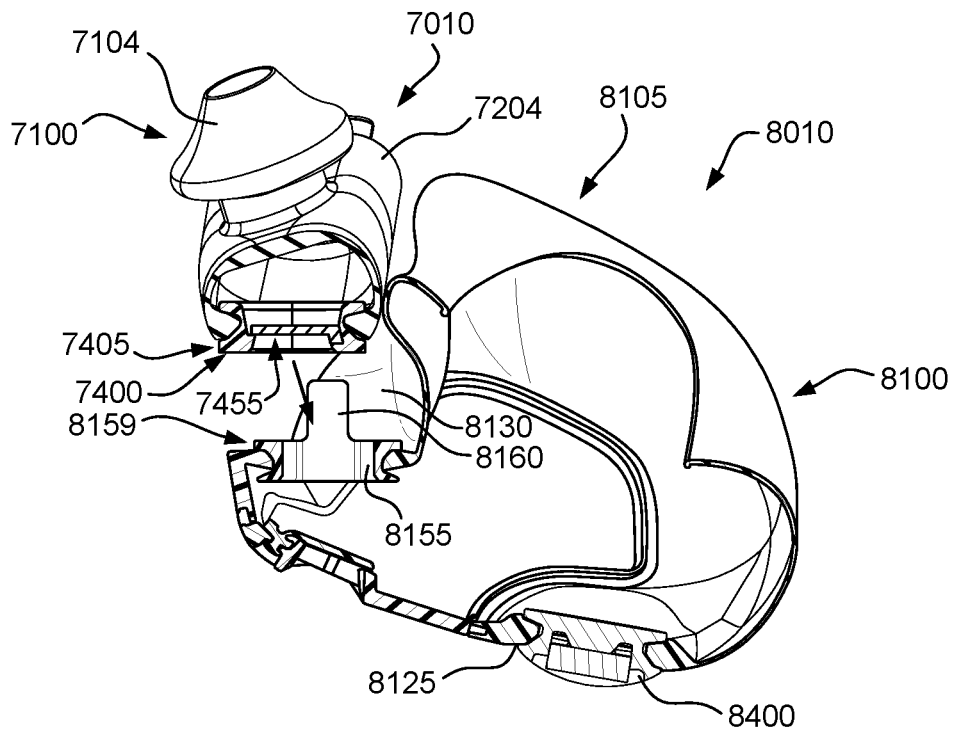

FIG. 16 is a side cross-sectional view illustrating the body of the patient interface of FIG. 7 being assembled with the oral cushion of FIG. 13 in order to form a modular assembly.

Figure 17:
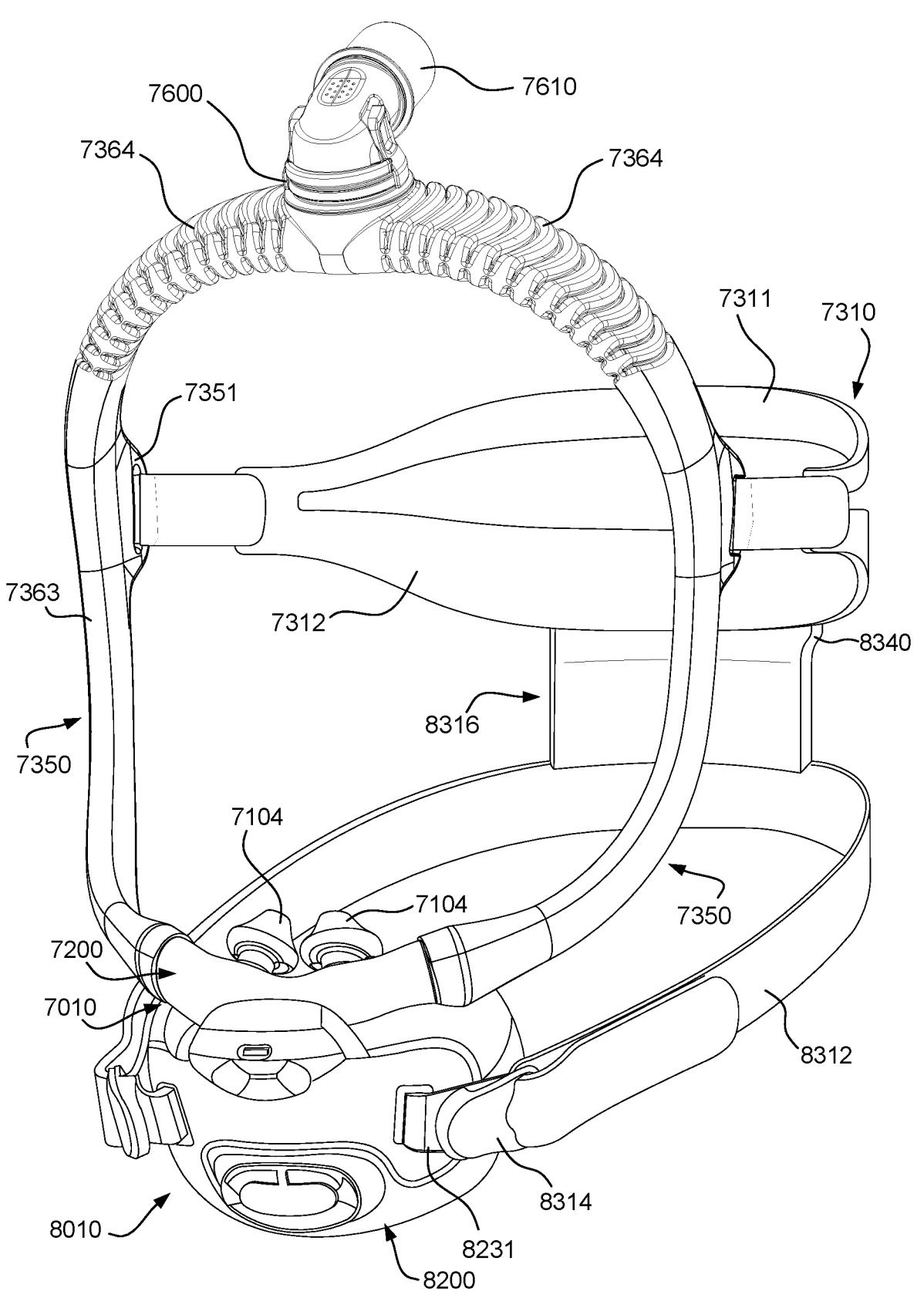

FIG. 17 is a perspective view of the fully connected modular assembly including the patient interface of FIG. 7 and the oral cushion of FIG. 13 so that pressurised air may be delivered to a patient's nares and a patient's mouth.

Figure 18:
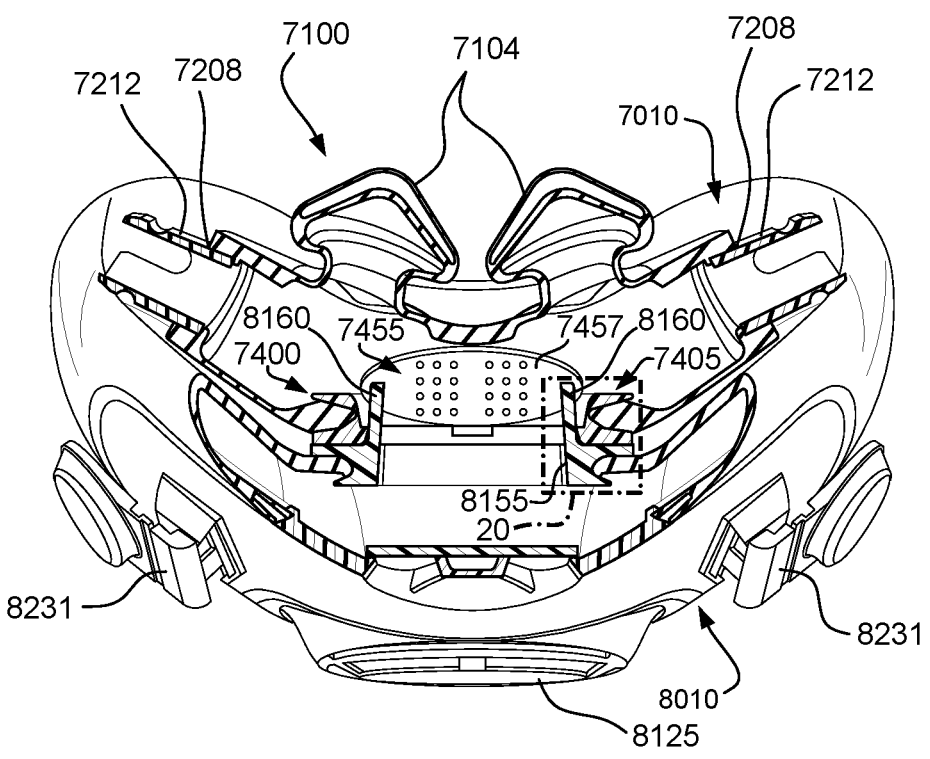

FIG. 18 is a top cross-sectional view illustrating the body of the patient interface of FIG. 7 fully assembled with the oral cushion of FIG. 13 in order to form a modular assembly.

Figure 19:
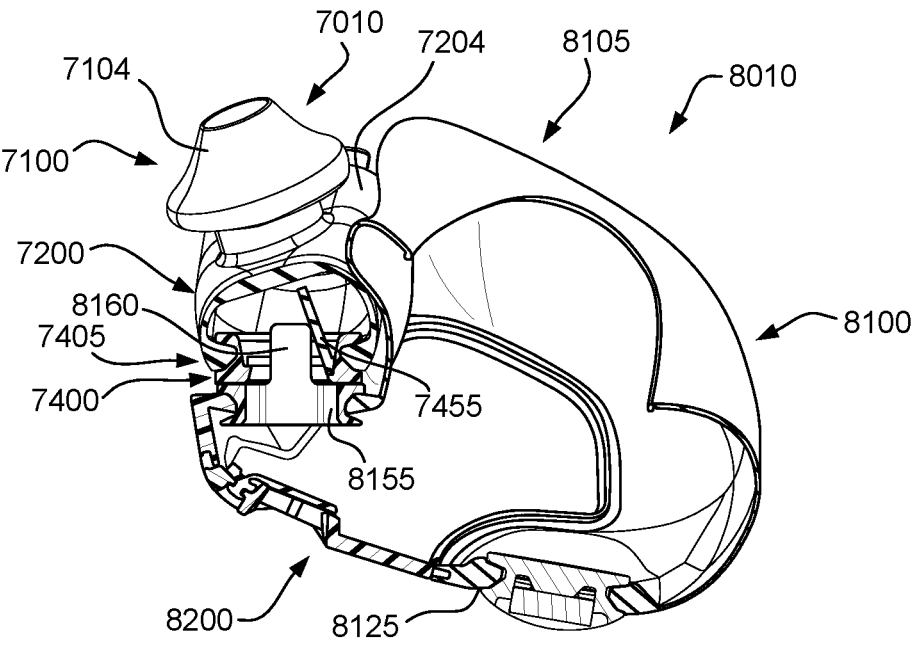

FIG. 19 is a side cross-sectional view illustrating the body of the patient interface of FIG. 7 being assembled with the oral cushion of FIG. 13 in order to form a modular assembly.

Figure 20:
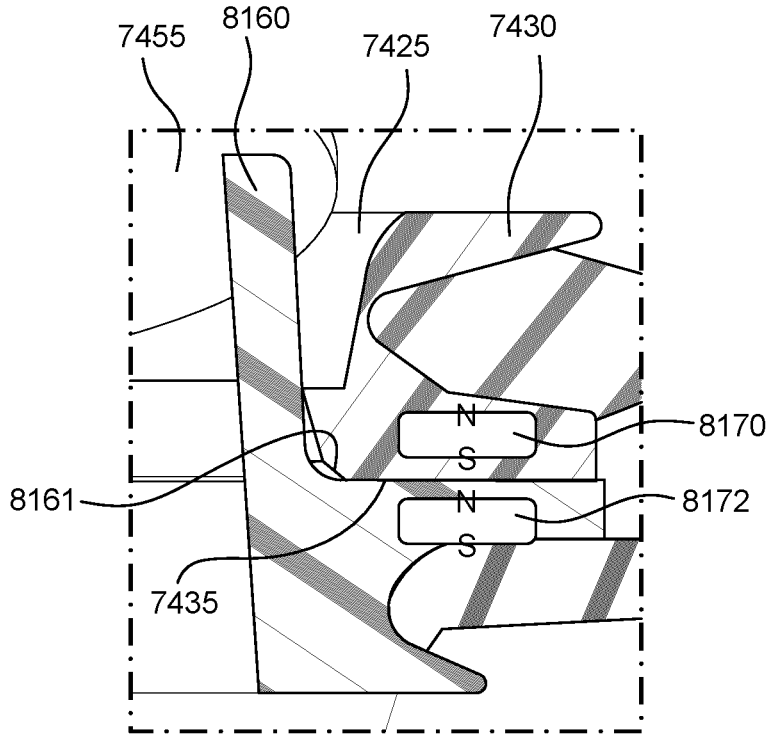

FIG. 20 is a top cross-sectional view illustrating the magnetic connection between the body of the patient interface of FIG. 7 fully assembled with the oral cushion of FIG. 13 in order to form a modular assembly.

FIG. 21 is a rear perspective view of a headgear strap associated with the patient interface of FIG. 7 being connected to a headgear strap associated with the oral cushion of FIG. 13.

FIG. 22 is a rear perspective view of the headgear strap associated with the patient interface of FIG. 7 connected to the headgear strap associated with the oral cushion of FIG. 13.

FIG. 22-1 is a cross-sectional view of a headgear straps of FIG. 22, illustrating a magnetic connection between the headgear straps.

Figure 23:
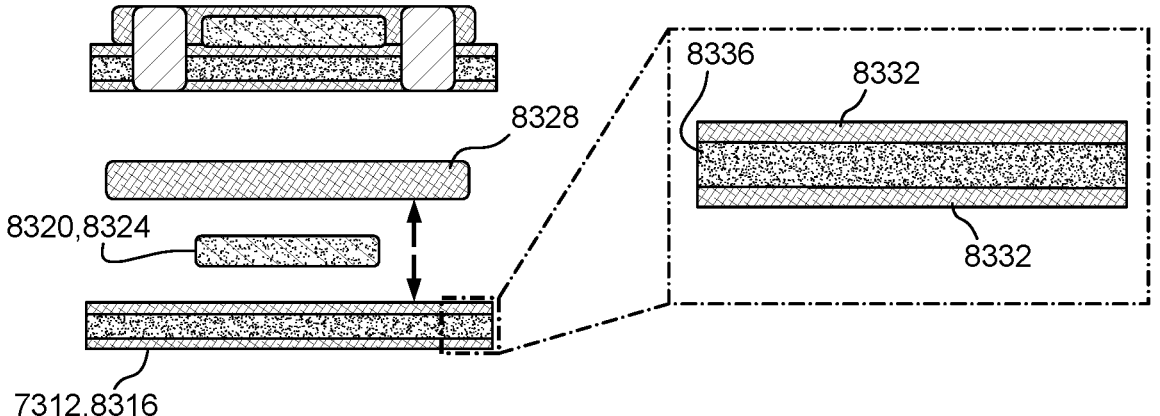

FIG. 23 is a schematic view of a headgear strap illustrating its different materials.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure above the ambient.

The patient interface 3000 in accordance with one form of the present technology is constructed and arranged to be able to provide a supply of air at a positive pressure of at least 2 cmH2O with respect to ambient.

The patient interface 3000 in accordance with one form of the present technology is constructed and arranged to be able to provide a supply of air at a positive pressure of at least 4 cmH2O with respect to ambient.

The patient interface 3000 in accordance with one form of the present technology is constructed and arranged to be able to provide a supply of air at a positive pressure of at least 6 cmH2O with respect to ambient.

The patient interface 3000 in accordance with one form of the present technology is constructed and arranged to be able to provide a supply of air at a positive pressure of at least 10 cmH2O with respect to ambient.

The patient interface 3000 in accordance with one form of the present technology is constructed and arranged to be able to provide a supply of air at a positive pressure of at least 20 cmH2O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

As illustrated in FIGS. 7 to 9, one form of a patient interface 7000 may include a seal forming structure 7100 with a pair of nasal pillows 7104. As described above, each nasal pillow 7104 may be constructed from a flexible material, and may be shaped to form a seal with the respective naris of the nose of the patient.

The nasal pillows 7104 may include openings through which the pressurized respiratory gas may be discharged into the patient's nasal passages. The surface (rim) around the openings in the nasal pillows 7104 may be saddle shaped. Also, it is contemplated that the nasal pillows may have a double wall structure or a single wall structure (not shown).

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

In some forms, the plenum chamber 3200 is constructed from a rigid material such as polycarbonate. The rigid material may provide support to the seal-forming structure.

In some forms, the plenum chamber 3200 is constructed from a flexible material (e.g., constructed from a soft, flexible, resilient material like silicone, textile, foam, etc.). For example, in examples then may be formed from a material which has a Young's modulus of 0.4 GPa or lower, for example foam. In some forms of the technology the plenum chamber 3200 may be made from a material having Young's modulus of 0.1 GPa or lower, for example rubber. In other forms of the technology the plenum chamber 3200 may be made from a material having a Young's modulus of 0.7 MPa or less, for example between 0.7 MPa and 0.3 MPa. An example of such a material is silicone.

5.3.2.1 Nasal Plenum Chamber

As illustrated in FIG. 7, the patient interface 7000 has body 7010 (or nasal cushion) that includes the seal-forming structure 7100 and a plenum chamber 7200. The plenum chamber 7200 includes a wall 7204 that at least partially forms the boundary of the plenum chamber 7200. The nasal pillows 7104 of the seal-forming structure 7100 may be connected to the wall 7204 in order to communicate with the plenum chamber 7200.

As shown in FIG. 8, the plenum chamber 7200 may be connected to the tubes 7350 (described in more detail below). This may allow the tubes to covey pressurised air directly into the plenum chamber 7200.

As illustrated in FIG. 15, the plenum chamber 7200 may include a pair of inlets 7208. Each inlet 7208 may be disposed at a lateral side of the plenum chamber 7200. The inlets 7208 may provide openings into the plenum chamber 7200.

In the illustrated example, each inlet 7208 may include a connecting member 7212, which is illustrated as a mechanical connecting member. However, other examples may include a magnetic connecting member, an adhesive connecting member, or any similar connecting member (or any combination thereof). The illustrated connecting member 7212 may assist in forming an airtight connecting with the tubes 7350 of the positioning and stabilising structure 7300. This may be the result of a snap fit, press fit, friction fit, or any similar mechanical connection. Each connecting member 7212 may be inserted into the respective tube 7350 and engage a complementary feature. This engagement may retain the connection between the tubes 7350 and the plenum chamber 7200, and form a substantially airtight passage so that the pressurised air from the tubes 7350 pass into the plenum chamber 7200 with minimal to no leaks.

With continued reference to FIG. 15, the plenum chamber 7200 may also include a vent opening 7216 formed in the wall 7204. The vent opening 7216 may be disposed on an anterior portion of the wall 7204, substantially opposite of the nasal pillows 7104. The vent opening 7216 may also be substantially in between the inlets 7208.

In some forms, the vent opening 7216 may include a round shape. The illustrated vent opening 7216 may have an elliptical shape, although other examples may have a circular shape. In still other examples, the vent opening 7216 may include a non-circular shape (e.g., a rectangular shape, a triangular shape, etc.).

As shown in FIG. 9, the wall 7204 may include a lip 7220 around the perimeter of the vent opening 7216. The lip 7220 may be a thickened portion that extends toward a centre of the plenum chamber 7200 so that the vent opening 7216 may be narrower than adjacent portions of the wall 7204.

In some forms, the lip 7220 may also be thicker than the adjacent portions of the wall 7204. The lip 7220 may also include a chamfer or other angled surface from the exterior portion of the wall 7204 toward the inner portion of the plenum chamber 7200.

5.3.2.2 Oral Plenum Chamber

As shown in FIGS. 13 to 20, the patient interface 7000 may further include an oral cushion 8010. The oral cushion 8010 may comprise the seal-forming structure 8100 and the wall 8211 bounding the plenum chamber 8200. The oral cushion 8010 may also be referred to as a cushion and shell assembly, cushion and frame assembly, or cushion/frame with the seal-forming structure 8100 forming the cushion portion and the wall 8211 forming the shell or frame portion. It is contemplated that the wall 8211 may also be referred to as a frame or a shell.

The wall 8211 may form at least part of an anterior side of the plenum 8200. In addition, the positioning and stabilising structure 3300 may be connected to the oral cushion 8010 at the wall 8211 (see FIG. 17 and described in more detail below). In particular, the wall 8211 may include a pair of headgear connectors 8231.

The headgear connectors 8231 may be located on opposing lateral sides of the centre of the oral cushion 8010. In addition, the headgear connectors 8231 may be configured to corresponding lower headgear straps and/or conduits of the positioning and stabilizing structure 3300. The headgear connectors 8231 may form part of a magnetic connection and/or a mechanical connection with the corresponding lower headgear strap and/or conduit. In addition, it is contemplated that the headgear connectors 8231 may be rotatatable and/or resiliently flexible. In addition, although the headgear connectors 8231 are illustrated as being components on the wall 8211 (see e.g., FIGS. 17 and 18), it is contemplated that the headgear connectors 8231 may be openings in the wall 8211.

In some configurations, the headgear connectors 8231 may be omitted. In configurations without the headgear connectors 8231, the patient interface 7000 may only include the connecting members 7212 on the body 7010. However, other examples may include openings in the wall 8211 that serve as an inlet and are connectable to tubes 7350.

It is contemplated that the wall 8211 may have any number of shapes. One exemplary shape is illustrated in FIGS. 13 and 17. The exemplary shape of the wall 8211 has inferior and superior sides that are further apart at the lateral sides than at the central portion. It is further contemplated that the wall 8211 may be curved so that an interior side of the wall 8211 (i.e., the side facing the plenum 8200) is concave while an exterior side of the wall 8211 (i.e., the side facing away from the plenum 8200) is convex. Accordingly, the entire exterior surface of the wall 8211 may be dome-shaped.

The seal-forming structure 8100 may be in the form of a flexible oro-nasal cushion that may comprise a mouth (or oral) portion 8105 configured to seal around the patient's mouth. As will be described in more detail below, the oral cushion 8010 may be connectable with the body 7010 in order to provide sealing with the patient's nares and mouth.

The mouth portion 8105 may cooperate with the wall 8211 to form the plenum chamber 8200. The mouth portion 8105 may include a continuous target seal-forming region around the patient's mouth that is configured to engage the patient's upper lip and the patient's chin.

As shown in FIG. 13, it is contemplated that the mouth portion 8105 may include a vent opening 8125 configured to receive a vent assembly 8400. The third opening 8125 may be located on an anterior facing side of the mouth portion 8105. The vent assembly 8400 will be described in more detail, later. It is contemplated that the surface of the mouth portion 8105 around the third opening may be dome shaped.

A superior (or upper) surface of the mouth portion 8105 may form a receptacle 8130 configured to receive the main body 7010. The receptacle 8130 may be in the form of a recess in the mouth portion 8105 and may be referred to as any type of recess such as, for example, a pocket, an indentation, a bowl, a socket, a basin, a trough.

The receptacle 8130 may comprise a base 8135 at a base of the receptacle 8130 and at least one side wall 8140 extending from the base 8135, the at least one side wall 8140 terminating at an outer rim 8145 of the receptacle 8130. The base 8135 and the at least one side wall 8140 may form a receiving space 8150 that receives the main body 7010. The receiving space 8150 may be shaped so that a perimeter of the receptacle 8130 at the outer rim 8145 is larger than the perimeter of the receptacle 8130 at the base 8135. In addition, the receiving space 8150 may be separated from the plenum chamber 8200 by the base 8135 and the at least one side wall 8140. Also, a receptacle opening 8155 of the mouth portion 8105 may be located in the base 8135. The receptacle opening 8155 may allow the pressurized respiratory gas to communicate between the plenum chamber 8200 and the plenum chamber 7200 of the main body 7010.

In some forms, the receptacle opening 8155 may be formed through a connection body 8159 that is connected to the oral cushion 8010. The connection body 8159 may be constructed from a rigid or semi-rigid material. This may be a material that is more rigid that the material of the oral cushion 8010. The connection body 8159 may be permanently connected to the oral cushion 8010, although it may be removably connected in other examples (e.g., to facilitate cleaning).

FIG. 13 illustrates the receptacle opening 8155 with a round shaped (e.g., elliptical, circular, etc.). However, the receptacle opening 8155 may have any shape that allows the flow of pressurized respiratory gas to flow into or out of the plenum 8200. In addition, it is contemplated that the rim around the receptacle opening 8155 may be saddle shaped, while the outer rim 8145 may include alternating cylinder and dome shaped regions. A trough may be formed between the saddle shaped rim and the dome and cylinder shaped outer rim. Alternatively, the base 8135 of the receptacle 8130 may be flat and/or planar so that the receptacle 8130 does not have a trough. The shape of the receptacle 8130 may allow the main body 7010 to be positioned closer to a central part of the oral cushion 8010 to form a more compact structure when the main body 7010 is secured to the mouth portion 8105.

It is contemplated that the wall 8211 (or shell) may extend over a superior side of the mouth portion 8105 so that the wall 8211 forms the receptacle 8130 and includes the receptacle opening 8155. The shapes described above would also apply to a receptacle opening 8155 and receptacle 8130 formed by the wall 8211.

The main body 7010 may comprise a shape that is complementary to the shape of the at least one side wall 8140 of the receptacle 8130. It is contemplated that the wall 7204 may be constructed from a soft, flexible, resilient material such as, for example, silicone. As such, the wall 7204 may be configured to conform to the shape of the at least one side wall 8140 of the receptacle 8130 when the main body 7010 is received within the receptacle 8130.

5.3.3 Positioning and Stabilising Structure

The seal-forming structure 3100 of the patient interface 3000 of the present technology may be held in sealing position in use by the positioning and stabilising structure 3300.

The positioning and stabilising structure 3300 may comprise and function as "headgear" since it engages the patient's head in order to hold the patient interface 3000 in a sealing position. Examples of a positioning and stabilising structure may be shown in FIG. 3A.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.3.1 Modular Positioning and Stabilising Structure

As shown in FIGS. 7 to 23, the patient interface 7000 includes a positioning and stabilising structure 7300 contacts the patient's head in use and provides a force to maintain the seal-forming structure 7100 in a sealing position.

Like the plenum chamber 7200 described above, the positioning and stabilising structure 7300 may be modular and may include multiple pieces that may be connectable and separable 5.3.3.1.1 Headgear Tubing In some forms of the present technology, the positioning and stabilising structure 7300 comprises one or more tubes 7350 that deliver pressurised air received from a conduit forming part of the air circuit 4170 from the RPT device to the patient's airways, for example through the plenum chamber 7200. In the form of the present technology illustrated in FIG. 7, the positioning and stabilising structure 7300 may comprise two tubes 7350 that deliver air to the seal-forming structure 7100 from the air circuit 4170. The tubes 7350 may be an integral part of the positioning and stabilising structure 7300 of patient interface 7000 to position and stabilise the seal-forming structure 7100 of the patient interface to the appropriate part of the patient's face (for example, the nose and/or mouth). This may allow the conduit of air circuit 4170 to provide the flow of pressurised air to connect to a connection port 3600 of the patient interface in a position other than in front of the patient's face which may be unsightly to some people. While a pair of tubes 7350 have some advantages (described below), in some examples, the positioning and stabilising structure 7300 may comprise only a single tube 7350 configured to overlie the patient's head on one side. A strap or other stabilising component may be provided to the other side of the patient's head between the top end of the single tube 7350 and the seal-forming structure 7100, to provide balanced forces on the seal-forming structure 7100.

Since air can be contained and passed through headgear tubing 7350 in order to deliver pressurised air from the air circuit 4170 to the patient's airways, the positioning and stabilising structure 7300 may be described as being inflatable. It will be understood that an inflatable positioning and stabilising structure 7300 does not require all components of the positioning and stabilising structure 7300 to be inflatable. For example, in the example shown in FIG. 7, the positioning and stabilising structure 7300 comprises the headgear tubing 7350, which is inflatable, and the straps 7310, which are not inflatable.

In the form of the present technology illustrated in FIG. 7, the positioning and stabilising structure 7300 comprises two tubes 7350, each tube 7350 being positioned in use on a different side of the patient's head and extending across the respective cheek region, above the respective ear (superior to the otobasion superior on the patient's head) to the elbow 7610 on top of the head of the patient 1000. This form of technology may be advantageous because, if a patient sleeps with their head on its side and one of the tubes 7350 is compressed to block or partially block the flow of gas along the tube 7350, the other tube remains open to supply pressurised gas to the patient. In other examples of the technology, the patient interface 7000 may comprise a different number of tubes, for example one tube, or three or more tubes. In one example in which the patient interface has one tube 7350, the single tube 7350 is positioned on one side of the patient's head in use (e.g. across one cheek region) and a strap forms part of the positioning and stabilising structure 7300 and is positioned on the other side of the patient's head in use (e.g. across the other region) to assist in securing the patient interface 7000 on the patient's head.

In the form of the technology shown in FIG. 7, the two tubes 7350 are fluidly connected at their upper ends to each other and to connection port 7600. In one embodiment, the two tubes are integrally formed while in other embodiments the tubes are separate components that are connected together in use and may be disconnected, for example for cleaning or storage. Where separate tubes are used they may be indirectly connected together, for example each may be connected to a T-shaped conduit having two conduit arms each fluidly connectable to the tubes 7350 and a third conduit arm or opening acting as the connection port 7600 and connectable in use to the air circuit 4170. The connection port 7600 may comprise an elbow 7610 received in fluid connection at the centre of two integrally formed tubes 7350.

The tubes 7350 may be formed of a semi-rigid material such as an elastomeric material, e.g. silicone. For example, the tubes 7350, from the left-side non-extendable tube section 7363 to the right side non-extendable tube section 7363, may be formed (e.g., by molding) from a single homogeneous piece of material, such as silicone. The tubes may have a natural, preformed shape and be able to be bent or moved into another shape if a force is applied to the tubes. For example, the tubes may be generally arcuate or curved in a shape approximating the contours of a patient's head between the top of the head and the nasal or oral region.

In the illustrated example, an extendable tube section 7364 may be disposed on each tube 7350 adjacent to each non-extendable tube section 7363. The extendable tube sections 7364 may be constructed as concertina sections, which may stretch upon application of a tensile force. The extendable tube sections 7364 may stretch as a result of the patient donning the positioning and stabilising structure 7300. Patients with larger heads may create more extension in the extendable tube sections 7364 as compared to patients with smaller heads. This may allow a single size of tube 7350 to fit a variety of patients. When the patient removes the positioning and stabilising structure 7300 from their head, the extendable tube sections 7364 may return to their original position.

As described in U.S. Pat. No. 6,044,844, the contents of which are incorporated herein, the tubes 7350 may be crush resistant to avoid the flow of breathable gas through the tubes if either is crushed during use, for example if it is squashed between a patient's face and pillow. Crush resistant tubes may not be necessary in all cases as the pressurised gas in the tubes may act as a splint to prevent or at least restrict crushing of the tubes 7350 during use. A crush resistant tube may be advantageous where only a single tube 7350 is present as if the single tube becomes blocked during use the flow of gas would be restricted and therapy will stop or reduce in efficacy.

In certain forms of the technology, one or more portions of the tubes 7350 may be rigidised by one or more rigidising or stiffening elements. Examples of rigidising elements include: sections of the tubes 7350 that are comparatively thicker than other sections; sections of the tubes 7350 that are formed from a material that is comparatively more rigid that the material forming other sections; and a rigid member attached to the inside, outside or embedded in a section of tube. The use of such rigidising elements helps to control how the positioning and stabilising structure 7300 will function in use, for example where the tubes 7350 is more likely to deform if forces are applied to them and where the shape of the tubes 7350 is more likely to be maintained if forces are applied. The selection of where such rigidising elements are positioned in the tubes 7350 can therefore help to promote comfort when the patient interface 7000 is worn and can help to maintain a good seal at the seal-forming structure 7100 during use. Rigidising or stiffening elements may be in positioning and stabilising structures 7300 which are configured to support relatively heavy seal-forming structures such as full face or oro-nasal cushion assemblies.

The tubes 7350 in the form of the technology shown in FIG. 7 have a length of between 15 and 30 cm each, for example between 20 and 27 cm each. In one example each of the tubes are around 26 cm long. In another example each of the tubes is around 23 cm long. The length of the tubes is selected to be appropriate for the dimensions of the heads of typical patients, for example the distance between the region proximate the top of the head where the upper end of the tubes 7350 are situated, and the region proximate the openings to the patient's airways at which the lower end of the tubes 7350 when following a generally arcuate path down the sides of the heads and across the patient's cheek region such as is shown in FIG. 7. The patient interface 7000 is configured so that the length of the tubes 7350 can be varied in some forms of the technology and the above lengths may apply to the tube in a contracted, stretched or neutral state (e.g., this length may be adjustable based on the extension of the extendable tube sections 7364). It will be appreciated that the length of the tubes 7350 will depend on the length of other components in the patient interface 7000, for example the length of arms of a T-shaped conduit to which the upper ends of tubes 7350 connect and/or the size of the plenum chamber 7200.

5.3.3.1.2 Headgear Straps

As illustrated in FIG. 7, the positioning and stabilising structure 7300 comprises at least one headgear strap acting in addition to the tubes 7350 to position and stabilise the seal-forming structure 7100 in sealing position at the entrance to the patient's airways. The strap 7310 forms part of the positioning and stabilising structure 7300. The strap 7310 may be known as a back strap or a rear headgear strap, for example.

The strap 7310 may connect to the tubes 7350 via eyelets 7351. In the illustrated example, each non-extendable tube section 7363 includes an eyelet 7351. Each eyelet 7351 is configured to contact the patient's head superior to the patient's ears. This may allow the strap 7310 to contact the patient's head at least partially above the patient's ears. For example, on each side of the patient's head, the strap 7310 may overlay the patient's temporal bone and/or the patient's parietal bone proximate to the connection with the eyelet 7351. The strap 7310 may extend to a rear (e.g., posterior region) of the patient's head and overlay the patient's occipital bone.

In some forms, the strap 7310 may be threaded through each eyelet 7351. At least a portion of the strap 7310 may have a width approximately the same as the width of the eyelet 7351 in order to allow the strap 7310 to slide through. Ends of the strap 7310 may include a connector (e.g., hook or loop material, a magnet, a mechanical connector, etc.). The strap 7310 may be threaded through each eyelet 7351 and folded back on itself in order to adjust the length of the strap 7310 for a particular patient's head.

In the illustrated example, the strap 7310 is bifurcated and includes a first portion 7311 and a second portion 7312 that are movable relative to one another. The patient may adjust the position of the first and second portions 7311, 7312 in order to change the fit. For example, adjusting the position of the first portion 7311 and/or the second portion 7312 on the patient's head may make the strap 7310 tighter or looser, which may allow the strap 7310 to be used with a variety of head sizes.

In some forms, the strap 7310 may be at least partially constructed from a textile material. The textile material may be comfortable to a patient and assist in avoiding irritation.

In certain forms, the strap 7310 may be substantially inextensible. The fit of the strap 7310 may be adjusted using the bifurcated portion (i.e., the first portion 7311 and the second portion 7312) and/or by threading different lengths through the eyelets 7351. Once in the desired portion, the strap 7310 may not stretch or further adjust.

In certain forms, the strap 7310 may be at least partially elastic and may be able to stretch. For example, the strap 7310 may begin in a neutral position while not in use. The strap 7310 may stretch when donned by the patient in order to make smaller adjustments beyond adjusting the bifurcated portion and/or threading the length through the eyelets 7351.

5.3.3.1.2.1 Modularity

As illustrated in FIG. 14, a separate strap 8310 may be used with the oral cushion 8010. For example, the separate strap 8310 may be removably connected to the headgear connector 8231 (e.g., via magnets, mechanical fasteners, adhesives, hook and loop material, etc.). The separate strap 8310 may also be called the oral cushion strap.

In some forms, the oral cushion strap 8310 includes a lower strap portion 8312, which may be similar to the strap 7310. For example, the lower strap portion 8312 may be length of material (e.g., a textile) with connectors on either end. The connectors may be hook and loop material, or another similar connector (e.g., mechanical fastener, magnet, etc.). Additionally, the lower strap portion 8312 may be substantially inextensible, or at least a portion may be elastic and stretchable.

Although not illustrated, it is contemplated that the lower strap portion 8312 may be bifurcated similar to the strap

7310. Bifurcation in the lower strap portion 8312 may allow similar adjustment to the strap 7310 by repositioning the bifurcated portions.

In some forms, the lower strap portion 8312 may be connected to a pair of connecting members 8314, one at either end of the lower strap portion 8312. In the illustrated example, the ends of the lower strap portion 8312 each may be threaded through one of the connecting members 8314 and removably attached using the connectors (e.g., hook and loop material). The connecting members 8314 may directly connect to the headgear connectors 8231 (e.g., using magnets). In other examples, the connectors at the ends of the lower strap portion 8312 could connect directly to the headgear connectors 8231.

In some forms, the lower strap portion 8312 may contact the patient's head inferior to the patient's ears. For example, the lower strap portion 8312 may overlay the masseter muscle in use.

In some forms, the oral cushion strap 8310 may further include a rear strap 8316, which may be disposed between the ends of the lower strap portion 8312. The rear strap 8316 may be permanently connected to the lower strap portion 8312. This may be accomplished via stitching, ultra-sonic welding, adhesives, integral construction, or any similar means. Alternatively, it is contemplated that the rear strap 8316 may be removably connected to the lower strap portion 8312 (e.g., via magnets, adhesives, hook and loop material, mechanical fasteners, etc.).

In use, the rear strap 8316 may contact the posterior portion of the patient's head and overlay the patient's occipital bone. The rear strap 8316 may be wider than the lower strap portion 8312 in order to support a greater portion of the posterior region of the patient's head.

As illustrated in FIG. 14, the strap 7310 and the oral cushion strap 8310 are separate but are usable together. In other words, the oral cushion strap 8310 may be removably connected to the strap 7310. This may allow the strap 7310 to be used independently from the oral cushion strap 8310.

In some forms, the rear strap 8316 may be used to connect the strap 7310 to the oral cushion strap 8310. This connection may occur as the patient is converting the patient interface 7000 from a nasal mask (see e.g., FIG. 7) to an oro-nasal mask (see e.g., FIG. 17).

As shown in FIGS. 21 to 23, the rear strap 8316 may be removably connected to the second portion 7312 of the strap 7310. The rear strap 8316 may be connected so that it is substantially centered on the second portion 7312 of the strap 7310.

As shown in FIGS. 22 and 22-1, the strap 7310 and the oral cushion strap 8310 may be connected using magnets. For example, the strap 7310 may have a first magnet 8320 with a first polarity (e.g., a negative polarity) and the oral cushion strap 8310 may have a second magnet 8324 with a second polarity (e.g., a positive polarity) that is opposite to the first polarity. Thus, the magnetic forces may attract the magnets 8320, 8324 together in order to removably connect the strap 7310 and the oral cushion strap 8310 together.

As shown in FIGS. 22-1 and 23, the first magnet 8320 and/or the second magnet 8324 may not be exposed, and instead may be sandwiched between layers of material. For example, the magnet(s) 8320, 8324 may be positioned against an outer surface of the respective strap 7312, 8316. A separate piece of material 8328 that is larger than the magnet 8320, 8324 may be positioned over the magnet 8320, 8324 in order to cover the magnet 8320, 8324.

In some forms, the separate piece of material 8328 may be laminated onto the respective strap 7312, 8316 so that the respective magnet 8320, 8324 is disposed in between. Ultra-sonic welding may be added in order to additionally secure the magnet 8320, 8324 to the strap 7312, 8316.

In other forms, the magnet(s) 8320, 8324 may be formed with the respective strap 7312, 8316 (e.g., without the separate piece of material 8328). For example, FIG. 23 illustrates a strap (e.g., the strap 7310 and/or the oral cushion strap 8310) formed with three layers of material. For example, the strap may include two outer layers 8332 and an inner layer 8336. In the illustrated example, the outer layers 8332 may be formed from the same material (e.g., melange UBL/no-UBL fabric). Although in other examples, the outer layers 8332 may be formed from different materials. Additionally, the inner layer 8336 may be a different material than both of the outer layers 8332. For example, the inner layer 8336 may be a compressible material (e.g., a foam). In alternate forms, the magnet(s) 8320, 8324 may be disposed between the outer layers 8332 (e.g., adjacent to the inner layer 8336).

In still other forms, the strap 7310 and/or the oral cushion strap 8310 may include an exposed magnet. In other words, the first magnet 8320 and/or the second magnet 8324 may be coupled to an outer surface of the respective strap (e.g., the second portion 7312 or the rear strap 8316). The respective magnet 8320, 8324 and strap 7312, 8316 may be connected together using stitching. Having the magnet(s) 8320, 8324 exposed may allow the patient to more easily connect the strap 7310 to the oral cushion strap 8310.

As shown in FIGS. 21 and 22, the rear strap 8316 may include a bent portion 8340. In other words, the rear strap 8316 may not be planar and a portion of the rear strap 8316 (i.e., the bent portion 8340) may be out of plane with the remainder of the rear strap 8316.

In some forms, the bent portion 8340 may be angled in the posterior direction (e.g., as oriented when worn by the patient). In other words, the bent portion 8340 may be angled away from the patient's head. As shown in FIG. 22, this may allow the bent portion 8340 to contact a rear surface of the second portion 7312 of the strap 7310. In other words, the bent portion 8340 may not contact the patient's head in use.

In some forms, the bent portion 8340 may allow the remainder of the rear strap 8316 to be relatively flat against the patient's head, in use. This may be more comfortable for a patient.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.4.1 Modular Vent

As illustrated in FIGS. 10 to 12, a vent 7400 may allow for the washout of exhaled gases through the vent opening 7216 of the plenum chamber 7200. In addition, the vent 7400 may be positioned away from the inlet 7208 into the plenum 7200. In some forms, the vent 7400 may be configured to be permanently retained within the vent opening 7216. However, it is contemplated that the vent 7400 may be removable from the vent opening 7216 for cleaning.

The vent 7400 may include a main body 7405 that may be formed of a rigid material such as plastic and may be the part of the vent 7400 that anchors the vent 7400 to the wall 7204 of the plenum chamber 7200. The main body 7405 may comprise a frame 7420 with features that secure the vent 7400 to the wall 7204 and a receptacle 7425 with a receiving space that is bound by the frame 7420. In other examples, the main body 7405 may be formed from an at least partially flexible material (e.g., rubber).

The frame 7420 may include a first flange 7430 that extends around a perimeter of the frame 7420. A second flange 7435 may be located opposite the first flange 7430. The first flange 7430 and the second flange 7435 may together form a channel 7440. When the vent 7400 is assembled to the wall 7204, at least a portion of the rim of the vent opening 7216 may be received within the channel 7440 so that the first flange 7430 and the second flange 7435 may hold the frame 7420 in place within the vent opening 7216. In addition, the engagement of the first flange 7430 and the second flange 7435 with the rim of the vent opening 7216 may form a seal so that the exhaled gas may flow through the vent 7400 and not around the vent 7400.

In addition, it is contemplated that there may be one or more gaps (or notches) 7445 in the first flange 7430 and/or the second flange 7435. The gaps 7445 may be positioned, sized, and shaped to be complimentary to a tab (not shown) extending from the rim of the vent opening 7216. The tab may be received by corresponding one of the gaps 7445 when the frame 7420 is in the correct orientation. The tab may prevent the frame 7420 from being received within the vent opening 7216 when the frame 7420 is in the wrong orientation. It should be understood that the locations of the gaps 7445 and the tabs may be swapped so that the gaps 7445 are located on the rim of the vent opening 7216 and the tabs are located on the first flange 7430 and/or the second flange 7435. It is further contemplated that the vent 7400 may have other alignment indicators such as printed indicia.

The receptacle 7425 may include a vent wall 7455 with a plurality of vent holes 7460. In the illustrated example, the vent wall 7455 may be substantially straight. However, it is contemplated that the vent wall 7455 may be contoured so that a side of the vent wall 7455 facing the anterior direction away from the patient has a convex shape, and an opposite side of the vent wall 7455 (e.g., facing into the plenum chamber 7200) is concave. The plurality of vent holes 7460 may be arranged in any pattern. For example, as shown in FIG. 10, the vent wall 7455 may comprise eighteen vent holes 7460 arranged in three rows.

In some forms, each vent hole 7460 may have a substantially constant diameter along its length. In other forms, at least some vent holes 7460 (e.g., one, a majority, all, etc.) may be tapered (e.g., toward the anterior direction and the second flange 7435 in a direction away from the plenum 7200). In other words, the cross-sectional area of the vent path through each vent hole 7460 may decrease as the vented gas moves further away from the plenum 7200.

As illustrated in FIGS. 11 and 11-1, a connecting portion 7464 may be coupled to the vent wall 7455. The connecting portion 7464 may engage the main body 7405. The connecting portion 7464 may be angled relative to the vent wall 7455, which may allow the vent wall 7455 to be situated toward a middle of the receptacle 7425.

In some forms, a retaining wall 7468 may be disposed around at least a portion of the perimeter of the receptacle 7425 (e.g., within the receptacle 7425). In the illustrated example, the retaining wall 7468 may extend around the entire perimeter of the receptacle 7425.

The retaining wall 7468 may contact a surface of the vent wall 7455. For example, the retaining wall 7468 may extend over the outer perimeter of the vent wall 7455 along an outer surface 7457 of the vent wall 7455 (e.g., a surface facing in an anterior direction away from the patient's face).

In some forms, the vent wall 7455 may be movable relative to the main body 7405. The movement may create a space around between an outer perimeter of the vent wall 7455 and the inner perimeter of the receptacle 7425.

In some forms, the vent wall 7455 may be movable (e.g., flexible, bendable, pivotable, translatable, etc.) relative to the vent body 7405. For example, the engagement between the connecting portion 7464 and the main body 7405 may form a hinge. A force applied to the outer surface 7457 may cause the vent wall 7455 to move away from the retaining wall 7468.

In some forms, the vent wall 7455 may be biased toward the retaining wall 7468. For example, removing a force from the outer surface 7457 may cause the vent wall 7455 to return toward its initial position and contact the retaining wall 7468. The retaining wall 7468 may limit additional movement toward the second flange 7435. The hinge created by the connecting portion 7464 may allow for repeated flexible movement of the vent wall 7455.

In some forms, the vent wall 7455 may be biased toward the retaining wall 7468 (e.g., in a sealing positon) and may be translatable away from the retaining wall 7468. The vent wall 7455 may move in a linear direction relative to the vent body 7405. The vent body 7405 may have a non-uniform size (e.g., frustoconical) where the vent wall 7455 seals against the smallest diameter and is not sealed when moving into a larger diameter.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

In certain forms of the present technology, the patient interface 7000 may comprise a connection port 7600 located proximal a top, side or rear portion of a patient's head. For example, in the form of the present technology illustrated in FIG. 7, the connection port 7600 is located on top of the patient's head. In this example the patient interface 7000 comprises an elbow 7610 to which the connection port 7600 is provided. The elbow 7610 may swivel with respect to the positioning and stabilising structure 7300 in order to decouple movement of a conduit connected to the connection port 7600 from the positioning and stabilising structure 7300. Additionally, or alternatively, a conduit connected to the connection port 7600 may swivel with respect to the elbow 7610. In the illustrated example, elbow 7610 comprises a swivelling conduit connector to which a conduit of the air circuit 4170 is able to connect such that the conduit can rotate about its longitudinal axis with respect to the elbow 7610.

Patient interfaces in which the connection port is not positioned in front of the patient's face may be advantageous as some patients find a conduit that connects to a patient interface in front of the face to be unsightly and obtrusive. For example, a conduit connecting to a patient interface in front of the face may be prone to being tangled up in bedclothes or bed linen, particularly if the conduit extends downwardly from the patient interface in use. Forms of the technology with a patient interface with a connection port positioned proximate the top of the patient's head in use may make it easier or more comfortable for a patient to lie or sleep in one or more of the following positions: in a side or lateral position; in a supine position (i.e. on their back, facing generally upwards); and in a prone position (i.e. on their front, facing generally downwards). Moreover, connecting a conduit to the front of a patient interface may exacerbate a problem known as tube drag, wherein the conduit may provide an undesired drag force upon the patient interface thereby causing dislodgement away from the face.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.3.10 Modularity

At least some of the above described components may be modular in order to allow a patient to use the patient interface 7000 in a variety of configurations. For example, a patient may use a nasal mask (see e.g., FIG. 7) or an oro-nasal mask (see e.g., FIG. 17). A patient may be able to switch between the different components as the need presents itself. For example, a patient may begin using the oro-nasal mask, but may transition to the nasal mask as they become accustom to the therapy (e.g., rely more on breathing though their nares). Additionally, the modularity may simplify manufacturing by reducing and/or standardizing components between the different versions of the masks. The connection between the nasal mask and the oro-nasal mask may be similar to the connection method described in U.S. application Ser. No. 17/550,168, the contents of which is incorporated herein by reference in its entirety.

As described above, a patient may use the body 7010 of FIG. 7 by itself in order to deliver pressurized gas to the patient's nares. In this example, the patient's mouth remains exposed to the ambient.

Some patients may want and/or require a patient interface to deliver pressurized air to their mouth. To accomplish this, the patient may incorporate the oral cushion 8010 in order to simultaneously deliver pressurized gas to the patient's nares and to the patient's mouth. In other words, the plenum chamber 7200 of the body 7010 and the plenum chamber 8200 of the oral cushion 8010 may combine to effectively form a single plenum chamber.

The modular connection may be accomplished using the vent 7400. As described above, the vent 7400 includes a vent wall 7455 that is flexible relative to the frame 7420. As will be described in more detail below, this flexing or bending movement of the vent wall 7455 may allow the connection between the body 7010 and the oral cushion 8010.

As shown in FIG. 14, the patient may position the body 7010 within the receptacle 8130 of the oral cushion 8010 in order to connect the two together. The receptacle 8130 may be sized and shaped in order to receive the body 7010. For example, a curvature of the receptacle 8130 may substantially correspond to a curvature of the wall 7204. This may create the appearance of a more uniform assembly, which may be more visually appealing and/or more comfortable to a patient.

As shown in FIGS. 15 and 16, the body 7010 is oriented so that the vent 7400 is positioned within the receptacle 8130 and the nasal pillows 7104 are facing away from the receptacle 8130.

In some forms, at least one prong 8160 is disposed around an outside of the receptacle opening 8155. For example, the at least one prong 8160 may be positioned proximate to an outer perimeter of the receptacle opening 8155 and may project into the receptacle 8130. In the illustrated example, the oral cushion 8010 includes a pair of prongs 8160, disposed approximately 180° apart. However, other examples may include a different number of prongs 8160 (e.g., one, three, four, etc.) and/or a different spacing (e.g., approximately 30° apart, approximately 45° apart, approximately 60° apart, approximately 90° apart, approximately 120° apart, etc.).

In some forms, the at least one prong 8160 may be connected to the connection body 8159. For example, the at least one prong 8160 may be integrally formed with the connection body 8159 (e.g., molded as one piece).

In some forms, each prong 8160 may include a substantially straight surface 8162 and a curved surface 8164. As illustrated in FIG. 13, the substantially straight surfaces 8162 face one another and are proximate to the outer perimeter of the receptacle opening 8155. The curved surface 8164 are opposite the respective substantially straight surface 8162.

Returning to FIGS. 15 and 16, a distance from a centre of the receptacle opening 8155 to the curved surface 8164 may be smaller than the receptacle 7425 of the frame 7420 of the vent 7400. The curved surfaces 8164 of the prongs 8160 may be proximate (e.g., contacting) the wall of the receptacle 7425 during the connection process. The curved shape of the curved surface 8164 may provide a smoother engagement between the prongs 8160 and the frame 7420.

As indicated by the arrows in FIGS. 15 and 16, the patient may align the prongs 8160 in order to contact the outer surface 7457 of the vent wall 7455. When aligned, all of the prongs 8160 are positioned within the perimeter of the receptacle 7425.

In certain forms, the prongs 8160 may be constructed from a rigid or semi-rigid material. For example, FIGS. 15 and 16 illustrate that the prongs 8160 may be formed from a separate piece than the oral cushion 8010. The prongs 8160 may be formed from a structure similar to the vent 7400. The prongs 8160 may include a frame and a channel (e.g., similar to the channel 7440 of the frame 7420) that can connect to the oral cushion 8010. This may provide more rigidity to the oral cushion 8010, and may limit the bending of the prongs 8160 as they contact the vent wall 7455.

For example, the prongs 8160 may extend from an insert with a substantially flat surface 8161 of the connection body 8159 that faces into the receptacle 8130 (i.e., faces away from the plenum chamber 8200 of the oral cushion 8010).

As the body 7010 is being inserted into the receptacle 8130, the connecting members 7212 may partially extend beyond the edge of the receptacle 8130. In other words, the end of each connecting member 7212 may extend beyond the oral cushion 8010. This may make connecting and/or disconnecting the tubes 7350 from the body 7010 easier when the body 7010 is within the receptacle 8130.

As illustrated in FIGS. 18 and 19, the prongs 8160 may contact the outer surface 7457 of the vent wall 7455. As described above, the vent wall 7455 may be flexible relative to the frame 7420 (e.g., via the connecting portion 7464 in FIG. 11). The vent wall 7455 is normally biased into a closed position (see e.g., FIGS. 10 to 12). However, contact with the prongs 8160 during insertion of the body 7010 into the receptacle 8130 may overcome the bias and retain the vent wall 7455 in an open position.

In some forms, the vent 7400 may be connected to the body 7010 so that the connecting portion 7464 and the retaining wall 7468 are outside of the plenum chamber 7200 in the closed position of the vent wall 7455. The vent wall 7455 may only be able to move (e.g., flex, bend, pivot, translate, etc.) to an open position in one direction, thus the illustrated orientation of the vent 7400 may allow the vent wall 7455 to move to an open position where it is located within the plenum chamber 7200 of the body 7010.

In certain forms, the vent wall 7455 may be retained in the closed position absent application of an external force. For example, changes in airflow direction (e.g., inhalation and exhalation) may not affect the position of the vent wall 7455. Additionally, the presence of absence of the flow of pressurised air may not affect the position of the vent wall 7455 (e.g., in the opened or closed position). The vent wall 7455 may only move to the open position as a result of physical contact with another element (e.g., the prongs 8160).

For example, the vent wall 7455 may flex toward the nasal pillows 7104 within the plenum chamber 7200 while in contact with the prongs 8160. The vent wall 7455 may not move to vertical (e.g., perpendicular with respect to the first flange 7430 or second flange 7435) but may move beyond 45°. As illustrated in FIG. 19, the vent wall 7455 may move to a position that does not substantially block or obstruct the flow of air through the nasal pillows 7104.

In other examples, contact with the prongs 8160 may cause the vent wall 7455 to translate from the closed (e.g., sealed) position to the open (e.g., unsealed or non-functional) position. As described above, the vent body 7405 may include a frustoconical shape. Contact between the vent wall 7455 and the prongs 8160 may cause the vent wall 7455 to move into a larger diameter section of the vent body 7405, where airflow is then permitted to travel around the outer perimeter of the vent wall 7455.

When connected, the second flange 7435 and the flat surface 8161 may contact one another. Because both surfaces 7435, 8161 are substantially flat, they may create a smooth engagement, which may limit flow paths for pressurized air to escape from the plenum chamber 7200.

In some forms, connectors may be disposed within the second flange 7435 and/or the flat surface 8161 in order to secure the body 7010 to the oral cushion 8010. As shown in FIG. 20, some forms of the second flange 7435 and the flat surface 8161 may include magnets. For example, a first magnet 8170 may be disposed within the second flange 7435 and a second magnet 8172 may be disposed proximate to the flat surface 8161. The illustrated magnets 8170, 8172 are not exposed, although other examples of the second flange 7435 and/or the flat surface 8161 may include exposed magnets.

The first and second magnets 8170, 8172 may have opposite polarities in order to connect to one another (e.g., so that there is a magnetic attractive force). In certain forms, the first magnet 8170 in the second flange 7435 may have a negative polarity and the second magnet 8172 may have a positive polarity, although these may be reversed.

In some forms, the first and second magnets 8170, 8172 may assist in guiding the body 7010 into the proper position within the receptacle 8130. For example, the magnetic forces may help a patient properly align the prongs 8160 with the vent wall 7455. The magnetic forces may draw the first magnet 8170 toward the second magnet 8172, which may assist with the connection, particularly if the patient is in a dark room.

Once connected, the first and second magnets 8170, 8172 may keep the body 7010 secured to the oral cushion 8010. The magnetic forces between the first and second magnets 8170, 8172 may be sufficient to establish a substantially air-tight connection in order to minimize any pressurized gas that may escape. The magnetic forces may also be sufficient to limit or prevent separation of the body 7010 from the oral cushion 8010 during normal use. For example, a patient rolling while sleeping is unlikely to provide the force sufficient to overcome the magnetic force and separate the first and second magnets 8170, 8172. Because of this, the patient may create a modular oro-nasal cushion in order to receive pressurised air through their nares and their mouth, or the patient may disconnect the body 7010 from the oral cushion 8010 in order to deliver air to just their nares. The magnetic force between the first and second magnets 8170, 8172. As described above, this may provide the patient flexibility to use the same elements of the patient interface 7000 in order to achieve different air-delivery goals.

In other examples, the first and second magnets 8170, 8172 may be replaced by any other type of connector. For example, the first and second magnets 8170, 8172 may be replaced with mechanical connectors (e.g., which form a snap fit, press fit, or friction fit engagement). This type of connection may similarly provide a removable connection capable of maintaining its position during use.

In other examples, the body 7010 and the oral cushion 8010 may be connected together using the prongs 8160. For example, the prongs 8160 may fit within the opening of the vent 7400 (e.g., the receptacle 7425) with a snug or tight fit. The prongs 8160 may frictionally engage the sides of the receptacle 7425 in order to removably connect the body 7010 to the oral cushion 8010. Alternatively or in addition, the prongs 8160 may snap fit to the vent 7400 (e.g., against the wall 7468) in order to removably connect the body 7010 and the oral cushion 8010 together.

In certain forms, multiple connection methods may be used to retain the oral cushion 8010 relative to the body 7010. For example, the magnets 8170, 8172 may be used with the mechanical engagement of the prongs 8160 and the vent body 7405.

Similarly, as the body 7010 and the oral cushion 8010 connect to one another (e.g., via the first and second magnets 8170, 8172, or other similar connector), the straps 7310 and the separate straps 8310 may be connected together (e.g., using the first and second magnets 8320, 8324) in order to form the connected four-point headgear.

5.4 RPT Device

An RPT device 4000 in accordance with one aspect of the present technology comprises mechanical, pneumatic, and/or electrical components and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 4 cmH2O, or at least 10 cmH2O, or at least 20 cmH2O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller, a therapy device controller, a pressure generator 4140, one or more protection circuits, memory, transducers 4270, data communication interface and one or more output devices. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example, the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH2O to about 20 cmH2O, or in other forms up to about 30 cmH2O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 may be under the control of the therapy device controller.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.5 Air Circuit

An air circuit 4170 in accordance with an aspect of the present technology is a conduit or a tube constructed and arranged to allow, in use, a flow of air to travel between two components such as RPT device 4000 and the patient interface 3000 or 3800.

5.6 Humidifier 5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components 5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.6.2.5 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.7 Breathing Waveforms

FIG. 6 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Respiratory Therapy Modes

Various respiratory therapy modes may be implemented by the disclosed respiratory therapy system.

5.8.1 CPAP Therapy

In some implementations of respiratory pressure therapy, the central controller sets the treatment pressure Pt according to the treatment pressure equation (Error Reference source not found.) as part of the therapy parameter determination algorithm. In one such implementation, the amplitude A is identically zero, so the treatment pressure Pt (which represents a target value to be achieved by the interface pressure Pm at the current instant of time) is identically equal to the base pressure $P_0$ throughout the respiratory cycle. Such implementations are generally grouped under the heading of CPAP therapy. In such implementations, there is no need for the therapy engine module to determine phase Φ or the waveform template Π(Φ).

In CPAP therapy, the base pressure $P_0$ may be a constant value that is hard-coded or manually entered to the RPT device 4000. Alternatively, the central controller may repeatedly compute the base pressure $P_0$ as a function of indices or measures of sleep disordered breathing returned by the respective algorithms in the therapy engine module, such as one or more of flow limitation, apnea, hypopnea, patency, and snore. This alternative is sometimes referred to as APAP therapy.

5.8.2 Bi-Level Therapy

In other implementations of this form of the present technology, the value of amplitude A in equation (Error Reference source not found.) may be positive. Such implementations are known as bi-level therapy, because in determining the treatment pressure Pt using equation (Error Reference source not found.) with positive amplitude A, the therapy parameter determination algorithm oscillates the treatment pressure Pt between two values or levels in synchrony with the spontaneous respiratory effort of the patient 1000. That is, based on the typical waveform templates Π(d), t) described above, the therapy parameter determination algorithm increases the treatment pressure Pt to $P_0$+A (known as the IPAP) at the start of, or during, or inspiration and decreases the treatment pressure Pt to the base pressure $P_0$ (known as the EPAP) at the start of, or during, expiration.

In some forms of bi-level therapy, the IPAP is a treatment pressure that has the same purpose as the treatment pressure in CPAP therapy modes, and the EPAP is the IPAP minus the amplitude A, which has a "small" value (a few cmH2O) sometimes referred to as the Expiratory Pressure Relief (EPR). Such forms are sometimes referred to as CPAP therapy with EPR, which is generally thought to be more comfortable than straight CPAP therapy. In CPAP therapy with EPR, either or both of the IPAP and the EPAP may be constant values that are hard-coded or manually entered to the RPT device 4000. Alternatively, the therapy parameter determination algorithm may repeatedly compute the IPAP and/or the EPAP during CPAP with EPR. In this alternative, the therapy parameter determination algorithm repeatedly computes the EPAP and/or the IPAP as a function of indices or measures of sleep disordered breathing returned by the respective algorithms in the therapy engine module in analogous fashion to the computation of the base pressure $P_0$ in APAP therapy described above.

In other forms of bi-level therapy, the amplitude A is large enough that the RPT device 4000 does some or all of the work of breathing of the patient 1000. In such forms, known as pressure support ventilation therapy, the amplitude A is referred to as the pressure support, or swing. In pressure support ventilation therapy, the IPAP is the base pressure $P_0$ plus the pressure support A, and the EPAP is the base pressure $P_0$.

In some forms of pressure support ventilation therapy, known as fixed pressure support ventilation therapy, the pressure support A is fixed at a predetermined value, e.g. 10 cmH2O. The predetermined pressure support value is a setting of the RPT device 4000, and may be set for example by hard-coding during configuration of the RPT device 4000 or by manual entry through the input device 4220.

In other forms of pressure support ventilation therapy, broadly known as servo-ventilation, the therapy parameter determination algorithm takes as input some currently measured or estimated parameter of the respiratory cycle (e.g. the current measure Vent of ventilation) and a target value of that respiratory parameter (e.g. a target value Vtgt of ventilation) and repeatedly adjusts the parameters of equation (Error Reference source not found.) to bring the current measure of the respiratory parameter towards the target value. In a form of servo-ventilation known as adaptive servo-ventilation (ASV), which has been used to treat CSR, the respiratory parameter is ventilation, and the target ventilation value Vtgt is computed by the target ventilation determination algorithm from the typical recent ventilation Vtyp, as described above.

In some forms of servo-ventilation, the therapy parameter determination algorithm applies a control methodology to repeatedly compute the pressure support A so as to bring the current measure of the respiratory parameter towards the target value. One such control methodology is Proportional-Integral (PI) control. In one implementation of PI control, suitable for ASV modes in which a target ventilation Vtgt is set to slightly less than the typical recent ventilation Vtyp, the pressure support A is repeatedly computed as:

$$A = Gf(\text{Vent}-\text{Vtgt})dt \qquad (1)$$

where G is the gain of the PI control. Larger values of gain G can result in positive feedback in the therapy engine module. Smaller values of gain G may permit some residual untreated CSR or central sleep apnea. In some implementations, the gain G is fixed at a predetermined value, such as −0.4 cmH2O/(L/min)/sec. Alternatively, the gain G may be varied between therapy sessions, starting small and increasing from session to session until a value that substantially eliminates CSR is reached. Conventional means for retrospectively analysing the parameters of a therapy session to assess the severity of CSR during the therapy session may be employed in such implementations. In yet other implementations, the gain G may vary depending on the difference between the current measure Vent of ventilation and the target ventilation Vtgt.

Other servo-ventilation control methodologies that may be applied by the therapy parameter determination algorithm include proportional (P), proportional-differential (PD), and proportional-integral-differential (PID).

The value of the pressure support A computed via equation (2) may be clipped to a range defined as [Amin, Amax]. In this implementation, the pressure support A sits by default at the minimum pressure support Amin until the measure of current ventilation Vent falls below the target ventilation Vtgt, at which point A starts increasing, only falling back to Amin when Vent exceeds Vtgt once again.

The pressure support limits Amin and Amax are settings of the RPT device 4000, set for example by hard-coding during configuration of the RPT device 4000 or by manual entry through the input device 4220.

In pressure support ventilation therapy modes, the EPAP is the base pressure $P_0$. As with the base pressure $P_0$ in CPAP therapy, the EPAP may be a constant value that is prescribed or determined during titration. Such a constant EPAP may be set for example by hard-coding during configuration of the RPT device 4000 or by manual entry through the input device 4220. This alternative is sometimes referred to as fixed-EPAP pressure support ventilation therapy. Titration of the EPAP for a given patient may be performed by a clinician during a titration session with the aid of PSG, with the aim of preventing obstructive apneas, thereby maintaining an open airway for the pressure support ventilation therapy, in similar fashion to titration of the base pressure $P_0$ in constant CPAP therapy.

Alternatively, the therapy parameter determination algorithm may repeatedly compute the base pressure $P_0$ during pressure support ventilation therapy. In such implementations, the therapy parameter determination algorithm repeatedly computes the EPAP as a function of indices or measures of sleep disordered breathing returned by the respective algorithms in the therapy engine module 4320, such as one or more of flow limitation, apnea, hypopnea, patency, and snore. Because the continuous computation of the EPAP resembles the manual adjustment of the EPAP by a clinician during titration of the EPAP, this process is also sometimes referred to as auto-titration of the EPAP, and the therapy mode is known as auto-titrating EPAP pressure support ventilation therapy, or auto-EPAP pressure support ventilation therapy.

5.8.3 High Flow Therapy

In other forms of respiratory therapy, the pressure of the flow of air is not controlled as it is for respiratory pressure therapy. Rather, the central controller controls the pressure generator 4140 to deliver a flow of air whose device flow rate Qd is controlled to a treatment or target flow rate Qtgt that is typically positive throughout the patient's breathing cycle. Such forms are generally grouped under the heading of flow therapy. In flow therapy, the treatment flow rate Qtgt may be a constant value that is hard-coded or manually entered to the RPT device 4000. If the treatment flow rate Qtgt is sufficient to exceed the patient's peak inspiratory flow rate, the therapy is generally referred to as high flow therapy (HFT). Alternatively, the treatment flow rate may be a profile Qtgt(t) that varies over the respiratory cycle.

5.9 Glossary

For the purposes of the present technology disclosure, in certain forms of the present technology, one or more of the following definitions may apply. In other forms of the present technology, alternative definitions may apply.

5.9.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal (1 hectopascal=100 Pa=100 N/$m^2$=1 millibar ~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.9.1.1 Materials & their Properties (Durometer Hardness (Indentation Hardness): A material property measured by indentation of an indentor (e.g. As measured in accordance with ASTM D2240). May refer to durometer or indentation hardness, which is a material property measured by indentation of an indentor (e.g., as measured in accordance with ASTM D2240)

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45.

Polycarbonate: a thermoplastic polymer of Bisphenol-A Carbonate.

5.9.1.2 Mechanics

Axes:

a. Neutral axis: An axis in the cross-section of a beam or plate along which there are no longitudinal stresses or strains.

b. Longitudinal axis: An axis extending along the length of a shape. The axis generally passes through a center of the shape c. Circumferential axis: An axis oriented perpendicularly with respect to the longitudinal axis. The axis may be specifically present in pipes, tubes, cylinders, or similar shapes with a circular and/or elliptical cross section Deformation: The process where the original geometry of a member changes when subjected to forces, e.g. a force in a direction with respect to an axis. The process may include stretching or compressing, bending and, twisting.

Elasticity: The ability of a material to return to its original geometry after deformation.

Floppy structure or component: A structure or component that will change shape, e.g. bend, when caused to support its own weight, within a relatively short period of time such as 1 second.

Resilience: Ability of a material to absorb energy when deformed elastically and to release the energy upon unloading.

Resilient: Will release substantially all of the energy when unloaded. Includes e.g. certain silicones, and thermoplastic elastomers.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH2O pressure.

As an example, an I-beam may comprise a different bending stiffness (resistance to a bending load) in a first direction in comparison to a second, orthogonal direction. In another example, a structure or component may be floppy in a first direction and rigid in a second direction.

Stiffness: The ability of a structure or component to resist deformation in response to an applied load. A structure or component may have an axial stiffness, a bending stiffness, and a torsional stiffness. A structure or component is said to be stiff when it does not deform easily when subject to mechanical forces. Stiffness of a structure or component is related to its material properties and its shape. The inverse of stiffness is flexibility.

Viscous: The ability of a material to resist flow.

Visco-elasticity: The ability of a material to display both elastic and viscous behaviour in deformation.

Yield: The situation when a material can no longer return back to its original geometry after deformation.

Yield: The situation when a material can no longer return back to its original geometry after deformation.

5.9.1.3 Structural Elements

Compression member: A structural element that resists compression forces.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Membrane: Membrane will be taken to mean a typically thin element that has, preferably, substantially no resistance to bending, but has resistance to being stretched.

Tie (noun): A structure designed to resist tension.

Thin structures:

a. Beams,
  i. A beam may be relatively long in one dimension compared to the other two dimensions such that the smaller dimensions are comparatively thin compared to the long dimension
b. Membranes,
  i. Relatively long in two dimensions, with one thin dimension. Readily deforms in response to bending forces. Resists being stretched, (might also resist compression).
c. Plates & Shells
  i. These may be relatively long in two directions, with one thin dimension. They may have bending, tensile, and/or compressive stiffness.

Thick structures: Solids

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use 5.9.2 Respiratory Cycle Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
  (i) Flattened: Having a rise followed by a relatively flat portion, followed by a fall.
  (ii) M-shaped: Having two local peaks, one at the leading edge, and one at the trailing edge, and a relatively flat portion between the two peaks.
  (iii) Chair-shaped: Having a single local peak, the peak being at the leading edge, followed by a relatively flat portion.
  (iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
  (i) a 30% reduction in patient breathing for at least 10 seconds plus an associated 4% desaturation; or
  (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

Inhalation Time (Ti): The duration of the inspiratory portion of the respiratory flow rate waveform.

Exhalation Time (Te): The duration of the expiratory portion of the respiratory flow rate waveform.

Total Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.9.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

End expiratory pressure (EEP): Desired interface pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP–EPAP). In some contexts, pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator, or other respiratory therapy device such as an RPT device or portable oxygen concentrator, delivers a volume of breathable gas to a spontaneously breathing patient, it is said to be triggered to do so. Triggering usually takes place at or near the initiation of the respiratory portion of the breathing cycle by the patient's efforts.

5.9.4 Anatomy 5.9.4.1 Anatomy of the Face

Ala: the external outer wall or "wing" of each nostril (plural: alar)

Alar angle: An angle formed between the ala of each nostril.

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius): The lip extending between the subnasale and the mouth.

Lip, upper (labrale superius): The lip extending between the mouth and the supramenton.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.9.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.9.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.9.5 Patient Interface

Anti-asphyxia valve (AAV): The component or sub-assembly of a mask system that, by opening to atmosphere in a failsafe manner, reduces the risk of excessive $CO_2$ rebreathing by a patient.

Headgear: Headgear will be taken to mean a form of positioning and stabilizing structure designed to hold a device, e.g. a mask, on a head.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.9.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.9.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.9.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill)

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.9.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.9.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.10 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Furthermore, "approximately", "substantially", "about", or any similar term used herein means+/−5-10% of the recited value.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 5.11 REFERENCE SIGNS LIST | |
|---|---|
| patient | 1000 |
| bed partner | 1100 |
| patient interface | 3000 |
| seal-forming structure | 3100 |
| plenum chamber | 3200 |
| chord | 3210 |
| superior point | 3220 |
| inferior point | 3230 |
| positioning and stabilising structure | 3300 |
| vent | 3400 |
| connection port | 3600 |
| forehead support | 3700 |
| RPT device | 4000 |
| external housing | 4010 |
| upper portion | 4012 |
| portion | 4014 |
| panel | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti - spill back valve | 4160 |
| air circuit | 4170 |
| air circuit | 4171 |
| electrical components | 4200 |
| single Printed Circuit Board Assembly PCBA | 4202 |
| power supply | 4210 |
| input device | 4220 |
| transducer | 4270 |
| humidifier | 5000 |
| humidifier inlet | 5002 |
| humidifier outlet | 5004 |
| humidifier base | 5006 |
| reservoir | 5110 |
| conductive portion | 5120 |
| humidifier reservoir dock | 5130 |
| locking lever | 5135 |
| water level indicator | 5150 |
| heating element | 5240 |
| patient interface | 7000 |
| body | 7010 |
| seal - forming structure | 7100 |
| nasal pillow | 7104 |
| plenum chamber | 7200 |
| wall | 7204 |
| inlet | 7208 |
| connecting member | 7212 |
| vent opening | 7216 |
| lip | 7220 |
| positioning and stabilising structure | 7300 |
| strap | 7310 |
| first portion | 7311 |
| second portion | 7312 |
| tube | 7350 |
| eyelet | 7351 |
| non - extendable tube section | 7363 |
| extendable tube section | 7364 |
| vent | 7400 |

-continued

| 5.11 REFERENCE SIGNS LIST | |
|---|---|
| vent body | 7405 |
| frame | 7420 |
| receptacle | 7425 |
| first flange | 7430 |
| second flange | 7435 |
| channel | 7440 |
| gaps | 7445 |
| vent wall | 7455 |
| outer surface | 7457 |
| vent hole | 7460 |
| connecting portion | 7464 |
| wall | 7468 |
| connection port | 7600 |
| elbow | 7610 |
| oral cushion | 8010 |
| seal - forming structure | 8100 |
| mouth portion | 8105 |
| vent opening | 8125 |
| receptacle | 8130 |
| base | 8135 |
| one side wall | 8140 |
| outer rim | 8145 |
| space | 8150 |
| receptacle opening | 8155 |
| connection body | 8159 |
| prong | 8160 |
| flat surface | 8161 |
| substantially straight surface | 8162 |
| curved surface | 8164 |
| first magnet | 8170 |
| second magnet | 8172 |
| plenum chamber | 8200 |
| wall | 8211 |
| headgear connector | 8231 |
| oral cushion strap | 8310 |
| lower strap portion | 8312 |
| connecting members | 8314 |
| rear strap | 8316 |
| first magnet | 8320 |
| second magnet | 8324 |
| material | 8328 |
| outer layers | 8332 |
| inner layer | 8336 |
| portion | 8340 |
| vent assembly | 8400 |

The invention claimed is:

1. A patient interface comprising:

a body comprising:

a nasal plenum chamber pressurisable to a therapeutic pressure of at least 4 cmH$_2$O above ambient air pressure, said nasal plenum chamber including at least one plenum chamber inlet port sized and structured to receive a flow of air at the therapeutic pressure for breathing by a patient;

a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the nasal plenum chamber throughout the patient's respiratory cycle in use; and a vent structure to allow a continuous flow of gases exhaled by the patient from an interior of the nasal plenum chamber to ambient, said vent structure being sized and shaped to maintain the therapeutic pressure in the nasal plenum chamber in use, and the vent structure comprising:

a housing secured to the nasal plenum chamber, and a vent wall coupled to the housing and selectively movable between a closed position and an open position, wherein the vent wall is biased toward the closed position, and wherein the vent wall is maintained in the closed position and is configured to be positioned in the open position as a result of contact with an oral cushion in order to accommodate the oral cushion with an oral plenum chamber and form an oro-nasal cushion; and a positioning and stabilising structure to provide a force to hold the seal-forming structure in a therapeutically effective position on the patient's head.

2. The patient interface of claim 1, wherein the vent wall is flexible relative to the housing.

3. The patient interface of claim 1, wherein the housing includes at least one magnet configured to removably connect to the oral cushion.

4. The patient interface of claim 1, wherein the positioning and stabilising structure includes one of more conduits configured to convey the therapeutic pressure to the nasal plenum chamber.

5. The patient interface of claim 1, wherein the positioning and stabilising structure includes a textile strap configured to contact an occipital portion of the patient's head, the textile strap including a magnet configured to connect to a lower strap usable with the oral plenum chamber.

6. The patient interface of claim 5, wherein the magnet is laminated to an outer surface of the textile strap.

7. The patient interface of claim 1, wherein the housing is permanently connected to the nasal plenum chamber.

8. The patient interface of claim 1, wherein the vent wall is movable into the nasal plenum chamber in the open position.

9. The patient interface of claim 1, wherein the vent wall includes a plurality of openings configured to vent air in the closed position.

10. The patient interface of claim 1, wherein the housing includes a lip extending at least partially around an inner perimeter, the vent wall configured to seal against the lip in the closed position.

11. A method of assembling a modular patient interface, the method comprising:

providing a nasal patient interface comprising:

a nasal plenum chamber pressurisable to a therapeutic pressure of at least 4 $cmH_2O$ above ambient air pressure, a nasal seal forming structure configured to seal with a patient's nares, a vent structure including a vent body connected to the nasal plenum chamber and a vent wall connected to the vent body and movable between a closed position and an open position, and a first positioning and stabilising structure configured to provide a tensile force for holding the nasal seal forming structure in an operative position;

providing an oral cushion comprising:

an oral plenum chamber pressurisable to the therapeutic pressure of at least 4 $cmH_2O$ above ambient air pressure;

an oral seal forming structure configured to seal with the patient's mouth, a receptacle disposed outside of the oral plenum chamber and spaced apart from the oral seal forming structure, the receptacle comprising, a receptacle opening providing fluid communication with the oral plenum chamber, and at least one prong disposed around at least a portion of the perimeter of the receptacle opening;

a second positioning and stabilising structure configured to hold the nasal seal forming structure in the operative position; and positioning the nasal patient interface in the receptacle and aligning the vent structure with the receptacle opening;

inserting the at least one prong into the nasal plenum chamber by moving the vent wall to the open position;

connecting the nasal patient interface to the oral cushion so that the nasal plenum chamber and the oral plenum chamber are connected to one another in an air tight configuration; and connecting the first positioning and stabilising structure to the second positioning and stabilising structure.

12. The method of claim 11, further comprising connecting an air delivery tube to the nasal plenum chamber, the air delivery tube is configured to delivery pressurised air to the nasal plenum chamber, and wherein the air delivery tube is configured to deliver the pressurised air to the oral plenum chamber when the at least one prong is inserted into the oral plenum chamber.

13. The method of claim 12, wherein the air delivery tube is conduit headgear and forms at least part of the first positioning and stabilising structure.

14. The method of claim 11, wherein a surface in the receptacle includes a first magnet and the vent body includes a second magnet, and wherein connecting the nasal patient interface to the oral cushion is accomplished using a magnet connection.

15. The method of claim 11, wherein a surface in the receptacle includes a first mechanical connector and the vent body includes a second mechanical connector, and wherein connecting the nasal patient interface to the oral cushion is accomplished using a removable snap fit connection.

16. The method of claim 11, wherein the first positioning and stabilising structure includes a strap with a third magnet and the second positioning and stabilising structure includes a strap with a fourth magnet, and wherein connecting the first positioning and stabilising structure to the second positioning and stabilising structure is accomplished using a magnetic connection.

17. The method of claim 11, further comprising disconnecting the nasal patient interface from the oral cushion and using the nasal patient interface independently to deliver pressurised air to the patient.

18. The method of claim 17, wherein the vent wall returns to the closed position and seals against the vent body.

19. The method of claim 11, further comprising flexing the vent wall toward the nasal seal forming structure after inserting the at least one prong into the nasal plenum chamber.

20. The method of claim 11, wherein the vent body is permanently connected to the nasal plenum chamber.

* * * * *